(12) United States Patent
Strong et al.

(10) Patent No.: US 11,098,053 B2
(45) Date of Patent: Aug. 24, 2021

(54) ENHANCED OSTEOGENIC ACTIVITY OF DAIDZEIN ANALOGS ON HUMAN MESENCHYMAL STEM CELLS

(71) Applicants: THE ADMINISTRATORS OF THE TULANE EDUCATIONAL FUND, New Orleans, LA (US); XAVIER UNIVERSITY OF LOUISIANA, New Orleans, LA (US); THE UNITED STATES OF AMERICA, AS REPRESENTED BY THE SECRETARY OF AGRICULTURE, Washington, DC (US)

(72) Inventors: Amy Strong, New Orleans, LA (US); Stephen Boue, Washington, DC (US); Matthew Burow, New Orleans, LA (US); Bruce Bunnell, New Orleans, LA (US); Quan Jiang, New Orleans, LA (US); Shilong Zheng, New Orleans, LA (US); Guangdi Wang, New Orleans, LA (US)

(73) Assignees: THE ADMINISTRATORS OF THE TULANE EDUCATIONAL FUND, New Orleans, LA (US); XAVIER UNIVERSITY OF LOUISIANA, New Orleans, LA (US); THE UNITED STATES OF AMERICA, AS REPRESENTED BY THE SECRETARY OF AGRICULTURE, Washington, DC (US)

( * ) Notice: Subject to any disclaimer, the term of this patent is extended or adjusted under 35 U.S.C. 154(b) by 0 days.

(21) Appl. No.: 14/781,494

(22) PCT Filed: Apr. 4, 2014

(86) PCT No.: PCT/US2014/032908
§ 371 (c)(1),
(2) Date: Sep. 30, 2015

(87) PCT Pub. No.: WO2014/165723
PCT Pub. Date: Oct. 9, 2014

(65) Prior Publication Data
US 2016/0068542 A1    Mar. 10, 2016

Related U.S. Application Data

(60) Provisional application No. 61/865,050, filed on Aug. 12, 2013, provisional application No. 61/808,538, filed on Apr. 4, 2013.

(51) Int. Cl.
| C07D 493/04 | (2006.01) |
| A61K 31/352 | (2006.01) |
| A61K 35/28 | (2015.01) |
| C07D 311/36 | (2006.01) |
| A61K 45/06 | (2006.01) |
| A61L 27/54 | (2006.01) |
| C07D 311/04 | (2006.01) |

(52) U.S. Cl.
CPC .......... *C07D 493/04* (2013.01); *A61K 31/352* (2013.01); *A61K 35/28* (2013.01); *A61K 45/06* (2013.01); *A61L 27/54* (2013.01); *C07D 311/04* (2013.01); *C07D 311/36* (2013.01); *A61L 2300/412* (2013.01); *A61L 2430/02* (2013.01)

(58) Field of Classification Search
CPC ....... A61K 31/785; A61K 45/06; C08F 20/52; C08F 22/385; C08F 222/385; C08F 226/02; C08F 232/08
See application file for complete search history.

(56) References Cited

U.S. PATENT DOCUMENTS

| 8,962,679 | B2* | 2/2015 | Wang | A61K 31/352 |
| | | | | 514/456 |
| 9,669,004 | B2* | 6/2017 | Wang | A61K 31/352 |
| 2011/0104230 | A1 | 5/2011 | Shaker et al. | |
| 2013/0184475 | A1* | 7/2013 | Wang | A61K 31/352 |
| | | | | 549/387 |

FOREIGN PATENT DOCUMENTS

| CA | 2265049 A1 | 3/1998 |
| CA | 2433653 A1 | 7/2002 |
| JP | 47-032074 | 8/1972 |
| JP | 60-054379 | 3/1985 |
| JP | 11-292869 | 10/1999 |
| JP | 2004519455 A | 7/2004 |
| JP | 2009536610 A | 10/2009 |
| WO | 9808503 A1 | 3/1998 |
| WO | WO00/49009 * | 8/2000 |
| WO | 02055072 A1 | 7/2002 |

OTHER PUBLICATIONS

Keung, A Potential Site of Action of Daidzin, J. Med. Chem., 2000, p. 4169.*

(Continued)

*Primary Examiner* — Matthew P Coughlin
*Assistant Examiner* — Thurman Wheeler
(74) *Attorney, Agent, or Firm* — F. Brent Nix, Esq.; Rachel D. Rutledge, Esq.; Johnson, Marcou, Isaacs & Nix, LLC

(57) ABSTRACT

Disclosed are daidzein analogs having the formula (I). Also disclosed are compositions, include a disclosed daidzein analogs, methods of preventing or treating bone disease or bone injury and/or stimulating bone growth, in a subject that include administering to the subject an effective amount of disclosed daidzein analog. Disclosed are isolated mesenchymal stem cell that has been altered by treatment a disclosed daidzein analog, daidzein, glycinol, glyceollin I, or glyceollin II, to increase the osteogenic potential of the mesenchymal stem cells.

10 Claims, 14 Drawing Sheets

Specification includes a Sequence Listing.

(56) References Cited

OTHER PUBLICATIONS

Al-Hazimi, Nat. Pterocarpanoids, J. King Saud Univer. Science p. 93, 2000.*
Keung et al The Mitochondrial Monoamine Oxidase-Aldehyde Dehydrogenase Pathway: A Potential Site of Action of Daidzin, J. Med. Chem., 2000, pp. 4169-4179 (Year: 2000).*
Szeja Chemistry & Biology Interface 3,2, p. 95 (Year: 2013).*
Yadav, Synthetic analogs of daidzein, Bioorganic & Medicinal Chemistry Letters, p. 677 (Year: 2011).*
European Partial Search Report for European Patent Application No. 14780030.4, Nov. 11, 2016, 10.
Gao, et al., "Synthesis of Potential Antidipsotropic Isoflavones", Journal of Medicinal Chemistry, vol. 44, No. 20, Jan. 1, 2001, 3320-3328.
Jiang, et al., "Effects of 7-0 Substitutions on Estrogenic and Anti-Estrogenic Activities of Daidzein Analogues in MCF-7 Breast Cancer Cells", Journal of Medicinal Chemistry, vol. 53, No. 16, Aug. 26, 2010, 6153-6163.
Srivastava, et al., "Isoformononetin, a Mthoxydaidzein Present in Medicinal Plants, Reverses Bone Loss in Osteopenic Rats and Exerts Bone Anabolic Action by Preventing Osteoblast Apoptosis", Phytomedicine, vol. 20, No. 6, Apr. 1, 2013, 470-480.
Yadav, et al., "Synthetic Analogs of Daidzein Having More Potent Osteoblast Stimulating Effect", Bioorganic & Medicinal Chemistry Letters, vol. 21, No. 2, Jan. 15, 2011, 677-681.
Extended European Search Report and Written Opinion for European Patent Application No. 14780030.4, Feb. 16, 2017, 15.
PubChem. Compound Summary for: CID 20496761. Create Date: Dec. 5, 2007 (retrieved on Oct. 21, 2014). Retrieved from the Internet: https://pubchem.ncbi.nlm.nih.gov/compound/20496761?from=summary>., Oct. 21, 2014, 15 pages.
PubChem. Compound Summary for CID 44257478. Create Date: Nov. 17, 2009 (retrieved on Oct. 21, 2014). Retrieved from the Internet http://pubchem.ncbi.nlm.nih.gov/compound/44257478?from=summary>, Oct. 21, 2014, 3 pages.
International Search Report and Written Opinion dated Nov. 12, 2014 for PCT/US2014/032908, Nov. 12, 2014, 29.
"First Office Action", Japanese Patent Application No. 2016-506632, dated Apr. 23, 2018.
An, et al., "Chain Length Effects in Isoflavonoid Daidzein Alkoxy Derivatives as Antioxidants: A Quantum Mechanical Approach", Journal of Agricultural and Food Chemistry, 2011, 59 (23), 12652-12657, DOI: 10.1021/jf2030314, 12652-12657.
Didziapetris, et al., "Computer-Aided Molecular Design", Journal of Computer-Aided Molecular Design, 2010, 24 (11), 891-906, DOI: 10.1007/s10822-010-9381-1.
Office Action issued by the Canadian Intellectual Property Office dated May 4, 2020 for counterpart application No. 2,904,533.

* cited by examiner

ENHANCED OSTEOGENIC ACTIVITY OF DAIDZEIN ANALOGS ON HUMAN MESENCHYMAL STEM CELLS

CROSS REFERENCE TO RELATED APPLICATION

This application is the U.S. National Stage of International Application No. PCT/US2014/032908, filed Apr. 4, 2014, published in English under PCT Article 21(2), which claims the priority benefit of the earlier filing date of U.S. Provisional Application No. 61/808,538, filed Apr. 4, 2013, and 61/865,050, filed Aug. 12, 2013, both of which are hereby specifically incorporated by reference in their entirety.

STATEMENT OF GOVERNMENT SUPPORT

This invention was made with government support under Grant No. 1G12RR026260-01, awarded by the National Institutes of Health and Grant No. 58-6435-7-019, awarded by the U.S. Department of Agriculture. The government has certain rights in the invention.

FIELD OF THE DISCLOSURE

The present disclosure relates to novel daidzein analogs, a method of increasing osteogenesis in humans using daidzein analogs, mesenchymal stem cells, and a method of treating and/or preventing various bone injuries and/or bone diseases in mammals.

BACKGROUND

Osteoporosis is a pathological condition associated with bone degeneration and is characterized by low bone mass and alterations to the architecture of the bone. The low bone density and compromised architecture results in reduced bone strength and increased susceptibility to fractures, leading to significant morbidity and mortality. While many factors contribute to the development of osteoporosis, age will likely be the leading risk factor due to the aging population in the United States. It is estimated that more than 2 million people suffer from osteoporosis at a cost of $17 billion annually in the United States.

Current treatment regimens for osteoporosis target bone regeneration or bone resorption, as these two processes are normally balanced in order to maintain strong, healthy bones. As such, therapeutic compounds have been divided into two groups: anti-resorptive drugs and anabolic drugs. Anti-resorptive drugs reduce the breakdown of bone during normal remodeling and reduce bone loss by limiting osteoclast activity. These drugs include bisphosphonate, calcitonin, and denosumab. Studies have shown that delivery of these drugs independently or in combination are effective in reducing bone loss. While these drugs limit the severity of osteoporosis, it is still necessary for bone to undergo regeneration to restore the architecture of the bone and provide strength to the bones. Anabolic drugs have been shown to not only achieve higher bone mass density (BMD), but also improve the quality and the strength of the bone.

Estrogen is an anabolic drug that has been used for the treatment of osteoporosis in postmenopausal women. While estrogen is considered a powerful modulator of bone metabolism by reducing the development of osteoporosis and increasing BMD, its use in the form of hormone replacement therapy has been halted due to its association with an increased risk of breast and endometrial cancers. Therefore, effective alternatives to estrogen are necessary. Raloxifene, a selective estrogen receptor modulator, has been shown to produce estrogen-agnostic effects on bone and estrogen-antagonistic effects on uterine, endometrium, and breast tissue. However, it has also been associated with increased risk of thromboembolic events.

There remains a need to identify superior pharmacological therapies to treat osteoporosis. Although increasing physical activity is a modifiable lifestyle choice that can reduce the incidence of osteoporosis, the development of novel therapeutic interventions will further reduce the development of osteoporosis by supporting healthier bones over an individual's lifetime. This disclosure meets those needs.

SUMMARY

Disclosed are daidzein analogs having the formula:

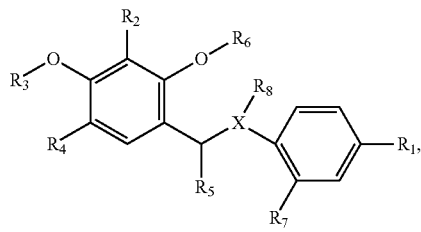

wherein $R_1$ is hydrogen,

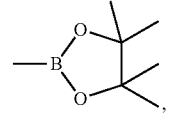

$OR_9$, and wherein the $R_9$ is hydrogen or lower alkyl; $R_2$ is hydrogen or when taken together with $R_3$ form a five or six membered ring that can be optionally substituted at $R_3$ with one or more lower alkyls wherein the ring can be an aromatic ring; $R_3$ is hydrogen, alkyl, lower alkyl, allyl, Cyclopentyl, n-Hexyl, propyne, 2-(Piperdin-1-yl)ethyl, 2-(Pyrrolidin-1-yl)ethyl, or 2-(Dimethylamino)ethyl; $R_4$ is hydrogen or when taken together with $R_3$ form a five or six membered ring that can be optionally substituted at $R_3$ with one or more lower alkyls and wherein the ring can be an aromatic ring; $R_5$ is one or more of hydrogen, oxygen, or $OR_{10}$, wherein $R_{10}$ is hydrogen or lower alkyl; $R_6$ is hydrogen, carbon, or lower alkyl; $R_7$ is hydrogen, or a bond, and when taken together with $R_5$ and $R_7$ is a bond $R_5$ and $R_7$ form a five membered ring wherein $R_5$ is oxygen; $R_8$ is hydrogen or $OR_{11}$ wherein $R_{11}$ is hydrogen or lower alkyl; and X is carbon or nitrogen, and wherein, when X is carbon, $R_6$ is carbon and X and $R_6$ are joined by a carbon-carbon bond, wherein the compound is not daidzein, glycinol, glyceollin I, or glyceollin II. In certain examples, daidzein analogs is one of 3-(4-Hydroxyphenyl)-7-isopropoxy-4H-chromen-4-one, 7-Butoxy-3-(4-hydroxyphenyl)-4H-chromen-4-one, 3-(4-Hydroxyphenyl)-7-isobutoxy-4H-chromen-4-one, 7-Hexyloxy-3-(4-hydroxyphenyl)-4H-chromen-4-one, 7-(Allyloxy)-3-(4-hydroxyphenyl)-4H-chromen-4-one, 4-(8,8-Dimethyl-2,3,4,8-tetrahydropyrano[3,2-g]chromen-3-yl)phenol, 2,4-Dimethoxy-N-(4-methoxyphenyl)benzamide, 3-(4-Hydroxyphenyl)-7-methoxy-4H-chromen-4- one, 7-Ethoxy-3-(4-hydroxyphenyl)-4H-chromen-4-one, 7-Cyclopentyloxy-3-(4-hydroxyphenyl)-4H-chromen-4-one, 3-(4-Hydroxyphenyl)-8,8-dimethyl-2,3,9,10-tetrahydropyrano[2,3-f]chromen-4(8H)-one, 3-(4-Hydroxyphenyl)-7-(prop-2-yn-1-yloxy)-4H-chromen-4-one, 3-(4-Hydroxyphenyl)-8-methyl-4H-furo[2,3-h]chromen-4-one, 3-(4-Hydroxyphenyl)-7-propoxy-4H-chromen-4-one, 3-(4-Hydroxyphenyl)-7-(2-(piperidin-1-yl)ethoxy)-4H-chromen-4-one, and N-(4-Hydroxyphenyl)-2,4-dimethoxybenzamide.

Also disclosed are compositions, such as pharmaceutically compositions that include a disclosed daidzein analog and a pharmaceutically acceptable carrier. In some embodiments, the compositions further include mesenchymal stem cells, which in some examples have been pretreated with a disclosed daidzein analog, daidzein, glycinol, glyceollin I, or glyceollin II, for example to increase the osteogenic potential of the mesenchymal stem cells.

Also disclosed are methods of preventing or treating bone disease or bone injury, such as osteoporosis, osteopenia, or a bone fracture, in a subject that include administering to the subject an effective amount of disclosed daidzein analog.

Also disclosed are methods of stimulating bone growth in a subject, such as a subject with osteoporosis, osteopenia, or a bone fracture, in a subject that include administering to the subject an effective amount of disclosed daidzein analog.

Also disclosed are isolated mesenchymal stem cell that has been altered by treatment with a disclosed daidzein analog, daidzein, glycinol, glyceollin I, or glyceollin II, to increase the osteogenic potential of the mesenchymal stem cells.

Also disclosed are biocompatible bone repair system which includes a biocompatible substrate that has been coated with and/or seeded with a disclosed daidzein analogue and/or a mesenchymal stem cell, such as a mesenchymal stem cell treated with a disclosed daidzein analogue, daidzein, glycinol, glyceollin I, or glyceollin II. Also provided are methods of treating a bone defect with a disclosed biocompatible bone repair system, which includes surgically implanting the biocompatible substrate at the bone defect site.

The foregoing and other features will become more apparent from the following detailed description of several embodiments, which proceeds with reference to the accompanying figures.

BRIEF DESCRIPTION OF THE DRAWINGS

(FIG. 1A) Representative images of Alizarin Red stained MSCs treated with vehicle, estrogen, daidzein, or genistein. Images were acquired at 4× magnification. (FIG. 1B) Bone differentiation was determined relative to vehicle-treated cells normalized to 1.0. *, P<0.05, **, P<0.01.

(FIG. 6A) After 14 days, cells treated with estrogen, daidzein, or genistein and induced with osteogenic differentiation media were fixed, stained with alizarin red, and visualized with bright field microscopy at 4× magnification. Scale bar represents 100 µm. (FIG. 6B) To quantify the amount of alizarin red staining in BMSCs and ASCs treated with vehicle, estrogen, or phytoestrogens, cells were eluted with 10% CPC and measured at 590 nm. Osteogenic differentiation was determined relative to vehicle-treated cells (normalized to 1.0). (FIG. 6C) After 14 days, cells induced with adipogenic differentiation media were fixed and stained with oil red o and visualized with bright field microscopy at 10× magnification. Scale bar represents 100 µm. (FIG. 6D) To quantify the amount of oil red o staining in BMSCs and ASCs treated with vehicle, estrogen, or phytoestrogens, cells were eluted with isopropanol and measured at 544 nm. Adipogenic differentiation was determined relative to vehicle-treated cells (normalized to 1.0). **, P<0.01.

(FIG. 7A) After 14 days, cells induced with osteogenic differentiation media were fixed, stained with alizarin red, and visualized with bright field microscopy at 4× magnification. Scale bar represents 100 µm. (FIG. 7B) To quantify the amount of alizarin red staining in BMSCs and ASCs treated with vehicle, estrogen, daidzein, or daidzein analogs, cells were eluted with 10% CPC and measured at 590 nm. Osteogenic differentiation was determined relative to vehicle-treated cells normalized to 1.0. *, P<0.05; **, P<0.01 compared to vehicle-treated cells. $^{\#\#\#}$, P<0.001 compared to estrogen-treated cells. $^{YYY}$, P<0.001 compared to daidzein-treated cells.

(FIG. 8A) BMSCs (n=6) and (FIG. 8B) ASCs (n=6) were cultured in osteogenic differentiation media and simultaneously delivered vehicle, estrogen, daidzein, or daidzein analog at concentrations between 100 pm to 1 mM. After 14 days, cells were fixed, stained with alizarin red, destained with 10% CPC, and measured at 590 nm. Osteogenic differentiation was determined relative to vehicle-treated cells normalized to 1.0.

(FIG. 9A) After 3 days, cells were stained were fixed and stained with alkaline phosphatase. (FIG. 9B) To quantify alkaline phosphatase staining, the number of positive pixels per image (for a total of 5 images) was counted by Image J. (FIG. 9C) After 14 days, cells were stained were fixed and stained with silver nitrate. (FIG. 9D) To quantify phosphate deposition after silver nitrate staining, the number of pixels per image (for a total of 5 images) was counted by Image J.*, P<0.001 compared to estrogen-treated cells. Images were acquired at 4× magnification. Scale bar represents 100 µm. *, P<0.001 compared to vehicle-treated cells; $^{\#}$, P<0.05 compared to estrogen-treated cells; $^{\#\#\#}$, P<0.001 compared to estrogen-treated cells; $^{\Psi\Psi\Psi}$, P<0.001 compared to daidzein-treated cells.

(FIGS. 12A and 12C) After 14 days, cells were stained with alizarin red and eluted with CPC. Quantification of the stain was measured at 590 nm and normalized to differentiated vehicle-treated cells. (FIGS. 12B and 12D) Cells were collected after 3, 7, or 14 days of treatment. RNA was isolated from the cells and reverse transcribed into cDNA. Analyses of osteogenic transcription factors were assessed by qPCR. Expression values are normalized to undifferentiated vehicle-treated cells set to 1.0. Treated MSCs were normalized to undifferentiated MSCs, while treated ASCs were normalized to undifferentiated ASCs. *, P<0.05 compared to vehicle-treated cells; , P<0.01 compared to vehicle-treated cells;*, P<0.001 compared to vehicle-treated cells; $^{\#\#\#}$, P<0.001 compared to estrogen-treated cells; $^{YYY}$, P<0.001 compared to daidzein-treated cells.

BRIEF DESCRIPTION OF THE SEQUENCES

Figure 1A:
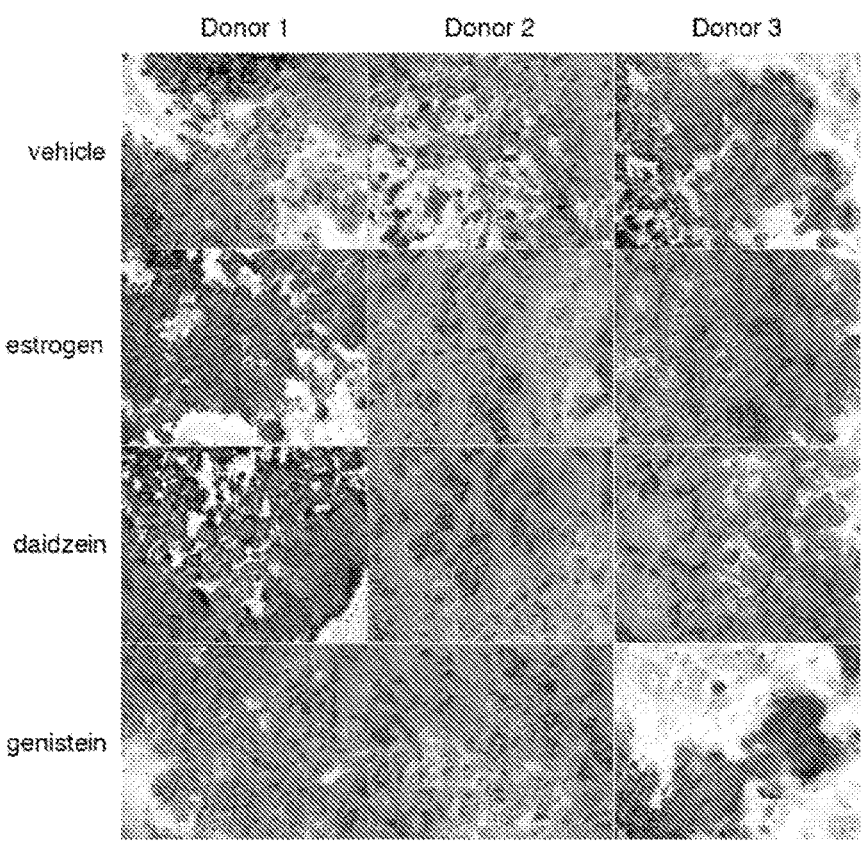
FIGS. 1A and 1B are a set of digital images and bar graphs showing that phytoestrogens enhance osteogenesis of MSC. MSCs from three donors were induced to differentiate and simultaneously exposed to estrogen (10 nM), daidzein (1 µM), and genistein (1 µM). MSCs induced to undergo osteogenesis for 14 days were stained with Alizarin Red S to detect calcium deposits, destained with cetylpyridinium chloride, and measured at 590 nm to quantify the amount of osteogenic differentiation.

The nucleic acid sequences shown herein are shown using standard letter abbreviations for nucleotide bases, as defined in 37 C.F.R. 1.822. Only one strand of each nucleic acid sequence is shown, but the complementary strand is understood as included by any reference to the displayed strand. The Sequence Listing is submitted as an ASCII text file in the form of the file named TUL_0011WP_ST25.txt, which was created on Apr. 3, 2014, and is 4 kilobytes, which is incorporated by reference herein.

DETAILED DESCRIPTION OF SEVERAL EMBODIMENTS

I. Summary of Terms

Unless otherwise explained, all technical and scientific terms used herein have the same meaning as commonly understood by one of ordinary skill in the art to which the disclosed subject matter belongs. Definitions of common terms in chemistry terms may be found in *The McGraw-Hill Dictionary of Chemical Terms*, 1985, and *The Condensed Chemical Dictionary*, 1981. As used herein, the singular terms "a," "an," and "the" include plural referents unless context clearly indicates otherwise. Similarly, the word "or" is intended to include "and" unless the context clearly indicates otherwise. Also, as used herein, the term "comprises" means "includes." Hence "comprising A or B" means including A, B, or A and B.

Except as otherwise noted, any quantitative values are approximate whether the word "about" or "approximately" or the like are stated or not. The materials, methods, and examples described herein are illustrative only and not intended to be limiting. Any molecular weight or molecular mass values are approximate and are provided only for description. Except as otherwise noted, the methods and techniques of the present invention are generally performed according to conventional methods well known in the art and as described in various general and more specific references that are cited and discussed throughout the present specification. See, e.g., Loudon, *Organic Chemistry*, Fourth Edition, New York: Oxford University Press, 2002, pp. 360-361, 1084-1085; Smith and March, *March's Advanced Organic Chemistry: Reactions, Mechanisms, and Structure*, Fifth Edition, Wiley-Interscience, 2001; or Vogel, *A Textbook of Practical Organic Chemistry, Including Qualitative Organic Analysis, Fourth Edition*, New York: Longman, 1978.

In order to facilitate review of the various embodiments disclosed herein, the following explanations of specific terms are provided:

Administration: To provide or give a subject a composition, such as a pharmaceutical composition including a disclosed daidzein analog, by any effective route. Exemplary routes of administration include, but are not limited to, injection (such as subcutaneous, intramuscular, intradermal, intraperitoneal (ip), and intravenous (iv)), oral, sublingual, transdermal, and inhalation routes.

Alkoxy: A radical (or substituent) having the structure —O—R, where R is a substituted or unsubstituted alkyl. Methoxy (—OCH$_3$) is an exemplary alkoxy group. In a substituted alkoxy, R is alkyl substituted with a non-interfering substituent. "Thioalkoxy" refers to —S—R, where R is substituted or unsubstituted alkyl. "Haloalkyloxy" means a radical —OR where R is a haloalkyl.

Alkenyl: A unsaturated monovalent hydrocarbon having a number of carbon atoms ranging from one to ten (e.g., C$_{2-10}$alkenyl), which has at least one carbon-carbon double bond and is derived from removing one hydrogen atom from one carbon atom of a parent alkene. An alkenyl group may be branched, straight-chain, cyclic, cis, or trans (e.g., E or Z).

Alkynyl: A unsaturated monovalent hydrocarbon having a number of carbon atoms ranging from one to ten (e.g., C$_{2-10}$alkynyl), which has at least one carbon-carbon triple bond and is derived from removing one hydrogen atom from one carbon atom of a parent alkyne. An alkynyl group may be branched, straight-chain, or cyclic.

Alkyl: An acyclic, saturated, branched- or straight-chain hydrocarbon radical, which, unless expressly stated otherwise, contains from one to fifteen carbon atoms; for example, from one to ten, from one to six, or from one to four carbon atoms. This term includes, for example, groups such as methyl, ethyl, n-propyl, isopropyl, isobutyl, t-butyl, pentyl, heptyl, octyl, nonyl, decyl, or dodecyl. The term "lower alkyl" refers to an alkyl group containing from one to four carbon atoms. Unless expressly referred to as an "unsubstituted alkyl," alkyl groups can either be unsubstituted or substituted. An alkyl group can be substituted with one or more substituents (for example, up to two substituents for each methylene carbon in an alkyl chain). Exemplary alkyl substituents include, for instance, amino groups, amide, sulfonamide, halogen, cyano, carboxy, hydroxy, mercapto, trifluoromethyl, alkyl, alkoxy (such as methoxy), alkylthio, thioalkoxy, arylalkyl, heteroaryl, alkylamino, dialkylamino, alkylsulfano, keto, or other functionality.

Analog or Derivative: A compound which is sufficiently homologous to a compound such that it has a similar functional activity for a desired purpose as the original compound. Analogs or derivatives refers to a form of a substance, such as daidzein, which has at least one functional group altered, added, or removed, compared with the parent compound. "Functional group" refers to a radical, other than a hydrocarbon radical, that adds a physical or chemical property to a substance.

Biocompatible: The property of a biomaterial or device having the ability to perform its desired function (for example, with respect to a medical therapy), without eliciting any undesirable local or systemic effects in a subject. A biocompatible material or device ideally also generates a beneficial effect or cellular or tissue response. In some examples, biocompatible refers to a material or device that is enzymatically or chemically degraded in vivo into simpler chemical species ("biodegradable"). A biocompatible material, device, or system includes synthetic or natural material used to replace part of a living system or to function in intimate contact with living tissue. The terms "biocompatible" and "biologically compatible" are used interchangeably herein.

Bone defect: Includes any disease, defect, or disorder which affects bone strength, function, and/or integrity, such as those resulting from injury, or a defect brought about during the course of surgery, infection, malignancy, or developmental malformation. Examples of bone defects include, but are not limited to, fractures (such as a critical defect or non-union fracture), dental or facial defects (such as cleft palate or facial or dental injuries or malformations). Other examples of bone defects include damage to bones resulting from diseases of bone fragility, such as osteopenia, osteoporosis, and malignancies and/or cancers of the bone such as a sarcoma, such as osteosarcoma.

Coat: As used herein "coating", "coatings", "coated" and "coat" are forms of the same term defining material and process for making a material where a first substance or substrate surface is at least partially covered or associated with a second substance. Both the first and second substance are not required to be different. Further, when a device or biocompatible substrate is "coated" as used herein, the coating may be effectuated by any chemical or mechanical bond or force, including linking agents. Thus a device composed of a first substance may be "coated" with a second substance via a linking agent that is a third substance. As used herein, the "coating" need not be complete or cover the entire surface of the first substance to be "coated". The "coating" may be complete as well (e.g., approximately covering the entire first substance). There can be multiple coatings and multiple substances within each coating. The coating may vary in thickness or the coating thickness may be substantially uniform.

Cell culture: Growth of a population of cells in a defined set of conditions (such as culture medium, temperature, and/or time of culture). In some examples, a cell culture includes a substantially pure culture (for example, isolated mesenchymal stem cells or adipose-derived stem cells). In additional examples a cell culture includes a mixed culture, such as co-culture of two or more types of cells (for example a culture of bone marrow cells, including one or more of fibroblasts, macrophages, mesenchymal stem cells, and hematopoietic cells), cells at different stages of differentiation (for example, a mixture of multipotent stem cells and differentiated cells) or a combination thereof. In further examples, a cell culture includes cells grown in contact with one or more biocompatible substrates, such as a sponge, strip, scaffold, or gel (such as a collagen sponge or nylon strip).

Control or Reference Value: A "control" refers to a sample or standard used for comparison with an experimental sample.

Diagnosis: The process of identifying a disease, such as a bone defect, such as osteoporosis, or a bone fracture, by its signs, symptoms and results of various tests. The conclusion reached through that process is also called "a diagnosis." Forms of testing commonly performed include blood tests, and medical imaging.

Differentiate: A change in the characteristics of a cell such that a less specialized cell becomes more specialized. Differentiation may cause changes in the size, shape, polarity, gene expression, metabolic activity, and responsiveness to signals of a cell. In a particular example, a mesenchymal stem cell differentiates to an osteogenic cell when the cell exhibits at least one marker of mineralization, such as an increase in expression or activity of a mineralization gene or protein or an increase in calcium secretion.

Fracture: A medical condition in which a bone is cracked or broken; a break in the continuity of a bone. Fractures may be classified as closed or open. A closed fracture is one in which the skin is intact; an open (or compound) fracture is one in which the bone is in contact with the air (such as piercing the skin or due to severe tissue injury). Fractures are also classified as simple or multi-fragmentary. A simple fracture occurs along only one line (such as splitting a bone into two pieces), while a multi-fragmentary fracture splits a bone into multiple pieces (such as three or more pieces). Other types of fracture include complete, incomplete, linear, transverse, oblique, compression, spiral, comminuted, and compacted fractures. Additional fractures include a critical defect (such as when part of a bone is lost or removed) and a non-union fracture (such as when the ends of the fracture are not in contact with each other).

Inhibiting a disease or condition: A phrase referring to reducing the development of a disease or condition, for example, in a subject who is at risk for a disease or who has a particular disease, such as a bone defect, for example osteoporosis. Particular methods of the present disclosure provide methods for inhibiting osteopenia and/or osteoporosis.

Mesenchymal stem cells, or MSCs: Multipotent stromal cells that can differentiate into a variety of cell types including: osteoblasts (bone cells), chondrocytes (cartilage cells), and adipocytes (fat cells). MSCs have a great capacity for self-renewal while maintaining their multipotency.

Osteoblast: A mononucleate cell that is responsible for bone formation. Osteoblasts produce osteoid, which is composed mainly of Type I collagen. Osteoblasts are also responsible for mineralization of the osteoid matrix. Bone is a dynamic tissue that is constantly being reshaped by osteoblasts, which build bone, and osteoclasts, which resorb bone. Osteoblasts arise from osteoprogenitor cells located in the periosteum and the bone marrow. Osteoprogenitors are immature progenitor cells that express the master regulatory transcription factor Cbfa1/Runx2. Once osteoprogenitors start to differentiate into osteoblasts, they begin to express a range of markers including osterix, collagen type 1, alkaline phosphatase, osteocalcin, osteopontin, and osteonectin.

Osteoclast: A type of bone cell that removes bone tissue by removing its mineralized matrix by a process of bone resorption. Osteoclasts are formed by the fusion of cells of the monocyte-macrophage cell line. Osteoclasts are characterized by high expression of tartrate resistant acid phosphatase and cathepsin K.

Osteocyte: Mature, non-dividing bone cells that are housed in their own lacunae (small cavities in the bone). Osteocytes are derived from osteoblasts and they represent the final stage of maturation of the bone cell lineage. They are less active than osteoblasts, and although they are not responsible for a net increase in bone matrix, they are essential to the maintenance and routine turnover of the matrix. The narrow, cytoplasmic processes of osteocytes remain attached to each other and to osteoblasts through canaliculi (small channels in the bone).

Osteoporosis: A disease or condition characterized by low bone mass and structural deterioration of bone tissue, leading to an increased risk of fractures. The World Health Organization (WHO) defines osteoporosis as a spinal or hip bone mineral density (BMD) of 2.5 standard deviations or more below the mean for healthy, young women (T-score of −2.5 or below) as measured by dual energy x-ray absorptiometry (DEXA).

The related disorder, osteopenia is defined as a spinal or hip BMD between 1 and 2.5 standard deviations below the mean. It is believed that primary osteoporosis is the result of bone loss related to the decline in gonadal function associated with aging. Secondary osteoporosis may result from chronic diseases, exposures, or nutritional deficiencies that adversely impact bone metabolism.

Typically, osteoporosis is diagnosed clinically or radiographically. Osteoporosis may present with low-impact fractures (occurring from a fall at or below standing height) or fragility fractures (occurring spontaneously).

Pharmaceutically Acceptable Carriers: The pharmaceutically acceptable carriers (vehicles) useful in this disclosure are conventional. *Remington's Pharmaceutical Sciences*, by E. W. Martin, Pharmaceutical Publishing, London UK, 22th Edition (2012), describes compositions and formulations suitable for pharmaceutical delivery of one or more therapeutic compounds or molecules, such as one or more nucleic acid molecules, proteins or antibodies that bind these proteins, and additional pharmaceutical agents.

In general, the nature of the carrier will depend on the particular mode of administration being employed. For instance, parenteral formulations usually comprise injectable fluids that include pharmaceutically and physiologically acceptable fluids such as water, physiological saline, balanced salt solutions, aqueous dextrose, glycerol or the like as a vehicle. For solid compositions (for example, powder, pill, tablet, or capsule forms), conventional non-toxic solid carriers can include, for example, pharmaceutical grades of mannitol, lactose, starch, or magnesium stearate. In addition to biologically-neutral carriers, pharmaceutical compositions to be administered can contain minor amounts of non-toxic auxiliary substances, such as wetting or emulsifying agents, preservatives, and pH buffering agents and the like, for example sodium acetate or sorbitan monolaurate.

Prodrug: A compound that is transformed in vivo to yield a parent compound, for example, by hydrolysis in the gut or enzymatic conversion in blood.

Purified: The term "purified" does not require absolute purity; rather, it is intended as a relative term. Thus, for example, a purified preparation is one in which a desired component is more enriched than it was in a preceding environment, for example, when at least about 70%, 80%, 85%, 90%, 92%, 95%, 97%, 98%, or 99% of a sample by weight is composed of the desired component. Purity of a compound may be determined, for example, by high performance liquid chromatography (HPLC) or other conventional methods. In an example, the specific daidzein analogues are purified to represent greater than 90%, often greater than 95%.

Compounds described herein may be obtained in a purified form or purified by any of the means known in the art, including silica gel and/or alumina chromatography. See, e.g., *Introduction to Modern Liquid Chromatography*, 2nd Edition, ed. by Snyder and Kirkland, New York: John Wiley and Sons, 1979; and *Thin Layer Chromatography*, ed. by Stahl, New York: Springer Verlag, 1969. In an example, a compound includes purified daidzein analogue with a purity of at least about 70%, 80%, 85%, 90%, 92%, 95%, 97%, 98%, or 99% of a sample by weight relative to other contaminants.

Repair: New bone formation which is sufficient to at least partially fill a void or structural discontinuity at the site of a bone defect. The term repair does not require a process of complete healing or a treatment which is 100% effective at restoring a defect to its pre-defect state.

Subject: The term "subject" includes both human and veterinary subjects, for example, humans, non-human primates, dogs, cats, horses, rats, mice, and cows. Similarly, the term mammal includes both human and non-human mammals.

Therapeutically Effective Amount: A quantity of a specified agent sufficient, such as the compounds described herein to achieve a desired effect in a subject being treated with that agent. For example, this may be the amount of a disclosed daidzein derivative useful in preventing, inhibiting, and/or treating bone loss, and/or promoting bone formation, for example in a subject with osteoporosis. Ideally, a therapeutically effective amount of an agent is an amount sufficient to prevent, inhibit, and/or treat the disorder in a subject without causing a substantial cytotoxic effect in the subject.

The effective amount of a composition useful for preventing, inhibiting, and/or treating a disorder in a subject will be dependent on the subject being treated, the severity of the disorder, and the manner of administration of the therapeutic composition. Effective amounts a therapeutic agent can be determined in many different ways, such as assaying for bone density. Effective amounts also can be determined through various in vitro, in vivo or in situ assays.

Stem cell: A cell that can generate a fully differentiated functional cell of more than one given cell type. The role of stem cells in vivo is to replace cells that are destroyed during the normal life of an animal. Generally, stem cells (for example, embryonic stem cells) can divide without limit and are totipotent. After division, the stem cell may remain as a stem cell, become a precursor cell, or proceed to terminal differentiation. A multipotent stem cell is a stem cell that can generate a fully differentiated cell of more than one given cell type, but is not totipotent. In one example, a multipotent stem cell includes a mesenchymal cell that can self-renew and can generate bone-forming or mineral-forming cells, such as osteoblasts. Multipotent stem cells may be derived from tissues of a post-natal subject, for example, from bone marrow and adipose tissue. An osteogenic cell is a cell that can generate a fully differentiated functional bone cell of at least one given cell type from the body of an animal, such as a human. An osteogenic cell can generate a fully differentiated bone cell, such as, but not limited to, an osteocyte, pre-osteoblast, osteoblast, pre-osteoclast, and/or osteoclast.

After division, an osteogenic cell can remain a precursor cell (e.g. a cell that can generate a fully differentiated functional cell of at least one given cell type from the body of an animal), or may proceed to terminal differentiation. An osteogenic cell can give rise to one or more types of bone cells, such as osteocytes, pre-osteoblasts, osteoblasts, pre-osteoclasts, and/or osteoclasts, but is more limited in its ability to differentiate than a stem cell.

Substrate: A substance, framework, scaffold, or support on which cells may be grown and/or differentiated. The cells may be attached to the exterior of the substrate or may migrate into the substrate, for example into pores in the substrate. In some examples, a substrate is a sponge, strip, gel (such as a hydrogel), scaffold, or other three-dimensional structure. In a particular example, the substrate is a collagen sponge or a nylon strip.

Under conditions sufficient for: A phrase that is used to describe any environment that permits the desired activity. In one example, under conditions sufficient for includes administering one or more daidzein analogues or a combination thereof to a subject to at a concentration sufficient to allow the desired activity. In some examples, the desired activity is preventing or inhibiting a sign or symptom associated with bone loss, such as osteoporosis, a reduction in severity of some or all clinical symptoms, a slower progression, an improvement in the overall health or well-being of the subject, or by other parameters well known in the art that are specific to the particular disease. Therapy does not need to be completely effective for the treatment to be considered effective. For example, a partial reduction or slowing of bone loss as at least about a 5% reduction, such as at least 10%, at least about 20%, at least about 30%, at least about 40%, at least about 50% or greater.

II. Overview of Several Embodiments

A. Introduction

Osteoporosis, defined by the loss of bone mass and strength, results in the loss of structural and mechanical support in bone and leads to an increased risk of fractures. In the adult skeleton, the bone undergoes continuous resorption carried out by osteoclast cells and formation by osteoblast cells to regulate the amount of bone present. With osteoporosis, an overstimulation of osteoclast activity is observed, resulting in the destruction of the bone extracellular matrix. Without the normal architecture, osteoblast cells are unable to rebuild phenotypically normal bone. Hormone replacement therapy, with estrogen, has been efficacious at increasing osteoblast activity, but also has resulted in the increased incidence of breast and uterine cancer. Other plant-derived estrogens or phytoestrogens, such as daidzein, have recently been investigated and showed to have osteogenic activity.

As disclosed herein, the inventors have designed and synthesized a series of daidzein analogs to investigate the osteogenic induction of these compounds. Human bone marrow derived mesenchymal stem cells (MSCs) from three different donors were treated with daidzein analogs and demonstrated enhanced osteogenesis when compared to estrogen or daidzein. The enhanced osteogenic potential of these daidzein analogs resulted in increased osterix (Sp7), alkaline phosphatase (ALP), osteopontin (OPN), and insulin-like growth factor 1 (IGF-1), which are osteogenic transcription factors that regulate the maturation of osteogenic progenitor cells into mature osteoblast cells.

Daidzein is known to be a potent estrogenic compound that has beneficial effect on bone health but its clinical potential is limited by its low bioavailability, unfavorable metabolism and uterine estrogenicity.

In the studies disclosed herein, the utility of a series of daidzein analogs was investigated in the promotion of bone formation. The effects of structural variations of daidzein on the osteogenic induction of human bone marrow derived MSCs, which differentiate into osteoblasts under appropriate stimulation, were explored.

Structural variations at the 7-hydroxy position and the central daidzein moiety were made to test how the osteogenic activities varied as a result of such changes in substitution and the daidzein skeleton. Because it has been shown recently that equol, the metabolic product of daidzein may be responsible for its superior bone-healing property compared to genistein and other isoflavones, several equol analogs were also synthesized and tested for potential gain of activity.

As disclosed herein daidzein analogs are potent stimulators of osteogenesis in human bone marrow derived mesenchymal stem cells (MSCs) in a dose-dependent manner. Cells treated with estrogen, daidzein, or genistein increased calcium deposition by 1.6-, 1.5-, and 1.4-fold, respectively, relative to vehicle-treated BMSCs and 1.6-, 1.7-, and 1.4-fold relative to vehicle-treated ASCs, respectively. By comparison, cells treated with daidzein analogs demonstrated enhanced osteogenesis. For example, BMSCs treated with daidzein analog 2c, 2g, and 2l demonstrated a 1.6-, 1.6-, and 1.9-fold increase in osteogenic differentiation relative to vehicle-treated BMSCs, respectively, while ASCs treated with daidzein analog 2c, 2g, or 2l demonstrated an 1.7-, 2.0-, and 2.2-fold increase in osteogenic differentiation relative to vehicle-treated ASCs, respectively. Thus, the results presented herein demonstrate that the disclosed daidzein derivatives can be used for the treatment of bone diseases and injuries, such as osteoporosis, osteopenia and bone fractures and are superior in induction of ontogenesis.

In addition, mesenchymal stem cells, such as ASCs, can be easily isolated, which makes then ideal ideal candidates for tissue engineering and regenerative purposes, in conjunction with the disclosed daidzein derivatives. For example mesenchymal stem cells such as ASCs and BMSCs can be seeded on to biocompatible scaffolds to increase bone formation. Additionally, the daidzein analogs disclosed herein can be coated onto these scaffolds.

Furthermore, in the case where these compounds are used in postmenopausal women, an important advantage of the daidzein analogs compounds is the limited estrogenic effect of these compounds on cancer cells. Previous studies have determined that daidzein and daidzein derivatives had negligible effects on cancer growth or progression. As such, these compounds could be used in combination with chemotherapy or other forms of cancer therapy to reduce the incidence of osteoporosis in at risk patients. Furthermore, these compounds could be used in combination with other anti-osteoporotic drugs to B. Compounds Disclosed are compounds, collectively referred to herein as daidzein derivatives and/or analogues, that may be used as for the treatment of bone defects, such as bone diseases and injuries, such a osteopenia, osteoporosis, and bone fractures or other injuries and situations in which prevention or inhibition of bone loss or stimulation of bone growth is desired. Other uses for the compounds include induction of early, middle, and late genes involved in osteogenesis in in vitro assays as other uses as described in the Examples below, such as increasing the osteogenic potential of mesenchymal stem cells, for example bone marrow-derived mesenchymal stem cells (BMSCs) or adipose-derived stromal/stem cells (ASC). In particular disclosed embodiments, the compound is effective in treating osteopenia, osteoporosis, and bone fractures. The compound is a small-molecule therapeutic. In particular disclosed embodiments, the small-molecule therapeutic is a multi cyclic compound of the formula illustrated below:

Formula I

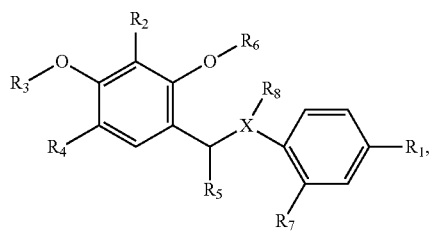

wherein $R_1$ independently is hydrogen,

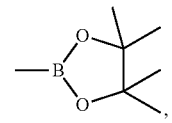

$OR_9$, or any combination thereof, and wherein the $R_9$ independently is hydrogen or lower alkyl; $R_2$ independently is hydrogen or when taken together with $R_3$ forms a five or six membered ring that can be optionally substituted at $R_3$ with one or more lower alkyls wherein the ring can be an aromatic ring, or any combination thereof; $R_3$ independently is hydrogen, alkyl, lower alkyl, allyl, Cyclopentyl, n-Hexyl, propyne, 2-(Piperdin-1-yl)ethyl, 2-(Pyrrolidin-1-yl)ethyl, or 2-(Dimethylamino)ethyl, or any combination thereof; $R_4$ independently is hydrogen or when taken together with $R_3$ forms a five or six membered ring that can be optionally substituted at $R_3$ with one or more lower alkyls and wherein the ring can be an aromatic ring, or any combination thereof; $R_5$ independently is one or more of hydrogen, oxygen, or $OR_{10}$, or any combination thereof, wherein $R_{10}$ independently is hydrogen or lower alkyl; $R_6$ independently is hydrogen, carbon, or lower alkyl, or any combination thereof; $R_7$ independently is hydrogen, or a bond, or when taken together with $R_5$ and $R_7$ is a bond and wherein $R_5$ and $R_7$ form a five membered ring wherein $R_5$, is oxygen, or any combination thereof; $R_8$ independently is hydrogen or $OR_{11}$ wherein $R_{11}$ independently is hydrogen or lower alkyl, or any combination thereof; and X is carbon or nitrogen, and wherein, when X is carbon, $R_6$ is carbon and X and $R_6$ are joined by a carbon-carbon bond; or any combination of the R groups above thereof. Thus, it will be readily apparent to one of ordinary skill in the art that any substituent of the R groups described above can be selected in any combination or sub-combination.

In specific embodiments, the compound is not daidzein, glycinol, glyceollin I, or glyceollin II.

In some embodiments, $R_2$ taken together with $R_3$ form a five membered aromatic ring. In some embodiments, $R_2$ taken together with $R_3$ form a six membered ring, which may include a carbon-carbon double bond, for example a carbon-carbon double bond that includes $R_2$. One of ordinary skill in the art will appreciate that when $R_2$ taken together with $R_3$ form a ring, that $R_3$ is not available to form a ring with $R_4$.

In some embodiments, $R_4$ taken together with $R_3$ form a five membered aromatic ring. In some embodiments, $R_4$ taken together with $R_3$ form a six membered ring, which may include a carbon-carbon double bond, for example a carbon-carbon double bond that includes $R_2$. One of ordinary skill in the art will appreciate that when $R_4$ taken together with $R_3$ form a ring, that $R_3$ is not available to form a ring with $R_2$.

In some embodiments, wherein $R_2$ is part of the ring structure the ring is substituted at $R_2$ with one or more methyl groups.

In some embodiments, $R_4$ is hydrogen.
In some embodiments, $R_2$ is hydrogen.
In some embodiments, $R_6$ is methyl.
In some embodiments, X is carbon.
In some embodiments, X is carbon, $R_6$ is carbon and X and $R_6$ are joined by a carbon-carbon bond (see for example Formulas V VII and VIII), which can be a single or double bond.

In some embodiments, $R_5$ is oxygen, for example a single or double bonded oxygen. In the situation in which the bond is a single bond, it is envisioned that the other substituent bonded to the carbon is hydrogen.

In some embodiments, $R_5$ is two hydrogens, each bonded individually to the carbon.

In some embodiments, $R_9$ is n-Propyl, i-Propyl, n-Butyl, or i-Butyl.

In some embodiments, $R_9$ is hydrogen.
In particular disclosed embodiments, a disclosed daidzein derivative and/or analogue has the formula illustrated below:

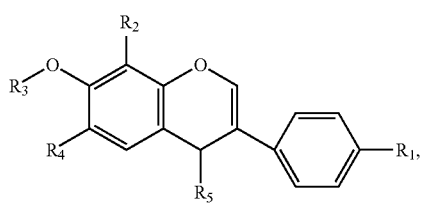

Formula II wherein the R groups are defined as above with respect to Formula I.

In particular disclosed embodiments, a disclosed daidzein derivative and/or analogue has the formula illustrated below:

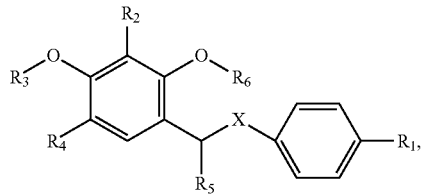

Formula III wherein the R groups are defined as above with respect to Formula I.

In particular disclosed embodiments, a disclosed daidzein derivative and/or analogue has the formula illustrated below:

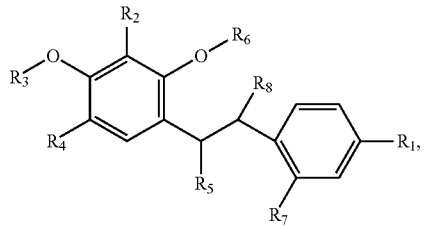

Formula IV wherein the R groups are defined as above with respect to Formula I.

In particular disclosed embodiments, a disclosed daidzein derivative and/or analogue has the formula illustrated below:

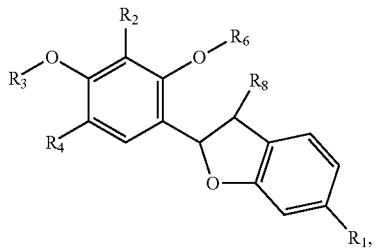

Formula V wherein the R groups are defined as above with respect to Formula I.

In particular disclosed embodiments, a disclosed daidzein derivative and/or analogue has the formula illustrated below:

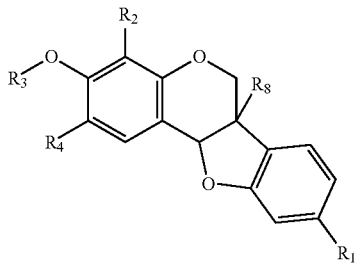

Formula VI wherein the R groups are defined as above with respect to Formula I.

In particular disclosed embodiments, a disclosed daidzein derivative and/or analogue has the formula illustrated below:

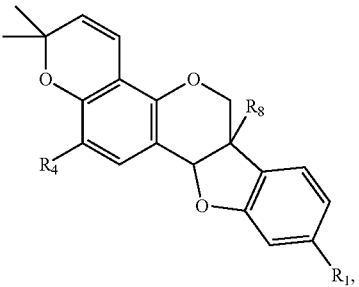

Formula VII wherein the R groups are defined as above with respect to Formula I.

In particular disclosed embodiments, a disclosed daidzein derivative and/or analogue has the formula illustrated below:

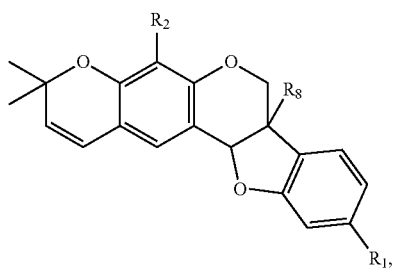

Formula VIII wherein the R groups are defined as above with respect to Formula I.

In specific examples a disclosed daidzein derivative and/or analogue is selected from one of 3-(4-Hydroxyphenyl)-7-isopropoxy-4H-chromen-4-one, 7-Butoxy-3-(4-hydroxyphenyl)-4H-chromen-4-one, 3-(4-Hydroxyphenyl)-7-isobutoxy-4H-chromen-4-one, 7-Hexyloxy-3-(4-hydroxyphenyl)-4H-chromen-4-one, 7-(Allyloxy)-3-(4-hydroxyphenyl)-4H-chromen-4-one, 4-(8,8-Dimethyl-2,3,4,8-tetrahydropyrano[3,2-g]chromen-3-yl)phenol, 2,4-Dimethoxy-N-(4-methoxyphenyl)benzamide, 3-(4-Hydroxyphenyl)-7-methoxy-4H-chromen-4-one, 7-Ethoxy-3-(4-hydroxyphenyl)-4H-chromen-4-one, 7-Cyclopentyloxy-3-(4-hydroxyphenyl)-4H-chromen-4-one, 3-(4-Hydroxyphenyl)-8,8-dimethyl-2,3,9,10-tetrahydropyrano[2,3-f]chromen-4(8H)-one, 3-(4-Hydroxyphenyl)-7-(prop-2-yn-1-yloxy)-4H-chromen-4-one, 3-(4-Hydroxyphenyl)-8-methyl-4H-furo[2,3-h]chromen-4-one, 3-(4-Hydroxyphenyl)-7-propoxy-4H-chromen-4-one, 3-(4-Hydroxyphenyl)-7-(2-(piperidin-1-yl)ethoxy)-4H-chromen-4-one, or N-(4-Hydroxyphenyl)-2,4-dimethoxybenzamide.

"Solvate" means a physical association of a compound with one or more solvent molecules. This physical association involves varying degrees of ionic and covalent bonding, including by way of example covalent adducts and hydrogen bonded solvates. In certain instances the solvate will be capable of isolation, for example when one or more solvent molecules are incorporated in the crystal lattice of the crystalline solid. "Solvate" encompasses both solution-phase and isolable solvates. Representative solvates include ethanol associated compound, methanol associated compounds, and the like. "Hydrate" is a solvate wherein the solvent molecule(s) is/are $H_2O$.

The disclosed compounds also encompass salts including, if several salt-forming groups are present, mixed salts and/or internal salts. The salts are generally pharmaceutically-acceptable salts that are non-toxic. Salts may be of any type (both organic and inorganic), such as fumarates, hydrobromides, hydrochlorides, sulfates and phosphates. In an example, salts include non-metals (e.g., halogens) that form group VII in the periodic table of elements. For example, compounds may be provided as a hydrobromide salt.

Additional examples of salt-forming groups include, but are not limited to, a carboxyl group, a phosphonic acid group or a boronic acid group, that can form salts with suitable bases. These salts can include, for example, nontoxic metal cations which are derived from metals of groups IA, IB, IIA and IIB of the periodic table of the elements. In one embodiment, alkali metal cations such as lithium, sodium or potassium ions, or alkaline earth metal cations such as magnesium or calcium ions can be used. The salt can also be a zinc or an ammonium cation. The salt can also be formed with suitable organic amines, such as unsubstituted or hydroxyl-substituted mono-, di- or tri-alkylamines, in particular mono-, di- or tri-alkylamines, or with quaternary ammonium compounds, for example with N-methyl-N-ethylamine, diethylamine, triethylamine, mono-, bis- or tris-(2-hydroxy-lower alkyl)amines, such as mono-, bis- or tris-(2-hydroxyethyl)amine, 2-hydroxy-tert-butylamine or tris (hydroxymethyl)methylamine, N,N-di-lower alkyl-N-(hydroxy-lower alkyl)amines, such as N,N-dimethyl-N-(2-hydroxyethyl)amine or tri-(2-hydroxyethyl)amine, or N-methyl-D-glucamine, or quaternary ammonium compounds such as tetrabutylammonium salts.

Additional counterions for forming pharmaceutically acceptable salts are found in *Remington's Pharmaceutical Sciences*, 22th Edition, Pharmaceutical Publishing, 2012. In one aspect, employing a pharmaceutically acceptable salt may also serve to adjust the osmotic pressure of a composition.

In certain embodiments the compounds used in the method are provided are polymorphous. As such, the compounds can be provided in two or more physical forms, such as different crystal forms, crystalline, liquid crystalline or non-crystalline (amorphous) forms.

C. Use for the Manufacture of a Medicament

Any of the above described compounds (e.g., daidzein analogues or a hydrate or pharmaceutically acceptable salt thereof) or combinations thereof are intended for use in the manufacture of a medicament for the treatment of a bone defect, such as osteoporosis and/or a bone fracture and/or for stimulating bone growth in a subject. Formulations suitable for such medicaments, subjects who may benefit from same and other related features are described elsewhere herein.

D. Methods of Synthesis

The disclosed daidzein analogues can be synthesized by any method known in the art. Many general references providing commonly known chemical synthetic schemes and conditions useful for synthesizing the disclosed compounds are available (see, e.g., Smith and March, *March's Advanced Organic Chemistry: Reactions, Mechanisms, and Structure*, Fifth Edition, Wiley-Interscience, 2001; or Vogel, *A Textbook of Practical Organic Chemistry, Including Qualitative Organic Analysis*, Fourth Edition, New York: Longman, 1978).

Compounds as described herein may be purified by any of the means known in the art, including chromatographic means, such as HPLC, preparative thin layer chromatography, flash column chromatography and ion exchange chromatography. Any suitable stationary phase can be used, including normal and reversed phases as well as ionic resins. Most typically the disclosed compounds are purified via open column chromatography or prep chromatography.

Suitable exemplary syntheses of daidzein analogues are provided in the Examples below (see e.g. Example 1):

E. Pharmaceutical Compositions

The disclosed daidzein analogues can be useful, at least, for the preventing or treating of a bone defect, such as bone disease or bone injury in a subject, for example a subject that has or is believed to have osteopenia, osteoporosis and/or a bone fracture and/or for stimulating bone growth in a subject. Accordingly, compositions, such as pharmaceutical compositions, comprising at least one disclosed daidzein analogue are also described herein.

Formulations for pharmaceutical compositions are well known in the art. For example, *Remington's Pharmaceutical Sciences*, by E. W. Martin, Pharmaceutical Publishing, 22nd Edition, 2012, describes exemplary formulations (and components thereof) suitable for pharmaceutical delivery of a daidzein analogue. Pharmaceutical compositions comprising at least one of these compounds can be formulated for use in human or veterinary medicine. Particular formulations of a disclosed pharmaceutical composition may depend, for example, on the mode of administration (e.g., oral or parenteral) and/or on the disorder to be treated (e.g., osteoporosis and/or a bone fracture). In some embodiments, formulations include a pharmaceutically acceptable carrier in addition to at least one active ingredient, such as a disclosed daidzein analogue.

Pharmaceutically acceptable carriers useful for the disclosed methods and compositions are conventional in the art. The nature of a pharmaceutical carrier will depend on the particular mode of administration being employed. For example, parenteral formulations usually comprise injectable fluids that include pharmaceutically and physiologically acceptable fluids such as water, physiological saline, balanced salt solutions, aqueous dextrose, glycerol or the like as a vehicle. For solid compositions such as powder, pill, tablet, or capsule forms conventional non-toxic solid carriers can include, for example, pharmaceutical grades of mannitol, lactose, starch, or magnesium stearate. In addition to biologically neutral carriers, pharmaceutical compositions to be administered can optionally contain minor amounts of non-toxic auxiliary substances or excipients, such as wetting or emulsifying agents, preservatives, and pH buffering agents and the like; for example, sodium acetate or sorbitan monolaurate. Other non-limiting excipients include, nonionic solubilizers, such as cremophor, or proteins, such as human serum albumin or plasma preparations.

The disclosed pharmaceutical compositions may be formulated as a pharmaceutically acceptable salt. Lists of other suitable pharmaceutically acceptable salts are found in *Remington's Pharmaceutical Sciences*, $22^{nd}$ Edition, Pharmaceutical Press, London UK, 2112. A pharmaceutically acceptable salt may also serve to adjust the osmotic pressure of the composition.

The dosage form of a disclosed pharmaceutical composition will be determined by the mode of administration chosen. For example, in addition to injectable fluids, oral dosage forms may be employed. Oral formulations may be liquid such as syrups, solutions or suspensions or solid such as powders, pills, tablets, or capsules. Methods of preparing such dosage forms are known, or will be apparent, to those skilled in the art.

Certain embodiments of the pharmaceutical compositions comprising a disclosed compound may be formulated in unit dosage form suitable for individual administration of precise dosages. The amount of active ingredient such as a daidzein analogue administered will depend on the subject being treated, the severity of the disorder, and the manner of administration, and is known to those skilled in the art. Within these bounds, the formulation to be administered will contain a quantity of the extracts or compounds disclosed herein in an amount effective to achieve the desired effect in the subject being treated.

In particular examples, for oral administration the compositions are provided in the form of a tablet containing from about 1.0 to about 50 mg of the active ingredient, particularly about 2.0 mg, about 2.5 mg, 5 mg, about 10 mg, or about 50 mg of the active ingredient for the symptomatic adjustment of the dosage to the subject being treated. In one exemplary oral dosage regimen, a tablet containing from about 1 mg to about 50 mg (such as about 2 mg to about 10 mg) active ingredient is administered two to four times a day, such as two times, three times or four times.

In other examples, a suitable dose for parental administration is about 1 milligram per kilogram (mg/kg) to about 100 mg/kg, such as a dose of about 10 mg/kg to about 80 mg/kg, such including about 1 mg/kg, about 2 mg/kg, about 5 mg/kg, about 20 mg/kg, about 30 mg/kg, about 40 mg/kg, about 50 mg/kg, about 80 mg/kg or about 100 mg/kg administered parenterally. However, other higher or lower dosages also could be used, such as from about 0.001 mg/kg to about 1 g/kg, such as about 0.1 to about 500 mg/kg, including about 0.5 mg/kg to about 200 mg/kg.

Single or multiple administrations of the composition comprising one or more of the disclosed compositions can be carried out with dose levels and pattern being selected by the treating physician. Generally, multiple doses are administered. In a particular example, the composition is administered parenterally once per day. However, the composition can be administered twice per day, three times per day, four times per day, six times per day, every other day, twice a week, weekly, or monthly. Treatment will typically continue for at least a month, more often for two or three months, sometimes for six months or a year, and may even continue indefinitely, i.e., chronically. Repeat courses of treatment are also possible.

In some embodiments, a composition, such as a pharmaceutical composition includes mesenchymal stem cells, such as those described herein, for example BMSCs or ASCs. Methods of obtaining mesenchymal stem cells are known in the art and exemplary methods are given in the examples below. In some examples, the mesenchymal stem cells have been pretreated with a compound to increase the osteogenic potential of mesenchymal stem cells prior to administration. In some embodiments, the mesenchymal stem cells are pretreated with one or more of a disclosed daidzein analogue, daidzein, glycinol, glyceollin I, or glyceollin II.

In some embodiments, compositions and methods disclosed herein utilize mesenchymal stem cells. The mesenchymal stem cells are stem cells, such as adult stem cells, that have the capacity to generate a fully differentiated cell of more than one given cell type. However, mesenchymal stem cells do not have the capacity to generate all fully differentiated cell types of an animal; they are not totipotent, as are embryonic stem cells. Mesenchymal stem cells are present in low numbers in post-natal animals, such as immature, adolescent, or adult animals, such as mice or humans. These multipotent stem cells can be purified from a tissue and induced to differentiate into a variety of fully differentiated cell types, depending on the source of the mesenchymal stem cells and the conditions the stem cell is exposed to.

Mesenchymal stem cells can be obtained from bone marrow, for example, at sites such as the iliac crest, femora, tibiae, spine, rib or other medullary spaces. Other sources of mesenchymal stem cells include placenta, umbilical cord, periosteum, skin, and blood. Mesenchymal stem cells, such as mesenchymal stem cells from bone marrow, have the potential to differentiate into multiple cell types, such as osteoblasts, adipocytes, and chondrocytes (see e.g. Phinney and Prockop, *Stem Cells* 25:2896-2902, 2007; Chamberlain et al., *Stem Cells* 25:2739-2749, 2007). In particular examples, mesenchymal stem cells are obtained from bone marrow. Autologous or allogeneic mesenchymal stem cells may be used in the methods provided herein. In a preferred example, the mesenchymal stem cells are autologous to a subject in need of bone repair.

Mesenchymal stem cells can also be obtained from adipose tissue (such as subcutaneous white adipose, for example adipose tissue from abdomen, breast, thigh, or arm). These cells are referred to as processed lipoaspirate cells (see Zuk et al., *Mol. Biol. Cell* 13:4279-4295, 2002) or adipose-derived stem cells (ASCs) (see Gimble et al., *Circ. Res.* 100:1249-1260, 2007). ASCs have the potential to differentiate into multiple cell types, including adipocytes, chondrocytes, osteoblasts, and neuronal-like cells. Methods of isolating ASCs are known to one of skill in the art, for example from a pelleted stromal vascular fraction prepared from lipoaspirate. See, e.g. Gimble et al., *Circ. Res.* 100: 1249-1260, 2007. Autologous or allogeneic ASCs may be used in the methods provided herein. In a preferred example, the ASCs are autologous to a subject in need of bone repair.

In one embodiment, the pharmaceutical composition is administered without concurrent administration of a second agent for the treatment of osteoporosis and/or a bone fracture and/or for stimulating bone growth. In one specific, non-limiting example, one or more of the disclosed compositions is administered without concurrent administration of other agents, such as without concurrent administration of an additional agent also known to target osteoporosis and/or a bone fracture and/or for stimulating bone growth. In other specific non-limiting examples, a therapeutically effective amount of a disclosed pharmaceutical composition is administered concurrently with an additional agent, including an additional therapy targeting osteoporosis and/or a bone fracture and/or for stimulating bone growth.

Also disclosed is composition for the treatment of any bone disease or bone injury, comprising an isolated mesenchymal stem cell, such as a BMSC or ASC, that has been altered by treatment with the compound of any one of claims 1-21, daidzein, glycinol, glyceollin I, or glyceollin II.

F. Methods of Use

The present disclosure includes methods of treating disorders including preventing or inhibiting one or more signs or symptoms associated with a bone defect, such as a bone disease or bone injury in a subject. In some examples, the bone disease or bone injury in the subject is osteopenia or osteoporosis. In some examples, the bone disease or bone injury in the subject is a bone fracture. Also disclosed are methods of stimulating bone growth in a subject, for example a subject with osteoporosis and/or a bone fracture.

Disclosed methods include administering one of more disclosed daidzein analogue (and, optionally, one or more other pharmaceutical agents, such as mesenchymal stem cells) to a subject in a pharmaceutically acceptable carrier and in an amount effective to treat the bone defect, such as bone disease or bone injury in the subject, for example osteoporosis and/or a bone fracture or for the stimulation of bone growth in the subject. Treatment includes preventing or reducing signs or symptoms associated with the bone defect, for example, by reducing or slowing the loss of bone density in a subject with osteoporosis or a regrowth or ingrowth of bone at the site of a bone injury, such as a fracture. Such a reduction in bone loss can in some examples be a decrease in bone loss by at least 5%, at least 10%, at least 20%, at least 50%, or at least 75%, for example in a subject with or suspected of having osteoporosis. A regrowth or ingrowth of bone at the site of a bone injury, such as a fracture can in some examples be increase in bone grown by at least 5%, at least 10%, at least 20%, at least 50%, or at least 75%, for example relative to a control. In some examples, mesenchymal stem cells are administered in conjunction with a disclosed daidzein analogue, such as before, during, or after administration of the daidzein analogue. In some examples, the mesenchymal stem cells have been pretreated with a compound to increase the osteogenic potential of mesenchymal stem cells prior to administration. In some embodiments, the mesenchymal stem cells are pretreated with one or more of a disclosed daidzein analogue, daidzein, glycinol, glyceollin I, or glyceollin II. In some examples, the mesenchymal stem cells are administered at the site of the injury or the place in the body, where bone growth or reduction of bone loss is desired, for example by injection or other method, such as on a biocompatible bone repair system.

Routes of administration useful in the disclosed methods include but are not limited to oral and parenteral routes, such as intravenous (iv), intraperitoneal (ip), rectal, topical, ophthalmic, nasal, and transdermal.

An effective amount of one or more daidzein analogues will depend, at least, on the particular method of use, the subject being treated, the severity of the tumor, and the manner of administration of the therapeutic composition. A "therapeutically effective amount" of a composition is a quantity of a specified compound sufficient to achieve a desired effect in a subject being treated. For example, this may be the amount of a disclosed daidzein analogue necessary to prevent or inhibit bone loss and/or stimulate bone growth. Ideally, a therapeutically effective amount of a disclosed daidzein analogue is an amount sufficient to prevent or inhibit bone loss and/or stimulate bone growth without causing a substantial side effect in the subject.

Therapeutically effective doses of a disclosed daidzein analogue or pharmaceutical composition can be determined by one of skill in the art. An example of a dosage range is from about 0.001 to about 10 mg/kg body weight orally in single or divided doses. In particular examples, a dosage range is from about 0.005 to about 5 mg/kg body weight orally in single or divided doses (assuming an average body weight of approximately 70 kg; values adjusted accordingly for persons weighing more or less than average). For oral administration, the compositions are, for example, provided in the form of a tablet containing from about 1.0 to about 50 mg of the active ingredient, particularly about 2.5 mg, about 5 mg, about 10 mg, or about 50 mg of the active ingredient for the symptomatic adjustment of the dosage to the subject being treated. In one exemplary oral dosage regimen, a tablet containing from about 1 mg to about 50 mg active ingredient is administered two to four times a day, such as two times, three times or four times.

In other examples, a suitable dose for parental administration is about 1 milligram per kilogram (mg/kg) to about 100 mg/kg, such as a dose of about 10 mg/kg to about 80 mg/kg, such including about 1 mg/kg, about 2 mg/kg, about 5 mg/kg, about 20 mg/kg, about 30 mg/kg, about 40 mg/kg, about 50 mg/kg, about 80 mg/kg or about 100 mg/kg administered parenterally. However, other higher or lower dosages also could be used, such as from about 0.001 mg/kg to about 1 g/kg, such as about 0.1 to about 500 mg/kg, including about 0.5 mg/kg to about 200 mg/kg.

Single or multiple administrations of the composition comprising one or more of the disclosed compositions can be carried out with dose levels and pattern being selected by the treating physician. Generally, multiple doses are administered. In a particular example, the composition is administered parenterally once per day. However, the composition can be administered twice per day, three times per day, four times per day, six times per day, every other day, twice a week, weekly, or monthly. Treatment will typically continue for at least a month, more often for two or three months, sometimes for six months or a year, and may even continue indefinitely, i.e., chronically. Repeat courses of treatment are also possible.

The specific dose level and frequency of dosage for any particular subject may be varied and will depend upon a variety of factors, including the activity of the specific compound, the metabolic stability and length of action of that compound, the age, body weight, general health, sex and diet of the subject, mode and time of administration, rate of excretion, drug combination, and severity of the condition of the subject undergoing therapy.

Subjects can be screened prior to initiating the disclosed therapies, for example to select a subject in need of reducing bone loss and/or the stimulation of bone growth. Briefly, the method can include screening subjects to determine if they are in need of therapeutic intervention, for example if they have or are suspected of having a bone disease or injury, such as osteoporosis or a bone fracture. Subjects having a bone disease or injury, such as osteoporosis or a bone fracture, are selected. In one example, subjects are diagnosed with a bone disease or injury, such as osteoporosis or a bone fracture, by clinical signs, laboratory tests, or both. For example, with osteoporosis, quantitative computed tomography can be used to assess bone marrow density. For bone fractures, simple x-ray techniques may suffice.

Pre-screening is not required prior to administration of the therapeutic agents disclosed herein (such as those including a disclosed daidzein analogue).

Following the administration of one or more therapies, subjects can be monitored for decreases bone loss or stimulation of bone growth. In particular examples, subjects are analyzed one or more times. Subjects can be monitored using any method known in the art including those described herein including imaging analysis.

In particular examples, if subjects are stable or have a minor, mixed or partial response to treatment, they can be re-treated after re-evaluation with the same schedule and preparation of agents that they previously received for the desired amount of time, including the duration of a subject's lifetime.

In some examples, the method further includes administering a therapeutic effective amount of a disclosed daidzein analogue with additional therapeutic treatments, in particular examples, prior to, during, or following administration of a therapeutic amount of an agent that prevents or inhibits bone loss or stimulates bone growth. In some examples, mesenchymal stem cells are administered in conjunction with a disclosed daidzein analogue, such as before, during, or after administration of the daidzein analogue. In some examples, the mesenchymal stem cells have been pretreated with a compound to increase the osteogenic potential of mesenchymal stem cells prior to administration. In some embodiments, the mesenchymal stem cells are pretreated with one or more of a disclosed daidzein analogue, daidzein, glycinol, glyceollin I, or glyceollin II. In some examples, the mesenchymal stem cells are administered at the site of the injury or the place in the body, where bone growth or reduction of bone loss is desired, for example by injection or other method, such as on a biocompatible bone repair system.

G. Biocompatible Bone Repair System

Also disclosed herein is a biocompatible bone repair system which includes a biocompatible substrate that has been coated with and/or seeded with a disclosed daidzein analogue and/or mesenchymal stem cells, such as a mesenchymal stem cells treated with a disclosed daidzein analogue, daidzein, glycinol, glyceollin I, or glyceollin II. Also provided are methods of treating a bone defect with a disclosed biocompatible bone repair system, which includes surgically implanting the biocompatible substrate at the bone defect site.

In some embodiments, the biocompatible substrate is coated with one or more of a disclosed daidzein analogue, daidzein, glycinol, glyceollin I, and/or glyceollin II. The biocompatible substrate can be partially or completely coated. In a further example, the biocompatible substrate is substantially coated.

It is contemplated that any chemical or mechanical bond or force, including linking agents can be used to coat the biocompatible substrate. For example, a biocompatible substrate composed of a first substance can be "coated" with a second substance (e.g., a disclosed daidzein analogue, daidzein, glycinol, glyceollin I, or glyceollin II) via a linking agent that is a third substance. In a further example, a biocompatible substrate is impregnated with a disclosed daidzein analogue, daidzein, glycinol, glyceollin I, or glyceollin II.

In some embodiments, mesenchymal stem cells are seeded on a biocompatible substrate. Seeding the substrate includes introducing cells to the substrate such that they are in contact with or attached to the substrate. Suitable substrates include for example, a sponge, a strip, a scaffold, a gel, or a three-dimensional implant and may include collagen or gelatin, hyaluronic acid, polymers (such as nylon or polyester), polymer-hyaluronic acid, polymer-bioactive glass, tricalcium phosphate, hydroxyapatite surfaces, or other biologically compatible components or other scaffolds. Methods of seeding the substrate include incubating the substrate with a cell suspension, placing a cell suspension in contact with the substrate and allowing the cells to soak into the substrate, or placing the substrate in contact with a cell suspension and applying a vacuum.

In some examples, a substrate is incubated in a cell suspension (such as cells suspended in a culture medium) for a period of time sufficient for the cells to penetrate or attach to the substrate. The cell suspension may contain about $1 \times 10^3$ to about $1 \times 10^9$ cells, such as about $1 \times 10^5$ to about $1 \times 10^7$ cells, for example, about $2 \times 10^6$ cells. In some examples, the substrate is incubated in a cell suspension for about one day to about ten days, such as about three days to about seven days, for example, about five days or about seven days.

In additional examples, a cell suspension is applied directly to a surface of a substrate and the suspension is allowed to soak into the substrate (for example a sponge). In some examples a cell suspension of about 100,000 cells per mm substrate to about 5 million cells per mm substrate, such as about 500,000 cells per mm substrate to about 3 million cells per mm substrate, or about 1 million cells per mm substrate to about 2 million cells per mm substrate is applied to a surface of a substrate.

In further examples, the substrate is contacted with cells (such as a cell suspension) and a vacuum is applied. In some examples, a vacuum of about 400 mm Hg is applied to draw the cells into the substrate. In other examples, the cells may be drawn into the substrate by gravity.

If the substrate is a non-porous material (such as a non-porous polymer, tricalcium phosphate, hydroxyapatite, or metal), the cells may be plated directly on the surface of the substrate and allowed to attach to the substrate surface.

The seeding of a substrate with cells can be assessed by methods known in the art. In some examples, the substrate is inspected visually for the presence of cells, for example by light microscopy (such as in the case of a transparent substrate). In other examples, the cells can be detected by immunofluorescence (such as by staining for the presence of cell proteins, for example actin). The cells may be attached to the outer surface of the substrate, or in the case of a porous substrate (such as a sponge or hydrogel), the cells may be present in the internal portion of the substrate, such as in the interstitial spaces of the substrate. In other examples, seeding of a substrate with cells can be assessed by staining cells using histological stains (such as hematoxylin and eosin), nucleic acid stains (such as nuclear staining, for example with 4',6-diamidino-2-phenylindole (DAPI) or Hoechst stain), or by immunohistochemistry (for example, by staining for proteins expressed by the cells, such as actin).

In some examples, following seeding of mesenchymal stem cells on a biocompatible substrate including the substrate and cells are cultured for an additional period of time, such that the number of cells on the substrate increases, for example, until the cells reach confluency. In other examples, the substrate and cells are cultured for a pre-determined period of time, such as about 1 day to about 20 days, such as about 3 days to about 15 days, about 5 days to about 10 days, or about 7 days. In some examples, the substrate containing the cells is cultured in medium containing a disclosed daidzein analogue, daidzein, glycinol, glyceollin I, or glyceollin II.

In some examples, culture of the mesenchymal stem cells following seeding on a biocompatible substrate is carried out using standard cell culture techniques, such as in a cell culture flask, dish, or multi-well plate. The culture conditions are those appropriate for the particular cells in culture, for example, culture at about 37° C. in a humidified atmosphere of about 5% $CO_2$.

In some embodiments, the methods and compositions described herein include the use of a biocompatible substrate, which is a component of a biocompatible transplantable bone repair system. In some embodiments, the biocompatible transplantable bone repair system is coated and/or seeded with one or more disclosed daidzein analogues and/or mesenchymal stem cells, such as mesenchymal stem cells that have been pretreated with a disclosed daidzein analogue, daidzein, glycinol, glyceollin I, or glyceollin II. In some examples, the biologically compatible substrate is surgically implanted in a subject at the site of a bone defect in order to treat the bone defect.

The biocompatible substrate may include one or more proteins (such as collagen, for example, collagen type I or gelatin), polymers (for example, nylon or polyester), polymer-hyaluronic acid, polymer-bioactive glass, tricalcium phosphate, hyaluronic acid surfaces, hydroxyapatite, or mixtures thereof. In some examples, the substrate may be a fabric, such as nylon, silk, or DACRON® polyester (e.g., Barros D'Sa et al., *Ann. Surg.* 192:645-657, 1980). In other examples, the substrate may include metal, such as titanium.

The biologically compatible substrate may be in the form of a scaffold or other supporting structure, such as a sponge, strip, gel (such as a hydrogel), scaffold, or other three-dimensional structure. In one example, the substrate is a sponge. In a particular example, the biologically compatible substrate is a collagen or gelatin sponge (such as GELFOAM® (Pfizer, New York, N.Y.) or SURGIFOAM® (Johnson & Johnson, New Brunswick, N.J.)). In another particular example, the biologically compatible substrate is a nylon strip.

The substrate is generally a three-dimensional shape, such as a cube, rectangular block, triangle, wedge, or other appropriate shape. In particular examples, the substrate is shaped to fit the particular bone defect which is to be repaired. The substrate may also be essentially two-dimensional, such as a strip. The biocompatible substrate is of a size and shape suitable for repair of a particular bone defect in a subject. For example, a three-dimensional substrate may have dimensions of about 1 $mm^3$ to about 50 $mm^3$, such as about 2 $mm^3$ to about 25 $mm^3$, such as about 5 $mm^3$ to about 10 $mm^3$. In some examples, the substrate has dimensions of about 0.5 inches by 0.25 inches to about 1 inch by 1 inch. However, one of skill in the art will recognize that the dimensions of the substrate are determined by the dimensions of the bone defect which is to be repaired. In additional examples, the transplantable bone repair system can be prepared in dimensions that are larger than the bone defect and cut to the appropriate size prior to implanting in the defect.

Biocompatible substrates are well known in the art (see, e.g. U.S. Pat. Nos. 5,700,289 and 6,541,024). Examples of a biocompatible substrate include biodegradable and biocompatible polymer scaffolds (see Jang et al., *Expert Rev. Medical Devices* 1:127-138, 2004). These scaffolds usually contain a mixture of one or more biodegradable polymers, for example and without limitation, saturated aliphatic polyesters, such as poly(lactic acid) (PLA), poly(glycolic acid), or poly(lactic-co-glycolide) (PLGA) copolymers, unsaturated linear polyesters, such as polypropylene fumarate (PPF), or microorganism produced aliphatic polyesters, such as polyhydroxyalkanoates (PHA) (see Rezwan et al., *Biomaterials* 27:3413-3431, 2006; Laurencin et al., *Clin. Orthopaed. Rel. Res.* 447:221-236). By varying the proportion of the various components, polymeric scaffolds of different mechanical properties are obtained. A commonly used scaffold contains a ratio of PLA to PGA of about 75:25, but this ratio may change depending upon the specific application. Other commonly used scaffolds include surface bioeroding polymers, such as poly(anhydrides), such as trimellitylimidoglycine (TMA-gly) or pyromellitylimidoalanine (PMA-ala), or poly(phosphazenes), such as high molecular weight poly(organophosphazenes) (P[PHOS]), and bioactive ceramics.

Another class of materials for making a substrate is hydroxyapatite, or a ceramic formed of tricalcium phosphate (TCP) or calcium phosphate ($CaPO_4$). Calcium hydroxyapatites occur naturally as geological deposits and in normal biological tissues, principally bone, cartilage, enamel, dentin, and cementum of vertebrates and in many sites of pathological calcifications such as blood vessels and skin. Synthetic calcium hydroxyapatite is formed in the laboratory either as pure $Ca_{10}(PO_4)_6(OH)_2$ or hydroxyapatite that is impure, containing other ions such as carbonate, fluoride, chloride for example, or crystals deficient in calcium or crystals in which calcium is partly or completely replaced by other ions such as barium, strontium and lead.

Calcium phosphate ceramics can be used as implants in the repair of bone defects because these materials are non-toxic, non-immunogenic, and are composed of calcium and phosphate ions, the main constituents of bone. Both tricalcium phosphate (TCP) $[Ca_3(PO_4)_2]$ and hydroxyapatite $[Ca_{10}(PO_4)_6(OH)_2]$ have been widely used. Calcium phosphate implants are osteoconductive, and have the apparent ability to become directly bonded to bone.

In other examples, polymers that can form ionic hydrogels which are malleable can also be used as a biocompatible substrate. A hydrogel may be utilized to deliver cells and promote the formation of new tissue without the use of any other substrate. In one example, the hydrogel is produced by cross-linking the ionic salt of a polymer with ions, whose strength increases with either increasing concentrations of ions or polymer. A hydrogel is defined as a substance formed when an organic polymer (natural or synthetic) is cross-linked via covalent, ionic, or hydrogen bonds to create a three-dimensional open-lattice structure which entraps water molecules to form a gel. Examples of materials which can be used to form a hydrogel include polysaccharides such as alginate, polyphosphazenes, and polyacrylates such as hydroxyethyl methacrylate, which are crosslinked ionically, or block copolymers such as PLURONICS™ (BASF Corporation) or TETRONICS™ (BASF Corporation), polyethylene oxide-polypropylene glycol block copolymers which are crosslinked by temperature or pH, respectively. Other materials include proteins such as fibrin, polymers such as polyvinylpyrrolidone, hyaluronic acid and collagen.

The biologically compatible substrate may also include gelatin, cellulose, or collagen-based materials. In some examples, the gelatin-based substrate includes an absorbable sponge, powder or film of cross-linked gelatin, for example, GELFOAM® (Upjohn, Inc., Kalamazoo, Mich.) which is formed from denatured collagen. A cellulose-based substrate includes an appropriate absorbable cellulose such as regenerated oxidized cellulose sheet material, for example, SURGICEL® (Johnson & Johnson, New Brunswick, N.J.) or Oxycel® (Becton Dickinson, Franklin Lakes, N.J.). A biologically compatible collagen-based substrate includes an appropriate resorbable collagen, such as purified bovine corium collagen, for example, AVITENE® (MedChem, Woburn, Mass.), HELISTAT® (Marion Merrell Dow, Kansas City, Mo.), HEMOTENE® (Astra, Westborough, Mass.), or SURGIFOAM® (Johnson & Johnson, New Brunswick, N.J.).

Methods are provided to treat bone defects utilizing the biocompatible transplantable bone repair system described herein. The methods include preparing a biocompatible transplantable bone repair system as described above. The bone repair system is surgically implanted at the site of a bone defect in order to treat the bone defect. In some examples, the bone repair system is sized to fit the defect to be repaired. In particular examples, the bone repair system is cemented in place (such as with hyaluronic acid or superglue), for example in a bone defect in the skull, for example a craniotomy or other skull fracture. In other examples, the bone repair system is fastened in place, such as with metal or plastic screws. In some examples, the substrate includes fabric (such as nylon, silk, or DACRON®) which may be stretched across a fracture or placed inside a defect as multiple layers (for example, in a large fracture or a non-union fracture). The methods can be used in human or non-human subjects.

In some embodiments, the biocompatible transplantable bone repair device disclosed herein is used to treat subjects that have a bone defect due to any disease, defect, or disorder which affects bone strength, function, and/or integrity, such as decreasing bone tensile strength and modulus. Examples of bone diseases include, but are not limited to, diseases of bone fragility, such as osteoporosis or osteopenia. Other examples include bone defects in a subject affected with malignancies and/or cancers of the bone such as a sarcoma, such as osteosarcoma.

Assays to determine if a transplanted bone repair device treats the bone defect are known in the art. Non-limiting examples of suitable assays include radiographic methods (Lehmann et al., *Bone* 35: 1247-1255, 2004; Rundle et al., *Bone* 32: 591-601, 2003; Nakamura et al., *J. Bone Miner. Res.* 13: 942-949, 1998); microcomputed tomography (μCT) methods (Nakamura et al., *J. Bone Miner. Res.* 13: 942-949, 1998; Lehmann et al., *Bone* 35: 1247-1255, 2004; Tamasi et al., *J. Bone Miner. Res.* 18: 1605-1611, 2003; Shefelbine et al., *Bone* 36:480-488, 2005); peripheral quantitative computed tomographic methods (Rundle et al., *Bone* 32: 591-601, 2003; Tamasi et al., *J. Bone Miner. Res.* 18: 1605-1611, 2003); dual energy X-ray absorptiometry methods (Holzer et al., *Clin. Orthop. Rel. Res.* 366: 258-263, 1999; Nakamura et al., *J. Bone Miner. Res.* 13: 42-949, 1998); histomorphometry methods (Lehmann et al., *Bone* 35: 247-1255, 2004; Tamasi et al., *J. Bone Miner. Res.* 18:1605-1611, 2003; Li et al., *J. Bone Miner. Res.* 17: 791-799, 2002; Schmidmaier et al., *Bone* 30: 816-822; 2002; Nakamura et al., *J. Bone Miner. Res.* 13:942-949, 1998; Sheng et al., *Bone* 30: 486-491, 2002); Masson's trichrome stain for collagen (Rundle et al., *Bone* 32: 591-601, 2003); Goldner's stain for collagen (Holzer et al., *Clin. Orthop. Rel. Res.* 366: 258-263; 1999); Von Kossa's silver stain for bone (Schmidmaier et al., *Bone* 30: 816-822, 2002); Safranin Orange stain for collagen (Schmidmaier et al., *Bone* 30: 816-822, 2002); and immunohistochemistry methods (Rundle et al., *Bone* 32: 591-601, 2003; Li et al., *J. Bone Miner. Res.* 17: 791-799, 2002; Safadi et al., *J. Cell Physiol.* 196: 51-62, 2003; Iwaki et al., *J. Bone Miner. Res.* 12: 96-102, 1997).

Treating a bone defect includes stimulation of new bone formation which is sufficient to at least partially fill a void or structural discontinuity at the site of a bone defect. Treatment of the bone defect does not require a process of complete healing or a treatment which is 100% effective at restoring a defect to its pre-defect state. Successful treatment of a bone defect includes partial repair or healing, for example filling of at least 10%, at least 20%, at least 30%, at least 40%, at least 50%, at least 60%, at least 70%, at least 80%, at least 90%, at least 95%, or at least 99% of the bone defect with new bone material.

H. Exemplary Bone Defects

The bone defect can be a fracture, such as a critical defect or non-union fracture. A fracture is a condition in which a bone is cracked or broken; a break in the continuity of a bone. Fractures may be classified as closed (such as when the skin is intact) or open (exposed to the air, such as piercing the skin or due to severe tissue injury). Fractures are also classified as simple or multi-fragmentary. A simple fracture occurs along only one line (such as splitting a bone into two pieces), while a multi-fragmentary (or comminuted) fracture splits a bone into multiple pieces (such as three or more pieces). Other types of fracture include complete (such as when bone fragments are completely separated), incomplete (such as when bone fragments are at least partially in contact), linear (such as a fracture parallel to the long axis of a bone), transverse (such as a fracture at right angles to the long axis of a bone), oblique (such as a fracture diagonal to the long axis of a bone), compression (such as collapse of a vertebrae, for example as a result of osteoporosis), spiral (such as when at least one portion of the fractured bone is twisted), and compacted (such as a fracture resulting from bone fragments being driven into one another). In children, fractures also include greenstick fractures (such as a fracture in which the bone does not completely fracture, but exhibits bowing without complete disruption of the cortex of the bone). In particular examples, fractures include a critical defect (such as when part of a bone is lost or removed) and a non-union fracture (such as when the ends of the fracture are not in contact with each other).

The defect or fracture can be in any bone, including but not limited to bones of the skull, such as cranial bones such as the frontal bone, parietal bone, temporal bone, occipital bone, sphenoid bone, ethmoid bone; facial bones such as the zygomatic bone, superior and inferior maxilla, nasal bone, mandible, palatine bone, lacrimal bone, vomer bone, the inferior nasal conchae; the bones of the ear, such as the malleus, incus, stapes; the hyoid bone; the bones of the shoulder, such as the clavicle or scapula; the bones of the thorax, such as the sternum or the ribs; the bones of the spinal column including the cervical vertebrae, lumbar vertebrae, and thoracic vertebrae; the bones of the arm, including the humerus, ulna and radius; the bones of the hands, including the scaphoid, lunate, triquetrum bone, pisiform bone, trapezium bone, trapezoid bone, capitate bone, and hamate bone; the bones of the palm such as the metacarpal bones; the bones of the fingers such as the proximal, intermediate and distal phalanges; the bones of the pelvis such as the ilium, sacrum and coccyx; the bones of the legs, such as the femur, tibia, patella, and fibula; the bones of the feet, such as the calcaneus, talus, navicular bone, medial cuneiform bone, intermediate cuneiform bone, lateral cuneiform bone, cuboidal bone, metatarsal bone, proximal phalanges, intermediate phalanges and the distal phalanges; and the pelvic bones. In one example, a bone fracture is repaired in the absence of extra-skeletal bone formation, such as in the absence of bone formation in the soft tissues.

Methods are also provided to treat bone defects by promoting spinal fusion. Spinal fusion can be induced in any of the vertebrae, including, but not limited to, the cervical vertebrae, lumbar vertebrae, and thoracic vertebrae. In one example, spinal fusion occurs in the absence of extra-skeletal bone formation, such as in the absence of bone formation in the soft tissues. In other examples, methods are provided to treat dental or facial bone defects, such as cleft palate, jaw injuries or defects, and facial fractures.

The natural process of healing a fracture starts when the injured bone and surrounding tissues bleed. The blood coagulates to form a blood clot situated between the broken fragments. Within a few days blood vessels grow into the jelly-like matrix of the blood clot. The new blood vessels bring white blood cells to the area, which gradually remove the non-viable material. The blood vessels also bring fibroblasts in the walls of the vessels and these multiply and produce collagen fibers. In this way the blood clot is replaced by a matrix of collagen.

I. Clinical Trials

To obtain regulatory approval for the use of one or more of the disclosed daidzein analog to treat a bone disorder, clinical trials are performed. As is known in the art, clinical trials progress through phases of testing, which are identified as Phases I, II, III, and IV.

Initially the disclosed daidzein analog is evaluated in a Phase I trial. Typically Phase I trials are used to determine the best mode of administration (for example, by pill or by injection), the frequency of administration, and the toxicity for the compounds. Phase I studies frequently include laboratory tests, such as blood tests and biopsies, to evaluate the effects of the potential therapeutic in the body of the patient. For a Phase I trial, a small group of patients with bone disease or injury are treated with a specific dose of a disclosed daidzein analog. During the trial, the dose is typically increased group by group in order to determine the maximum tolerated dose (MTD) and the dose-limiting toxicities (DLT) associated with the compound. This process determines an appropriate dose to use in a subsequent Phase II trial.

A Phase II trial can be conducted to further evaluate the effectiveness and safety of the disclosed daidzein analog. In Phase II trials, a disclosed daidzein analog is administered to groups of patients with a bone disease or injury using the dosage found to be effective in Phase I trials.

Phase III trials focus on determining how a disclosed daidzein analog compares to the standard, or most widely accepted, treatment. In Phase III trials, patients are randomly assigned to one of two or more "arms". In a trial with two arms, for example, one arm will receive the standard treatment (control group) and the other arm will receive a disclosed daidzein analog treatment (investigational group).

Phase IV trials are used to further evaluate the long-term safety and effectiveness of a disclosed daidzein analog. Phase IV trials are less common than Phase I, II and III trials and take place after a disclosed daidzein analog has been approved for standard use.

Participant eligibility criteria can range from general (for example, age, sex, type of disease) to specific (for example, type and number of prior treatments, disease characteristics, blood cell counts, organ function). In one embodiment, eligible patients have been diagnosed with a bone disease or injury, such as osteopenia or osteoporosis. Eligibility criteria may also vary with trial phase. Patients eligible for clinical trials can also be chosen based on objective measurement of a bone disease or injury and failure to respond to other bone disease or injury treatments. For example, in Phase I and II trials, the criteria often exclude patients who may be at risk from the investigational treatment because of abnormal organ function or other factors. In Phase II and III trials additional criteria are often included regarding disease type and stage, and number and type of prior treatments.

Phase I trials usually include 15 to 30 participants for whom other treatment options have not been effective. Phase II trials typically include up to 100 participants who have already received drug therapy, but for whom the treatment has not been effective.

Participation in Phase III trials is often restricted based on the previous treatment received. Phase III trials usually include hundreds to thousands of participants. This large number of participants is necessary in order to determine whether there are true differences between the effectiveness of a disclosed daidzein analog and the standard treatment. Phase III can include patients ranging from those newly diagnosed with a bone disease or injury to those with re-occurring signs and/or symptoms associated with a bone disease or injury that did not respond to prior treatment.

One skilled in the art will appreciate that clinical trials should be designed to be as inclusive as possible without making the study population too diverse to determine whether the treatment might be as effective on a more narrowly defined population. The more diverse the population included in the trial, the more applicable the results could be to the general population, particularly in Phase III trials. Selection of appropriate participants in each phase of clinical trial is considered to be within the ordinary skills of a worker in the art.

A disclosed daidzein analog is typically administered to the trial participants orally. A range of doses of the agent can be tested. Provided with information from preclinical testing, a skilled practitioner can readily determine appropriate dosages of agent for use in clinical trials. In one embodiment, a dose range is from about 100 µg/kg and about 5000 mg/kg of the subject's weight, such as 1 mg/kg and about 2000 mg/kg of the subject's weight, about 100 mg/kg and about 1500 mg/kg of the subject's weight, about 100 µg/kg and about 2000 mg/kg of the subject's weight, about 200 mg/kg and about 1000 mg/kg of the subject's weight, about 200 mg/kg and about 750 mg/kg of the subject's weight, about 250 mg/kg and about 500 mg/kg of the subject's weight, about 100 µm and about 500 mM.

To fulfill Phase I criteria, distribution of the disclosed daidzein analog is monitored, for example, by chemical analysis of samples, such as blood, collected at regular intervals. For example, samples can be taken at regular intervals up until about 72 hours after the start of treatment.

If analysis is not conducted immediately, the samples can be placed on dry ice after collection and subsequently transported to a freezer to be stored at −70° C. until analysis can be conducted. Samples can be prepared for analysis using standard techniques known in the art and the amount of the disclosed daidzein analog present can be determined, for example, by high-performance liquid chromatography (HPLC). Pharmacokinetic data can be generated and analyzed in collaboration with an expert clinical pharmacologist and used to determine, for example, clearance, half-life and maximum plasma concentration.

The endpoint of a clinical trial is a measurable outcome that indicates the effectiveness of a compound under evaluation. The endpoint is established prior to the commencement of the trial and will vary depending on the type and phase of the clinical trial.

The subject matter of the present disclosure is further illustrated by the following non-limiting Examples.

EXAMPLES

Example 1

Synthesis of Daidzein Analogs

As shown in Scheme 1, selective O-alkylation on the 7-hydroxyl group of daidzein 1 gave derivatives 2a-1 and 6. The derivative 3 was obtained by the reaction of 1 and 1,1-diethoxy-3-methylbut-2-ene in refluxing xylene with picoline as the base compound under microwave irradiation. The introduction of the microwave technique to replace the traditional heating methods significantly shortened the reaction time and improved the yield of the reaction. Further, the hydrogenation of 3 using 10% Pd/C resulted in the formation of derivative 4 or 5 as the major product, respectively, depending on the use of ethyl acetate or methanol as solvent. The derivative 7 was prepared by the successive Claisen rearrangement and cyclization of 6 in refluxing N, N-diethylaniline with CsF as the catalyst under microwave irradiation. Reacting with trifluoromethanesulfonic anhydride, 3 was converted into its triflate which was the starting material for the synthesis of derivative 8 through the PdCl$_2$(dppf)-catalyzed borylation using the diboron reagent in the presence of KOAc. O-Butylation on the 7-hydroxyl group of equol gave the derivative 9. The derivative 10 was obtained by the reaction of equol and 1,1-diethoxy-3-methylbut-2-ene in refluxing xylene with picoline as the base under microwave irradiation.

Scheme 1 Synthesis of daidzein derivatives and analogs.

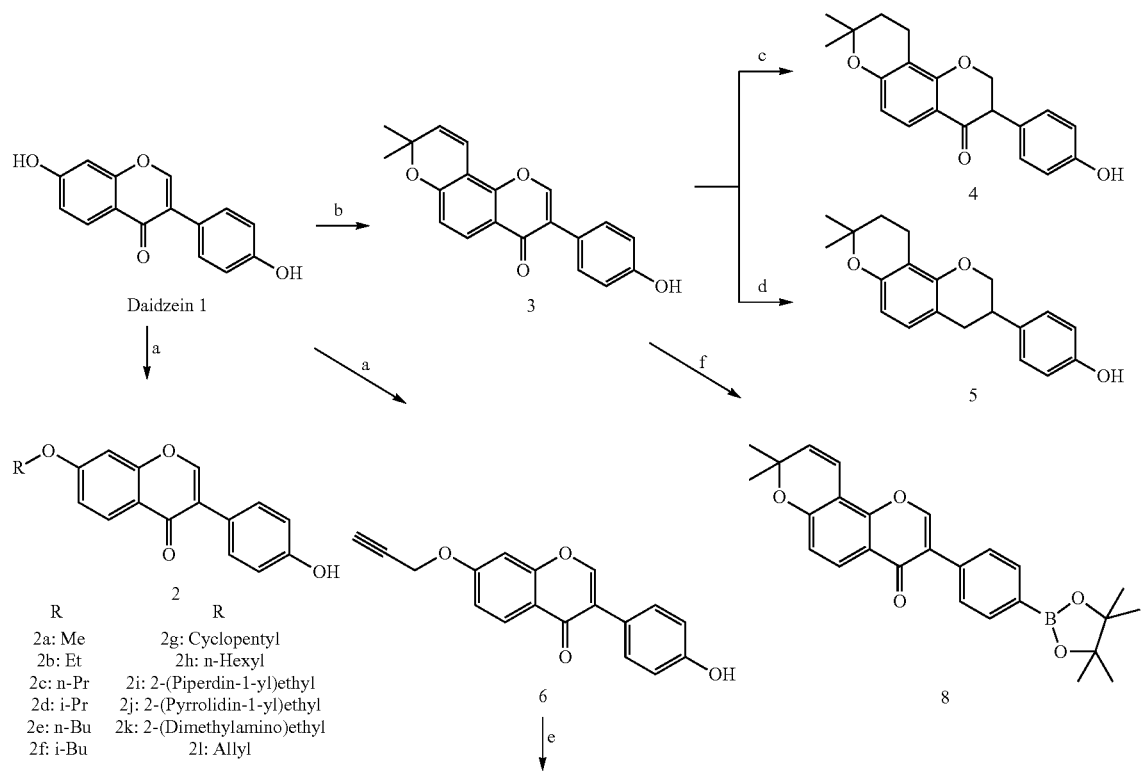

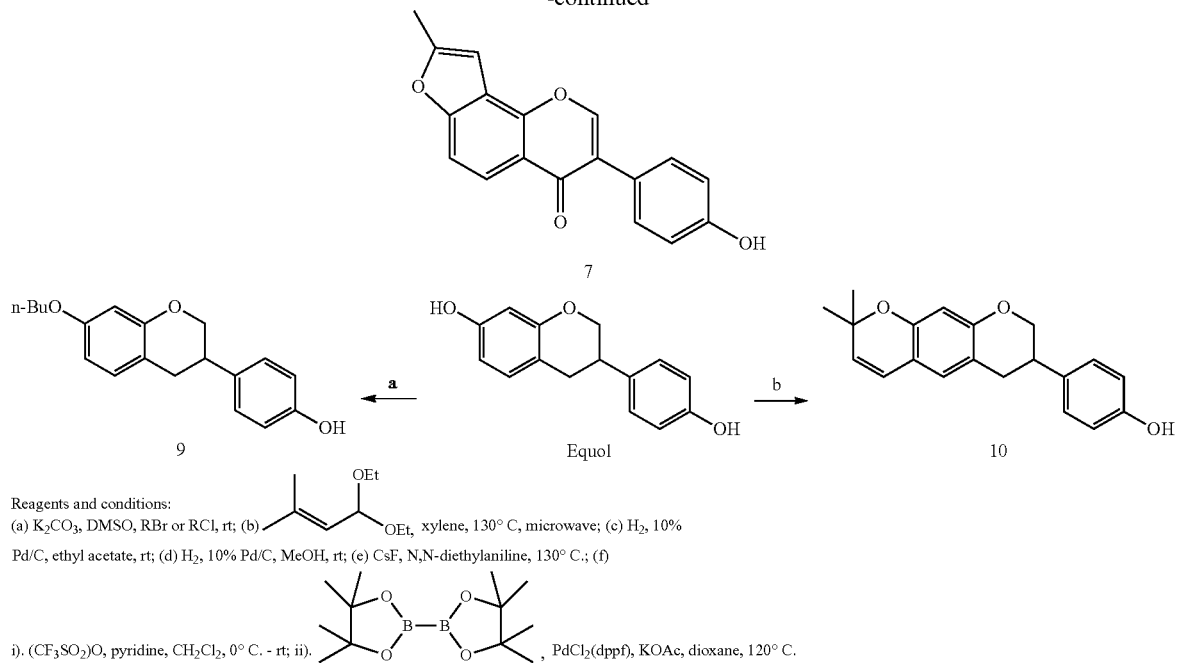

Reagents and conditions:
(a) K₂CO₃, DMSO, RBr or RCl, rt; (b) [structure], xylene, 130° C, microwave; (c) H₂, 10% Pd/C, ethyl acetate, rt; (d) H₂, 10% Pd/C, MeOH, rt; (e) CsF, N,N-diethylaniline, 130° C.; (f) i). (CF₃SO₂)₂O, pyridine, CH₂Cl₂, 0° C. - rt; ii). [structure], PdCl₂(dppf), KOAc, dioxane, 120° C.

Scheme 2. Synthesis of 12a and 12b.

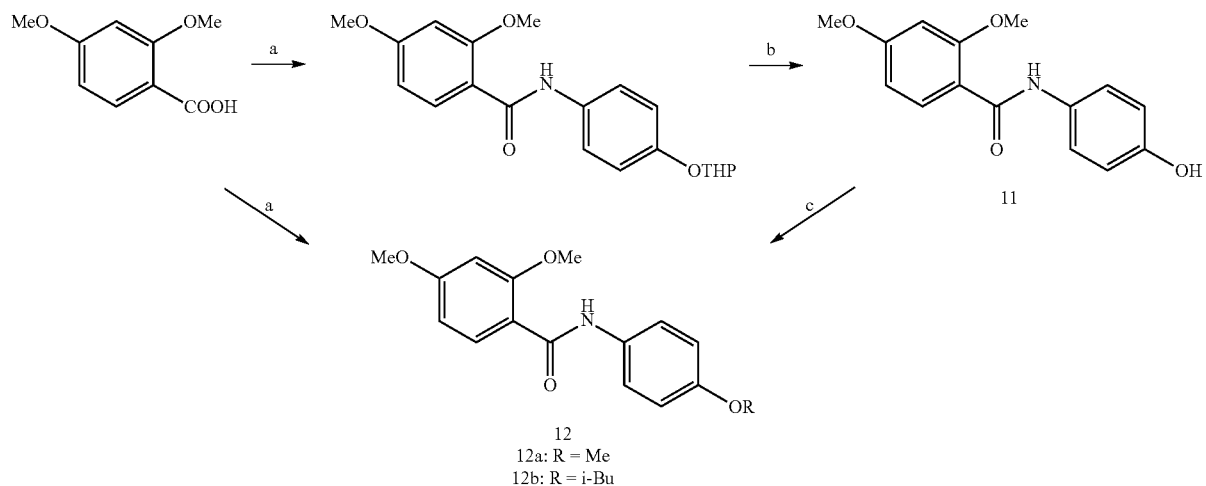

Reagents and conditions: (a) 4-methoxy- or 4-THPO-aniline, DCC, DMAP, DMF, 0° C. - rt; (b) 4-toluenesulfonic acid, MeOH, reflux; (c) K₂CO₃, i-butylbromide, DMSO, rt.

Scheme 2 shows the synthetic route for compounds 11 and 12a-b. The condensation of 2,4-dimethoxybenzoic acid and 4-anisidine or 4-((tetrahydro-2H-pyran-2-yl)oxy)aniline with DCC and DMAP as activating agents gave 12a and 2,4-dimethoxy-N-(4-((tetrahydro-2H-pyran-2-yl)oxy)phenyl)benzamide, respectively. Compound 11 was obtained by the deprotection of 2,4-dimethoxy-N-(4-((tetrahydro-2H-pyran-2-yl)oxy)phenyl)benzamide in methanol with 4-toluenesulfonic acid. Finally, O-i-butylation of 11 in DMSO afforded compound 12b in the presence of K₂CO₃.

Details of Synthesis

Daidzein (1) was obtained from Tyger Scientific Inc. (NJ, USA). Equol was obtained from Beta Pharma, Inc. (CT, USA). Bis(pinacolato)diboron and PdCl₂(dppf) were obtained from CombiPhos Catalyst, Inc (NJ, USA). 4-((Tetrahydro-2H-pyran-2-yl)oxy)aniline was prepared following the method of Itoh et al., *Chemical and Pharmaceutical Bulletin* 1995, 43, 2082-2087, which is herein incorporated by reference in its entirety. All other reagents and solvents were obtained either from Aldrich Chemical Co. (WI, USA) or Acros organics (NY, USA) and were used as received. All organic solvents used were of reagent grade quality and were used without further purification. NMR spectra were recorded on a Varian Unity-400 spectrometer (Varian Inc., Palo Alto, Calif.) and a Bruker Fourier-300 spectrometer (Bruker Inc., Billerica, Mass.) in ppm. GC-MS analyses were performed on an Agilent Technologies 5975C inert MSD mass spectrometer. Melting points were determined with a Mel-temp II point apparatus and are uncorrected. Crude synthetic products were purified by the following methods: chromatography on Silica Gel (60-100 mesh, Fisher Scientific) column. Analytical thin layer chromatography (TLC) was performed on 250µ fluorescent plates (Agela Tech., DE, USA) and visualized by using UV light. For all products, the purity was ascertained to be greater than 95% by the HPLC method using a Shimadzu (Columbia, Md.) 2010 HPLC-UV/MS system with a C-18 reverse phase column. Microwave heating was performed in the single-mode microwave cavity of a Discover Synthesis System (CEM Co., NC, USA), and all microwave reactions were conducted in a heavy-walled glass vials sealed with Teflon septa.

General Procedure for the Synthesis of Compounds 2i-l and 6

To a solution of daidzein (1.27 g, 5 mmol) in 10 mL of DMSO was added anhydrous $K_2CO_3$ (0.90 g, 6.5 mmol) and the bromide or chloride (5.0 mmol). The reaction mixture was stirred at room temperature for 2 hours and then poured into ice water. The resulting mixture was extracted with ethyl acetate. The organic phases were combined, washed with brine, dried over sodium sulfate, filtered, and concentrated under a vacuum. The residue was chromatographed over silica gel using hexanes/ethyl acetate (4:1) as eluant. The product was recrystallized from acetone to provide the 2i-l or 6 as a solid.

3-(4-Hydroxyphenyl)-7-(2-(piperidin-1-yl)ethoxy)-4H-chromen-4-one (2i)

A white powder, 54% yield. LC-MS: m/z 366 (M+H). $^1$H-NMR (DMSO-d6, 300 MHz): δ=1.35 (m, 2H), 1.47 (m, 4H), 2.42 (m, 4H), 2.68 (t, J=5.7 Hz, 2H), 4.21 (t, J=5.7 Hz, 2H), 6.80 (d, J=8.7 Hz, 2H), 7.07 (dd, J=2.4 and 9.0 Hz, 1H), 7.17 (d, J=2.4 Hz, 1H), 7.37 (d, J=8.7 Hz, 2H), 8.00 (d, J=9.0 Hz, 1H), 8.31 (s, 1H), 9.54 (s, 1H, $D_2O$ exchangeable). $^{13}$C-NMR (DMSO-d6, 75 MHz): δ=24.2, 25.7, 54.7, 57.3, 66.7, 101.5, 102.4, 115.5, 115.7, 117.9, 122.8, 124.1, 127.4, 130.6, 153.7, 157.5, 157.9, 175.5.

3-(4-Hydroxyphenyl)-7-(2-(pyrrolidin-1-yl)ethoxy)-4H-chromen-4-one (2j)

A white powder, 47% yield. LC-MS: m/z 352 (M+H). $^1$H-NMR (CDCl$_3$, 400 MHz): δ=1.68 (m, 4H), 2.52 (m, 4H), 2.82 (t, J=6.0 Hz, 2H), 4.21 (t, J=6.0 Hz, 2H), 6.80 (d, J=8.4 Hz, 2H), 7.07 (dd, J=2.4 and 8.8 Hz, 1H), 7.16 (d, J=2.4 Hz, 1H), 7.39 (d, J=8.4 Hz, 2H), 8.01 (d, J=8.8 Hz, 1H), 8.36 (s, 1H), 9.55 (s, 1H, $D_2O$ exchangeable).

7-(2-(Dimethylamino)ethoxy)-3-(4-hydroxyphenyl)-4H-chromen-4-one (2k)

A white powder, 61% yield. LC-MS: m/z 326 (M+H). $^1$H-NMR (DMSO-d6, 300 MHz): δ=2.20 (s, 6H), 2.66 (t, J=5.4 Hz, 2H), 4.18 (t, J=5.4 Hz, 2H), 6.80 (d, J=8.4 Hz, 2H), 7.07 (dd, J=2.4 and 9.0 Hz, 1H), 7.17 (d, J=2.4 Hz, 1H), 7.39 (d, J=8.4 Hz, 2H), 8.01 (d, J=9.0 Hz, 1H), 8.37 (s, 1H), 9.54 (s, 1H, $D_2O$ exchangeable). $^{13}$C-NMR (DMSO-d6, 75 MHz): δ=45.7, 57.6, 67.0, 101.4, 115.5, 115.6, 117.9, 122.8, 124.2, 127.4, 130.6, 153.7, 157.5, 157.9, 163.4, 175.5.

7-(Allyloxy)-3-(4-hydroxyphenyl)-4H-chromen-4-one (2l)

A colorless crystalline, 42% yield. GC-MS: m/z 294 (M+), 253, 137, 118. $^1$H-NMR (DMSO-d6, 300 MHz): δ=4.66 (dt, J=1.5 and 5.4 Hz, 2H), 5.29 (dd, J=1.5 and 10.5 Hz, 1H), 5.40 (dm, J=17.2 Hz, 1H), 6.03 (m, 1H), 6.80 (d, J=9.0 Hz, 2H), 7.04 (dd, J=2.4 and 9.0 Hz, 1H), 7.07 (d, J=2.4 Hz, 1H), 7.34 (d, J=8.8 Hz, 2H), 8.00 (d, J=8.8 Hz, 1H), 8.27 (s, 1H), 9.77 (s, 1H, $D_2O$ exchangeable). $^{13}$C-NMR (DMSO-d6, 75 MHz): δ=69.4, 101.7, 115.5, 115.6, 118.0, 118.8, 122.8, 124.1, 127.4, 130.5, 133.0, 153.6, 157.5, 157.8, 162.9, 175.4.

3-(4-Hydroxyphenyl)-7-(prop-2-yn-1-yloxy)-4H-chromen-4-one (6)

To a solution of 500 mg (1.97 mmol) of daidzein in 40 mL of anhydrous acetone at 0° C., 60 mg (2.36 mol, 1.20 equiv.) of sodium hydride was added. When hydrogen gas evolution was stopped, 0.25 mL (2.32 mmol, 1.18 equiv) of 80% propargyl bromide solution in toluene was added slowly into the reaction mixture. The reaction mixture was then allowed to warm up to room temperature. After the reaction completed, the reaction mixture was purified by flash column chromatography using ethyl acetate/hexanes as eluent affording 327 mg of 3-(4-hydroxyphenyl)-7-(prop-2-yn-1-yloxy)-4H-chromen-4-one (6) in 57% yield. m. p.: 228-230° C. GC-MS: m/z 292 (M+), 254, 207, 174, 145, 118. $^1$H-NMR (MeOD, 300 MHz): δ=3.10 (d, J=2.4 Hz, 1H), 4.93 (d, J=2.4 Hz, 2H), 6.87 (d, J=8.7 Hz, 2H), 7.12-7.18 (m, 2H), 7.40 (d, J=8.7 Hz, 2H), 8.16 (d, J=9.0 Hz, 1H), 8.22 (s, 1H). $^{13}$C-NMR (MeOD, 75 MHz): δ=55.9, 76.5, 101.3, 114.8, 115.1, 126.8, 130.0, 136.4, 153.5.

3-(4-hydroxyphenyl)-8-methyl-4H-furo[2,3-h]chromen-4-one (7)

In a reaction flask, 200 mg (0.68 mmol) of 3-(4-hydroxyphenyl)-7-(prop-2-yn-1-yloxy)-4H-chromen-4-one and 150 mg (0.95 mmol) of CsF was dissolved in 20 mL of N, N-diethylaniline. The reaction was refluxed under nitrogen atmosphere until the starting material completely disappeared on TLC. The reaction solution was then cooled down to room temperature and subjected to flash column chromatography using hexanes/ethyl acetate (99/1) as the eluent to afford 67 mg of 3-(4-hydroxyphenyl)-8-methyl-4H-furo[2,3-h]chromen-4-one (7) in 34% yield. GC-MS: m/z 292 (M+). $^1$H-NMR (d-acetone, 300 MHz): δ=2.56 (s, 3H), 6.90-6.93 (m, 3H), 7.53 (d, J=8.7 Hz, 2H), 7.59 (d, J=8.7 Hz, 1H), 8.08 (d, J=8.7 Hz, 1H), 8.33 (s, 1H), 8.54 (s, 1H). $^{13}$C-NMR (d-acetone, 75 MHz): δ=13.0, 99.9, 109.3, 115.0, 118.4, 119.8, 120.8, 123.4, 124.9, 130.3, 149.8, 152.1, 157.3, 157.4, 157.6, 175.9.

3-(4-Hydroxyphenyl)-8,8-dimethyl-8H-pyrano[2,3f]-chromen-4-one (3)

A solution of daidzein (0.25 g, 1.0 mmol) and 1,1-diethoxy-3-methyl-2-butene (0.20 g, 1.3 mmol) in 2 mL 3-picoline was irradiated at 130° C. for 1 hour under microwave. The solvent was evaporated under a vacuum and the residue was chromatographed over silica gel using hexanes as the eluant. Final product was recrystallized from acetone to give 0.13 g of 3 as colorless needle crystalline in 41% yield. m.p.: 262-264° C. (December). GC-MS: m/z 320 (M+), 305, 254, 187, 152, 118. $^1$H-NMR (DMSO-d6, 400

MHz): δ=1.45 (s, 6H), 5.94 (d, J=10.0 Hz, 1H), 6.79 (d, J=10.0 Hz, 1H), 6.80 (d, J=8.8 Hz, 2H), 6.92 (d, J=8.4 Hz, 1H), 7.38 (d, J=8.8 Hz, 2H), 7.88 (d, J=8.4 Hz, 1H), 8.36 (s, 1H), 9.57 (s, 1H, D$_2$O exchangeable).

3-(4-Hydroxyphenyl)-8,8-dimethyl-2,3,9,10-tetrahydropyrano[2,3-f]chromen-4(8H)-one (4)

Compound 3 (0.50 g, 2.0 mmol) in 100 mL ethyl acetate containing 10% Pd/C (50 mg) was stirred in an atmosphere of hydrogen at room temperature for overnight. The catalyst was filtered off and the filtrate was concentrated. The crude was purified by flash chromatography to give 0.37 g of 4 in yield of 73%. LC-MS: m/z 325 (M+H). m.p.: 176-180° C. (Yield, 73%). $^1$H-NMR (CDCl3, 300 MHz): δ=1.37 and 1.38 (double s, 6H), 1.85-1.80 (t, J=6.6 Hz, 2H), 2.70-2.66 (m, 2H), 3.87 (m, 1H), 4.67-4.55 (m, 2H), 6.51 (d, J=9.0 Hz, 1H), 6.71 (d, J=8.7 Hz, 2H), 7.05 (d, J=9.0 Hz, 2H), 7.77 (d, J=8.7 Hz, 1H). $^{13}$C-NMR (CDCl$_3$, 75 MHz): δ=16.6, 26.6, 26.9, 31.7, 51.1, 72.05, 75.7, 108.9, 112.2, 113.7, 116.1, 126.7, 127.2, 129.8, 155.7, 160.9, 161.2, 191.0.

4-(8,8-Dimethyl-2,3,4,8,9,10-hexahydropyrano[2,3-f]chromen-3-yl)phenol (5)

Compound 3 (0.50 g, 2.0 mmol) in methanol containing 10% Pd/C (50 mg) was stirred in an atmosphere of hydrogen at room temperature for overnight. The catalyst was filtered off and the filtrate was concentrated. The crude was purified by flash chromatography to give 0.32 g of 5 in yield of 67%. GC/MS: m/z 310 (M+, 100%). $^1$H-NMR (CDCl$_3$, 400 MHz): δ=1.32 and 1.33 (double s, 6H), 1.78 (t, J=6.8 Hz, 2H), 2.61-2.66 (m, 2H), 2.90-2.95 (m, 2H), 3.15 (m, 1H), 3.95 (t, J=12.0 Hz, 1H), 4.35 (m, 1H), 4.68 (s, 1H), 6.38 (d, J=12.0 Hz, 1H), 6.81-6.82 (m, 3H), 7.13 (dd, J=4.0 and 8.5 Hz, 2H).

4-(8,8-Dimethyl-4-oxo-4,8-dihydropyrano[2,3-f]chromen-3-yl)phenyltrifluoromethanesulfonate (8)

A solution of trifluoromethanesulfonic anhydride (0.28 g, 0.17 mL, 1.0 mmol) in CH$_2$Cl$_2$ (5.0 mL) was added dropwise to a solution of pyridine (0.1 mL, 1.2 mmol) and 3 (0.25 g, 0.77 mmol) in anhydrous CH$_2$Cl$_2$ (10 mL) at 0° C. After complete addition, the mixture was warmed to room temperature and allowed to stir for 1 hour. The mixture was then diluted with Et$_2$O, quenched with 10% aq HCl and washed successively with sat. NaHCO$_3$ and brine. After drying over MgSO$_4$, the solvent was removed under reduced pressure and the residue was purified by flash column chromatography to give the 4-(8,8-dimethyl-4-oxo-4,8-dihydropyrano[2,3-f]chromen-3-yl)phenyl trifluoromethanesulfonate.

Bis(pinacolato)diboron (0.09 g, 0.35 mmol), PdCl2(dppf) (0.017 g, 5% mol) and KOAc (0.08 g, 0.8 mmol) were added to a 1,4-dioxane solution of 4-(8,8-dimethyl-4-oxo-4,8-dihydropyrano[2,3-f]chromen-3-yl)phenyl trifluoromethanesulfonate (0.15 g, 0.33 mmol), and the mixture was stirred under N$_2$ at 80° C. overnight. After the solution was cooled, the dioxane was removed under vacuum, and CH$_2$Cl$_2$ and water were added. The resulting mixture was extracted with dichloromethane twice, and the combined organic layer was washed with brine and then dried over MgSO$_4$. The organic solvent was concentrated in vacuo. The crude was purified by flash chromatography to afford 66 mg of 8,8-dimethyl-3-(4-(4,4,5,5-tetramethyl-1,3,2-dioxaborolan-2-yl)phenyl) pyrano[2,3-f]chromen-4(8H)-one (8) in yield of 47%. HRMS: calcd 431.2030 (M+H). found 431.2029. m.p.: 228-230° C. $^1$H-NMR (CDCl3, 300 MHz): δ=1.37 (s, 12H), 1.40 (s, 3H), 1.52 (s, 3H), 5.74 (d, J=9.9 Hz, 1H), 6.83 (dd, J=0.6 and 9.9 Hz, 1H), 6.88 (dd, J=0.6 and 8.7 Hz, 1H), 7.58-7.63 (m, 2H), 7.88-7.91 (m, 2H), 8.00 (s, 1H), 8.09 (m, 1H). $^{13}$C-NMR (CDCl$_3$, 75 MHz): δ=24.6, 24.9, 25.0, 28.2, 83.5, 114.9, 115.3, 124.5, 125.0, 125.5, 126.8, 128.2, 128.2, 130.4, 130.7, 134.9, 134.9, 136.4, 152.5, 175.5.

4-(7-Butoxychroman-3-yl)phenol (9)

According to the procedure used to prepare 2i, reaction of equol with 1-bromobutane provided 9 as a white powder in 63% yield. GC-MS m/z 298 (M+), 179, 120). $^1$H-NMR (DMSO-d6, 400 MHz) δ=0.90 (t, J=7.2 Hz, 3H), 1.39 (sextet, J=7.2 Hz, 2H), 1.64 (quintet, J=7.2 Hz, 2H), 2.82 (m, 2H), 3.02 (m, 1H), 3.88 (t, J=7.2 Hz, 2H), 3.89 (m, 1H), 4.18 (m, 1H), 6.32 (d, J=2.4 Hz, 1H), 6.42 (dd, J=2.4 and 8.4 Hz, 1H), 6.70 (d, J=8.4 Hz, 2H), 6.96 (d, J=8.8 Hz, 1H), 7.10 (d, J=8.4 Hz, 2H), 9.28 (s, 1H, D$_2$O exchangeable).

4-(8,8-Dimethyl-2,3,4,8-tetrahydropyrano[3,2-g]chromen-3-yl)phenol (10)

According to the procedure used to prepare 3, reaction of equol with 1,1-diethoxy-3-methyl-2-butene provided of 10 as a colorless liquid in 27% yield. GC-MS: m/z 308 (M+), 293, 187, 173. 1H-NMR (DMSO-d6, 400 MHz): δ=1.32 (s, 6H), 2.78 (m, 2H), 2.80 (m, 1H), 3.91 (m, 1H), 4.21 (m, 1H), 5.57 (d, J=9.2 Hz, 1H), 6.16 (s, 1H), 6.29 (d, J=9.2 Hz, 1H), 6.71 (d, J=8.4 Hz, 2H), 6.78 (s, 1H), 7.10 (d, J=8.4 Hz, 2H), 9.27 (s, 1H, D$_2$O exchangeable).

N-(4-Hydroxyphenyl)-2,4-dimethoxybenzamide (11)

A solution of 5.5 g of 2,4-dimethoxybenzoic acid, 5.8 g of 4-((tetrahydro-2H-pyran-2-yl)oxy)aniline and 300 mg of DMAP in 30 ml of DMF, was treated with 6.2 g of DCC at 0° C. The reaction mixture was stirred for 1 hour at 0° C., then allowed to warm to room temperature and stirred overnight, filtrated and concentrated to afford 2,4-dimethoxy-N-(4-((tetrahydro-2H-pyran-2-yl)oxy)phenyl)benzamide as a white powder in 87% yield, which was used directly in the next step.

12.1 g of 2,4-dimethoxy-N-(4-((tetrahydro-2H-pyran-2-yl)oxy)phenyl)benzamide was treated with 645 mg of 4-toluenesulfonic acid monohydrate in 100 ml of MeOH. The reaction mixture was heated to reflux for 1 hour, and then removed the solvent on vacuum. The solid residue was dissolved in ethyl acetate, washed with brine, dried with Na$_2$SO$_4$, and purified with column chromatography to afford N-(4-hydroxyphenyl)-2,4-dimethoxybenzamide (11) as a white powder in 58% yield. GC/MS: m/z 273 (M+, 100%). $^1$H-NMR (DMSO-d6, 300 MHz): δ=3.86 (s, 3H), 4.01 (s, 3H), 6.62-6.65 (m, 2H), 6.71 (d, J=9.0 Hz, 2H), 7.45 (d, J=9.0 Hz, 2H), 7.75 (d, J=9.3 Hz, 1H), 9.56 (s, 1H). $^{13}$C-NMR (DMSO-d6, 75 MHz): 56.0, 56.6, 98.9, 106.2, 115.5, 116.1, 122.4, 130.9, 132.5, 153.9, 158.8, 163.3, 163.6.

2,4-Dimethoxy-N-(4-methoxyphenyl)benzamide (12a)

A solution of 1.82 g of 2,4-dimethoxy benzoic acid, 1.23 g of 4-anisidine and 0.1 g of DMAP in 10 mL of DMF was treated with 2.06 g of DCC at 0° C. After stirring for 1 hour at 0° C., the reaction mixture was allowed to warm to room temperature and stirred overnight, then filtrated, concentrated and subjected to column chromatography to afford 12a as white powder in 87% yield. 43 GC/MS: m/z 287 (M+, 100%). $^1$H-NMR (CDCl$_3$, 300 MHz): δ=3.81 (s, 3H), 3.88 (s, 3H), 4.02 (s, 3H), 6.53 (d, J=2.4 Hz, 1H), 6.65 (dd, J=2.1 and 8.4 Hz, 1H), 6.90 (d, J=9.0 Hz, 1H), 7.57 (d, J=8.7 Hz, 2H), 8.26 (d, J=8.7 Hz, 1H), 9.55 (s, 1H). $^{13}$C-NMR (CDCl$_3$, 75 MHz): δ=55.5, 55.6, 56.2, 98.8, 105.6, 114.1, 114.8, 122.1, 131.8, 134.2, 156.1, 158.5, 163.0, 163.6.

N-(4-Isobutoxyphenyl)-2,4-dimethoxybenzamide (12b)

A solution of 230 mg of 11, 127 mg of 1-bromo-2-methylpropane and 116 mg of K$_2$CO$_3$ in 2 mL of DMSO was stirred at room temperature for 2 hours, and then quenched with brine, dried with Na$_2$SO$_4$, purified with column chromatography to afford 12b as a white powder in 63% yield. GC/MS: m/z 329 (M+, 100%). $^1$H-NMR (CDCl$_3$, 300 MHz): δ=1.04 (d, J=6.9 Hz, 6H), 2.09 (m, 1H), 3.73 (d, J=6.6 Hz, 2H), 3.89 (s, 3H), 4.03 (s, 3H), 6.55 (d, J=2.4 Hz, 1H), 6.66 (dd, J=2.4 and 9.0 Hz, 1H), 6.90 (d, J=9.0 Hz, 2H), 7.56 (d, J=9.0 Hz, 2H), 8.27 (d, J=8.7 Hz, 1H), 9.58 (s, 1H). $^{13}$C-NMR (CDCl$_3$, 75 MHz): δ=19.3, 28.3, 55.6, 56.2, 74.8, 98.8, 105.6, 114.8, 122.0, 131.6, 134.2, 155.9, 158.5, 162.9, 163.6.

Example 2

Materials and Methods Used in Examples 3-7

Human Bone Marrow Derived Mesenchymal Stem Cells (MSCs).

MSCs from healthy donors were obtained after informed consent and under a protocol approved by Tulane University Institutional Review Board. The cells were prepared from bone marrow aspirates from three individuals. In brief, bone marrow aspirates were taken from the iliac crest of normal adult donors and resuspended in complete culture media (CCM), which consisted of α-MEM (GIBCO®; Grand Island, N.Y.), 20% fetal bovine serum (FBS; Atlanta Biologicals; Lawrenceville, Ga.), 100 units per ml penicillin/100 µg/ml streptomycin (P/S; GIBCO®), and 2 mM L-glutamine (GIBCO®). The cells were then placed in CCM in a 150-cm$^2$ culture dish (Nunc; Rochester, N.Y.) and incubated at 37° C. with 5% humidified CO$_2$. After 24 hours, the media was removed and adherent, viable cells were washed twice with phosphate buffered saline (PBS), harvested with 0.25% trypsin (GIBCO®), and replated at 100 cells/cm$^2$ in CCM. Media was changed every 3-4 day. When the cultures reached 70% confluency, the cells were harvested with trypsin, frozen in α-MEM with 5% dimethyl sulfoxide (DMSO) and 30% FBS, and stored in liquid nitrogen.

Cell Culture.

MSCs were thawed, plated in a 150 cm$^2$ culture dish in CCM and incubated at 37° C. with 5% humidified CO$_2$. After 24 hours, viable cells were washed with PBS, harvested with trypsin, and replated at 100 cells/cm$^2$ in CCM. Media was changed every 3-4 day. For all experiments, sub-confluent cells (<70% confluent) between passages 2-6 were used. Where indicated, cells were treated with DMSO (vehicle), 10 nM estrogen, 1 µM daidzein, or 1 µM daidzein analog cultured in CCM-CDS, which consists of 20% charcoal dextrose stripped FBS (CDS-FBS), 2 mM L-glutamine, and P/S.

Osteogenic Differentiation of MSCs.

To determine the osteogenic potential of the daidzein analogs, MSCs from one or three donors were cultured in CCM, and at 70% confluency, cells were treated with vehicle, estrogen, daidzein, or 1 µM daidzein analog cultured in osteogenic differentiation media (ODM), which consisted of CCM-CDS supplemented with 50 µM ascorbate 2-phosphate (Sigma), 10 mM β-glycerol phosphate (Sigma), and 10 nM dexamethasone. Daidzein analog (1 µM) in fresh bone differentiation media was delivered every 2-3 days. Where indicated, 1 nM, 10 nM, 100 nM, or 1 µM of daidzein analog was delivered to MSCs in ODM to determine the dose-response relationship. After 14 days, cells were fixed in 10% formalin for 1 hour and stained with 40 mM Alizarin Red (pH 4.1) to visualize calcium deposition in the extracellular matrix. Images were acquired at 4× magnification on the Eclipse TE200 with the Digital Camera DXM1200F using the ACT-1 software. To quantify Alizarin Red staining, cells were destained with 10% cetylpyridinium chloride monohydrate (Sigma) for 30 minutes, and the amount of Alizarin Red was determined by measuring the OD of the solution at 590 nm. The results were normalized to the protein content of the samples and compared to cells exposed to vehicle (DMSO) only.

Quantitative Reverse Transcription-Polymerase Chain Reaction (qRT-PCR).

MSCs treated with vehicle, estrogen (10 nM), daidzein (1 µM) and 2c (1 µM) for 14 days was collected for total cellular RNA extraction using RNeasy® Mini Kit. RNA was then purified with DNase I digestion (Invitrogen™), and reverse transcribed using the SuperScript® VILO cDNA synthesis kit (Invitrogen™). Quantitative real-time PCR was performed using the EXPRESS SYBR® GreenER™ qPCR SuperMix Kit (Invitrogen™) according to the manufacturer's instructions. The following primer set sequence for was used: Sp7 forward 5'-CCAGTGTCTACACCTCTC-3' (SEQ ID NO: 1), reverse 5'-ATGGAGTAGGAGTGTTGC-3' (SEQ ID NO: 2); IGF-1 forward 5'-CTGT-GATCTAAGGAGGCTG-3' (SEQ ID NO: 3), reverse 5'-TTCGTGTTCTTGTTGGTAGA-3' (SEQ ID NO: 4); ALP forward 5'-CTAACTCCTTAGTGCCAGAG-3' (SEQ ID NO: 5), reverse 5'-CATGATGACATTCTTAGCCAC-3' (SEQ ID NO: 6); osteopontin forward 5'-GCTCTAGAAT-GAGAATTGCACTG-3' (SEQ ID NO: 7), reverse 5'-GT-CAATGGAGTCCTGGCTGT-3' (SEQ ID NO: 8). β-actin forward 5'-CACCTTCTACAATGAGCTGC-3' (SEQ ID NO: 9), reverse 3'-TCTTCTCGATGCTCGACGGA-5' (SEQ ID NO: 10) was used as an internal reference point. At the completion of the reaction, $\Delta\Delta C_t$ was calculated to quantify mRNA expression.

Example 3

Estrogen and Daidzein Enhance Osteogenic Differentiation of MSCs

Figure 1B:
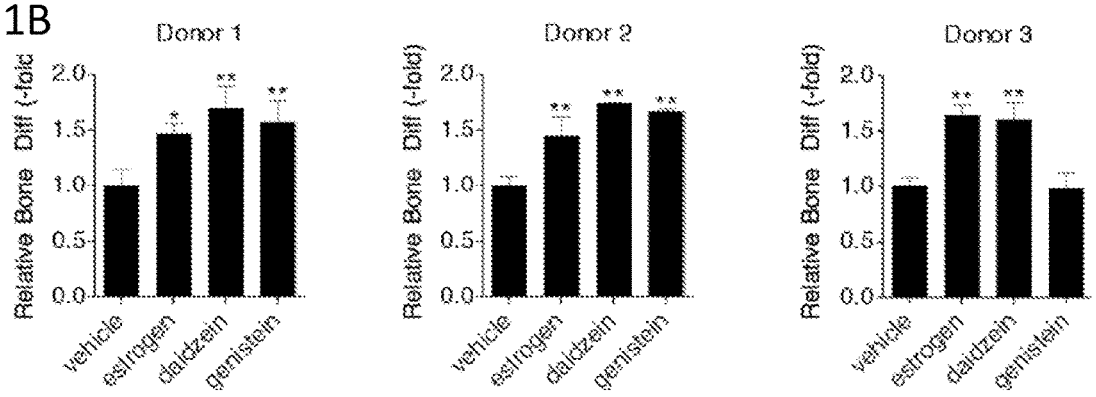

MSCs from three donors were individually treated with vehicle, estrogen, daidzein, or genistein, stained with Alizarin Red, and destained to quantify the amount of stain for each treatment group. Alizarin red is a good indicator of osteogenic differentiation as it stains calcified extracellular matrix associated with bone formation. Estrogen enhanced osteogenic differentiation of MSCs by a fold of 1.5±0.09, 1.5±0.18, and 1.6±0.09 relative to vehicle treated MSCs from Donor 1, Donor 2, and Donor 3, respectively (P<0.05; FIG. 1), and daidzein enhanced the osteogenic differentiation of MSCs by 1.7±0.19, 1.7±0.01, and 1.6±0.15 fold relative to vehicle treated MSCs from Donor 1, Donor 2, and Donor 3, respectively (P<0.05; FIG. 1). Consistent with previous studies, MSCs can be induced to undergo osteogenic differentiation, yet in the presence of estrogen, daidzein, or genistein, the overall potential to undergo differentiation is enhanced. Only estrogen and daidzein consistently enhanced osteogenic differentiation of MSCs in all three donors. Genistein enhanced the osteogenic differentiation of MSCs by 1.6±0.19 and 1.7±0.02 fold relative to vehicle treated MSCs from Donor 1 and Donor 2, respectively (P<0.05; FIG. 1), but it did not induce differentiation of MSCs from Donor 3 (1.0±0.15; P>0.05; FIG. 1).

Previous studies have focused on the delivery of genistein and daidzein to ovariectomized osteoporotic animal models and have shown a reduction in bone loss with the use of these isoflavones. Ovariectomized rats on daidzein supplemented diets were comparable to sham-treated rats in bone mineral density (BMD) in the lumbar vertebrae, femur, and its metaphyseal and diaphyseal zones, which are rich in cancellous and cortical bone. Furthermore, daidzein has been shown to enhance osteogenesis of mouse bone marrow cells and mouse osteoprogenitor cells through ALP activity and nodule formation (Dang and Lowik, *Trends in endocrinology and metabolism* 2005, 16, 207-213). Rassi et al. demonstrated that osteoclast maturation was inhibited in vivo, resulting in limited bone resorption and increased BMD (Rassi et al., *J Bone Miner Res* 2002, 17, 630-638).

Example 4

Figure 2:
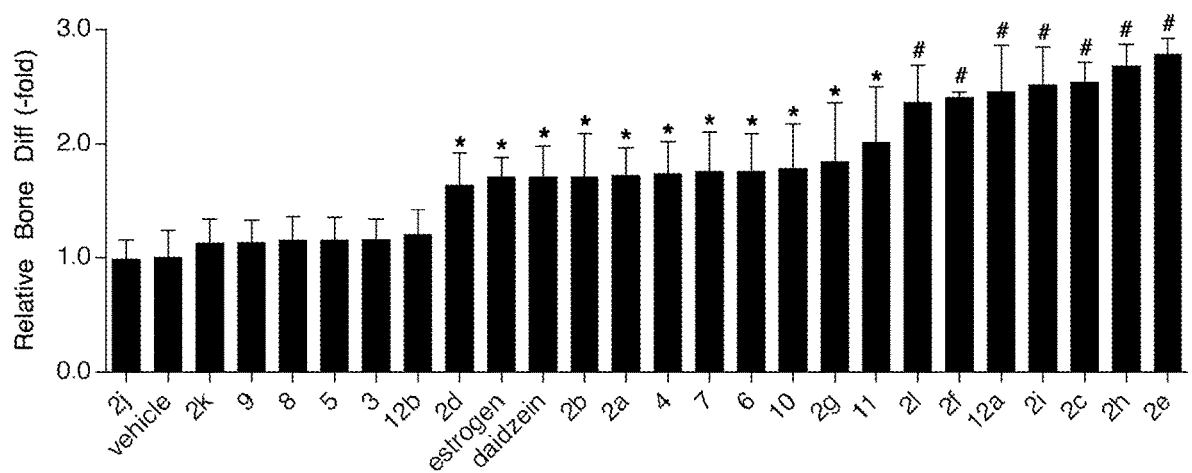
FIG. 2 is a bar graph showing the screening daidzein analogs identified several molecules to further enhanced osteogenesis of MSCs compared to daidzein. MSCs from Donor #1 were induced to undergo osteogenic differentiation and simultaneously exposed to vehicle (DMSO), estrogen (10 nM), daidzein (1 µM), or daidzein analogs (1 µM) at every medium change. After 14 days in osteogenic differentiation media, cells were stained with Alizarin Red S to determine calcium deposition. Cells stained with Alizarin Red S were destained with cetylpyridinium chloride, and measured at 590 nm to quantify the amount of calcium deposit. Bone differentiation potential was determined relative to vehicle-treated cells normalized to 1.0. *, P<0.05, #P<0.01.

Daidzein Analogs Enhanced Osteogenic Differentiation of MSCs with Greater Efficacy than Estrogen or Daidzein Twenty-three daidzein analogs were screened to determine their ability to enhance osteogenic differentiation. Initially, MSCs from one donor (age: 21 yrs old; BMI: 22.7; race: Caucasian, gender: female) was treated with estrogen, daidzein, or daidzein analog in osteogenic differentiation media (ODM). After 14 days, cells were stained with Alizarin Red and destained to quantify the amount of stain for each treatment group. Estrogen and daidzein enhanced osteogenic differentiation of MSCs 1.7±0.2 (P<0.05; FIG. 2) and 1.7±0.3 (P<0.05; FIG. 2) relative to vehicle treated MSCs in ODM, respectively. The effect of the daidzein analogs on osteogenic differentiation can be divided into three groups: no induction, low induction, and high induction. Sixteen of the 23 daidzein analogs enhanced osteogenic differentiation (P<0.05; FIG. 2). Nine of the 23 daidzein analogs fall into the low induction category and induce osteogenic differentiation 1.6-fold to 2.0-fold relative to vehicle: 2d, 2b, 2a, 4, 7, 6, 10, 2g, and 12b, in ascending order. Seven of the daidzein analogs were high inducers of osteogenic differentiation (as high as >2.4-fold increase relative to vehicle): 2l, 2f, 12a, 2i, 2c, 2h, 2e, in ascending order. When tested alongside the daidzein analogs, estrogen and daidzein were only low inducers of osteogenic differentiation.

Figure 3:
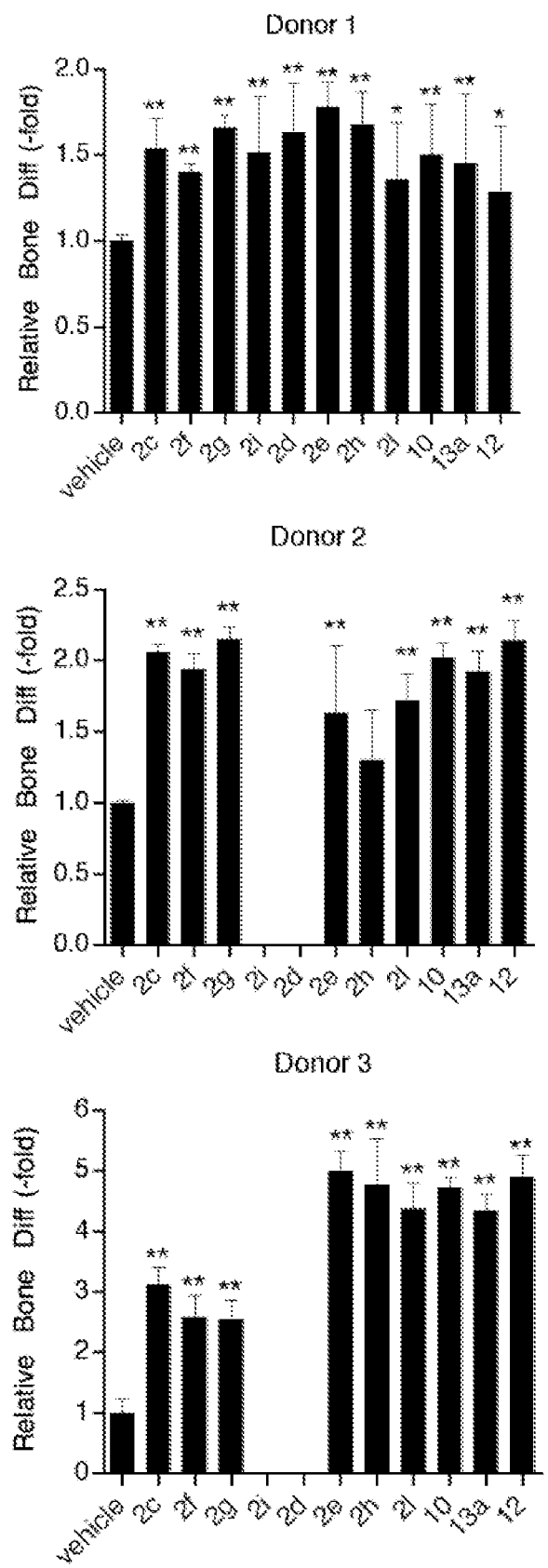
FIG. 3 is a set of bar graphs showing daidzein analogs enhance osteogenesis of MSCs from several donors compared to daidzein. MSCs from three donors were induced to undergo osteogenic differentiation and simultaneously exposed to vehicle (DMSO) or daidzein analogs (1 µM) at every medium change. After 14 days in osteogenic differentiation media, cells were stained with Alizarin Red S to determine calcium deposition. Cells stained with Alizarin Red S were destained with cetylpyridinium chloride, and measured at 590 nm to quantify the amount of calcium deposition. Bone differentiation potential was determined relative to vehicle-treated cells. **, P<0.01.

To identify the most potent osteogenic daidzein analogs and determine the robustness of the daidzein analogs in inducing osteogenesis, the 10 osteogenic daidzein analogs that resulted in the highest levels of differentiation in Donor 1 were further examined after 14 days of differentiation in a total of three donors (mean age: 22.4 years old; mean BMI: 21.5; race: Caucasian; gender: female). Of the ten compounds investigated, 2i and 2d were cytotoxic to MSCs from Donor 2 and Donor 3 (FIG. 3). The other 8 compounds, 2c, 2f, 2g, 2e, 2h, 2l, 10, 13a, and 12, enhanced osteogenesis in all three donors, averaging 2.0±0.41, 1.8±0.48, 2.0±0.64, 2.3±0.33, 2.0±0.48, 2.0±0.18, 2.2±0.19, 2.1±0.14, and 2.2±0.42, respectively, relative to vehicle treated MSCs (P<0.05).

Example 5

Figure 4:
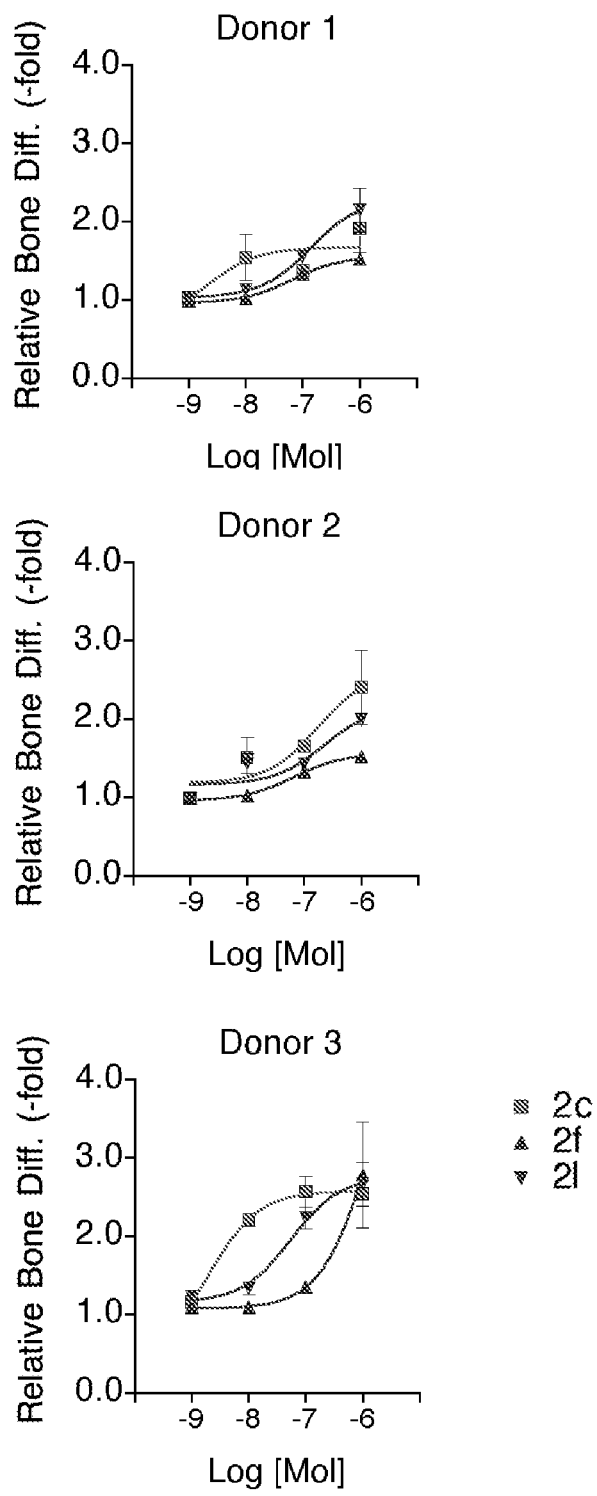
FIG. 4 is a set of graphs showing the enhanced osteogenic potential by the daidzein analogs is dose dependent. MSCs from three donors were induced to undergo osteogenic differentiation and simultaneously exposed to daidzein analogs 2c, 2f, or 2l at 1 nM, 10 nM, 100 nM, or 1 µM concentrations at every medium change. After 14 days in osteogenic differentiation media, cells were stained with Alizarin Red S to determine calcium deposition. Cells stained with Alizarin Red S were destained with cetylpyridinium chloride, and measured at 590 nm to quantify the amount of calcium deposit. Bone differentiation potential was determined relative to vehicle-treated cells.

Selected Daidzein Analogs Exhibit Low $IC_{50}$ Concentrations in Stimulating Bone Differentiation To further determine the dose-dependence of the daidzein analogs in osteogenic activity, the degree of bone differentiation of the MSCs was determined following treatment with varying concentrations of three selected daidzein analogs: 2c, 2f, and 2l. These three selected daidzein analogs demonstrated enhanced differentiation at day 7, suggesting earlier and more robust osteogenic stimulation. The MSCs (n=3 donors) were exposed to log-fold increases (1 nM, 10 nM, 100 nM, or 1 μM) to each of the three daidzein analogs, and after 14 days, cells were stained with Alizarin Red and destained for quantification. As shown in FIG. 4, if $IC_{50}$ values are defined as the analog concentrations required to achieve 1.5 fold relative bone differentiation, the three analogs appear to have $IC_{50}$ values in the range of <1 nM to >1 μM, depending on donor. The $IC_{50}$ for 2c, 2f, and 2l for donor 1 is 2.2 nM, 65.8 nM, and 136.0 nM, respectively; the $IC_{50}$ for 2c, 2f, and 2l for donor 2 is 170.4 nM, 65.7 nM, and 223.7 nM, respectively; the $IC_{50}$ for 2c, 2f, and 2l for donor 3 is 2.1 nM, 1.38 μM, and 55.1 nM, respectively. The $IC_{50}$ for 2c, 2f, and 2l averaged among the three donors is 58.2 nM, 503.8 nM, and 138.2 nM. Thus, while donor variability adds to the uncertainty in $IC_{50}$ values, the order of osteogenesis potency for the three analogs in different donors appears to be consistent. For example, the $IC_{50}$ for analog 2f for Donor 1, Donor 2, and Donor 3 was 65.8 nM, 65.7 nM and 1.38 μM, respectively, representing the least potent analog. In contrast, the $IC_{50}$ for analog 2c was 2.2 nM and 2.1 nM in the MSCs from Donor 1 and Donor 3, and 170 nM in Donor 2 cells, representing the most potent analog among the three (P<0.05; FIG. 4).

Example 6

Daidzein Analogs Enhance Osteogenic Transcription Factor Expression in MSCs

Figure 5:
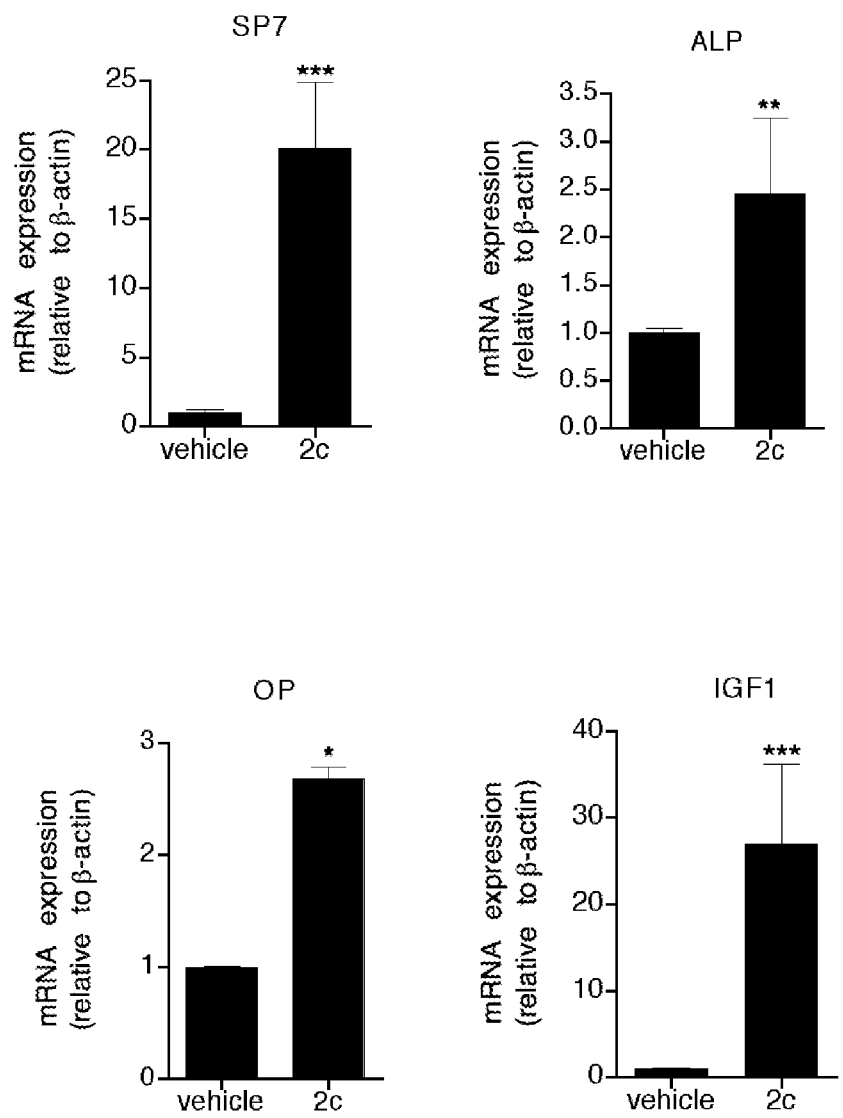
FIG. 5 is a set of bar graphs showing enhanced osteogenic potential by daidzein analog correlates with enhanced expression of osteogenic transcription factors. MSCs from three donors were pooled together, induced to undergo osteogenic differentiation, and simultaneously exposed to vehicle or daidzein analog 2c (1 µM) at every medium change. After 14 days, cells were harvested, RNA was isolated, and cDNA was synthesized from each sample. Real time RT-PCR of transcript levels of genes (SP7, ALP, OP, IGF1) involved in osteogenesis was analyzed. *, P<0.05, , P<0.01, *, P<0.001.

To investigate the mechanism by which daidzein analogs enhance osteogenic differentiation of MSCs, cells treated with 2c as a supplement to ODM for 14 days were compared to cells treated with vehicle in ODM. Cells were collected for RNA extraction, cDNA synthesis, and analyzed by qRT-PCR for the expression of osteogenic transcription factors. Cells treated with ODM containing 2c expressed higher concentrations of Sp7 (20.08±4.81), ALP (2.45±0.80), OP (2.68±0.11), and IGF1 (26.96±9.19), relative to cells treated with vehicle in ODM (P<0.05; FIG. 5). Sp7 is one of the earlier genes necessary to commit progenitor stem cells or MSCs into the osteoblast lineage. Following lineage commitment, osteoprogenitors undergo a proliferative stage and subsequently express genes, such as alkaline phosphatase (ALP), bone sialoprotein, and collagen type I, as they produce the osteogenic extracellular matrix. In the final stages of maturation, these osteoprogenitor cells mineralize the extracellular matrix and produce osteopontin (OP) and osteocalcin. Once mature bone is formed, insulin-like growth factor 1 (IGF-1) regulates bone density to allow for strength and durability. This highly regulated program of gene expression and cellular differentiation is governed by the expression and activity of a myriad of transcription factors. These factors act in conjunction with other transcription factors in an integrated and specific manner to allow for successful generation of bone.

Increased expression of Sp7, ALP, OP, and IGF-1 in human MSCs treated with daidzein analog 2c support increased bone formation observed phenotypically. Recent studies have described similar increases in ALP and IGF-1 expression in mouse osteoblast cells exposed to estrogen. As a phytoestrogen, additional studies on daidzein have investigated the potential upregulation of downstream receptors, such as estrogen receptor alpha (ERα) and estrogen receptor beta (ERβ). These studies have demonstrated that daidzein increases not only ERα and ERβ expression but also vitamin D receptor synthesis, suggesting that daidzein promotes bone formation and maturation through these estrogen dependent pathways.[40,41] While further mechanistic studies are necessary to delineate the exact mode of action and pathways involved, results obtained thus far suggest that these daidzein analogs are likely to be more efficient activators of the estrogen pathway, increasing the synthesis and maturation of bone.

Example 7

Structure-Activity Relationships

Of the twelve 2 series daidzein analogs, 2a, 2b, and 2g demonstrated modest osteogenic activity in all three donor cells comparable to those of estrogen and daidzein, while 2d showed toxicity to two donor cells and modest osteogenesis in the third. Thus, methyl, ethyl, n-propyl, and cyclopentyl substitutions for the hydroxyl hydrogen failed to bring about significantly improved osteogenic potential. However, when the substitution group was isopropyl (2c), n-butyl (2e), 2-butyl (2f), allyl (2l), or n-hexyl (2h), marked enhancement of osteogenic potentials were observed. In fact, these analogs represent the most potent compounds in promoting bone formation in the stem cells of all three donors. Interestingly, analog 6, in which the substitution is a propyl-1-yne, showed only modest osteogenic potential. When comparing the activity of 6, 2d, and 2l, an optimal structure for a three-carbon substitution is one containing a double bond, not a triple bond, nor a saturated sigma bond. Also, in the 2 series, it was observed that, of the three daidzein analogs that have polar substitutions containing nitrogen (2i, 2j, and 2k), two had no osteogenic effect (2j and 2k), while the third showed potent toxicity to two donors, indicating that increased polarity on the 7-O position may not be desirable in retaining osteogenic activity.

Other structural modifications involving cyclization on the 7,8 position did not yield significant osteogenic potential. For example, of the three cyclic analogs (3, 4, and 7), analog 3 did not exhibit any osteogenic activity while 4 and 7 showed modest potential in promoting bone regeneration. When the daidzein structural moiety in the center was modified to that of equol, a daidzein metabolite, there appeared to be a significant loss of activity. For example, the analog 2e is one of the most potent compounds promoting over two-fold increase of bone formation in 14 days. Change of the central moiety of the molecule to that of equol (i.e., reductive removal of the carbonyl and the double bond on the central six-membered ring) results in analog 9, which has no osteogenic activity in any of the three donor stem cells. In another comparable pair, the daidzein analog 4 showed modest osteogenic potential while the equol analog 5 had no discernible osteogenic activity.

Attempts to open the central ring system gave mixed results. In analog 11, 12a, and 12b, the introduction of an amide bond replacing the ring structure allowed both phenyl rings to rotate freely. Of the three, 12a did exhibit strong osteogenic activity, indicating that the rigid quinone ring structure may not be required. However, the other two analogs, 11 and 12b were not active at all, suggesting that the optimal substitution on the 4' position may be methoxy, not the original hydroxyl group or an i-butoxy group.

Example 8

Materials and Methods Used in Examples 9-XX

Anti-CD45-PeCy7, anti-CD11b-PeCy5, anti-CD166-phycoerythrin (PE), anti-CD105-PE, anti-CD90-PeCy5, anti-CD34-PE, isotype control fluorescein isothiocyanate (FITC) human IgG1, and isotype-control PE human IgG2a were obtained from Beckman Coulter (Indianapolis, Ind.). Anti-CD44-allophycocyanin (APC) was purchased from BD Biosciences (San Jose, Calif.). Type 1 collagenase, bovine serum albumin (BSA, fraction V), calcium chloride, dexamethasone, isobutylmethylxanthine, indomethacin, ascorbate 2-phosphate, β-glycerol phosphate, Alizarin Red S, Oil Red O, BCIP/NBT, silver nitrate, 17β-estradiol, and daidzein were obtained from Sigma (St. Louis, Mo.).

Primary Cells

Primary human BMSCs were obtained from six healthy consenting Caucasian female donors. The cells were prepared from bone marrow aspirates taken from the iliac crest of these six individuals. Nucleated cells were isolated using Ficoll-Paque density gradient (Amersham Pharmacia Biotech; Milwaukee, Wis.) and resuspended in complete culture media (CCM), which consisted of α-Minimal Essential Medium (αMEM; Gibco; Grand Island, N.Y.), 20% fetal bovine serum (Atlanta Biologicals, Lawrenceville, Ga.), 100 units per ml penicillin/100 μg/mL streptomycin (P/S; Gibco®), and 2 mM L-glutamine (Gibco®). The cells were then seeded on a 150 $cm^2$ culture dish (Nunc®; Rochester, N.Y.) and maintained in a humidified 5% $CO_2$ incubator at 37° C. Media was changed every 3-4 day. When the cultures reached 70% confluent, the cells were harvested with 0.25% trypsin/1 mM EDTA (Gibco®) and cryopreserved prior to experimental use.

Primary human ASCs were obtained from six healthy consenting Caucasian females donors undergoing elective liposuction procedures. ASCs were isolated from processed lipoaspirates from the subcutaneous adipose tissue of subjects. Liposuction aspirates were incubated in 0.1% type I collagenase and 1% BSA dissolved in 100 ml of phosphate buffered saline (PBS) supplemented with 2 mM calcium chloride. The mixture was placed in a 37° C. shaking water bath at 75 rpm for 60 min and then centrifuged to remove oil, fat, primary adipocytes, and collagenase solution, leaving behind a pellet of cells. Cells were resuspended in CCM, and plated on 150 $cm^2$ culture dishes. Cells were also maintained in a humidified 5% $CO_2$ incubator. Fresh CCM was added every 2-3 days until cells achieved 80-90% confluence and were then harvested with 0.25% trypsin/1 mM EDTA and cryopreserved prior to use.

Cell Culture

Frozen vials of approximately $10^6$ BMSCs or ASCs were thawed, plated onto 150 $cm^2$ culture dishes (Nunc®, Rochester, N.Y.) in 20 ml CCM and incubated at 37° C. with 5% humidified $CO_2$. After 24 hours, the media was removed and adherent, viable cells were washed with PBS, harvested with 0.25% trypsin/1 mM EDTA (Gibco®), and replated at 100 cells per cm² in CCM. Media was replaced every 3-4 days. For all experiments, subconfluent cells (<70% confluent) between passages 2-6 were used.

Flow Cytometry

ASCs were harvested with 0.25% trypsin/1 mM EDTA for 3-4 minutes at 37° C. A total of 3×10⁵ cells were suspended in 50 µl PBS and labeled with the primary antibodies. The samples were incubated for 30 minutes at room temperature and washed with PBS. The samples were then analyzed with Galios® Flow Cytometer (Beckman Coulter, Brea, Calif.) running Kaluza® software (Beckman Coulter). To assay cells by forward and side scatter of light, FACScanGalios® Flow Cytometer was standardized with microbeads (Dynasphere uniform microspheres; Bangs Laboratories Inc.; Thermo Scientific; Waltham, Mass.). At least 10,000 events were analyzed and compared with isotype controls.

Colony Forming Unit Assay

BMSCs and ASCs were plated at a density of 100 cells on a 10 cm² plate in CCM and incubated for 14 days. Plates were then rinsed with PBS and stained with 3% crystal violet (Sigma) for 30 minutes at room temperature. Plates were washed with PBS and once with tap water. Colonies that were larger than 2 mm in diameter were counted. Each experiment was performed in triplicate.

Differentiation Protocols

Osteogenic Differentiation.

BMSCs and ASCs were cultured in six-well plates in CCM until 70% confluent. Media was replaced with fresh osteogenic differentiation media made with CCM supplemented with 50 µM ascorbate 2-phosphate, 10 mM β-glycerol phosphate, and 10 nM dexamethasone. Where indicated, media consisting of charcoal dextran stripped fetal bovine serum (CDS-FBS) (Atlanta Biologicals; Lawrenceville, Ga.) was substituted for regular FBS, and osteogenic differentiation media was supplemented with 10 nM estrogen, 1 µM daidzein, or 1 µM daidzein analog for the duration of the differentiation. Estrogen inhibitor studies were conducted by concurrent treatment with 100 nM fulvestrant (ICI187,280; Sigma) and 10 nM estrogen, 1 µM daidzein, or 1 µM daidzein analogs.

Adipogenic Differentiation.

BMSCs and ASCs were cultured in six-well plates in CCM until 70% confluent. Media was replaced with fresh adipogenic induction media made with CCM supplemented with 0.5 µM dexamethasone, 0.5 mM isobutylmethylxanthine, and 50 µM indomethacin. Where indicated, media consisting of CDS-FBS (Atlanta Biologicals; Lawrenceville, Ga.) was substituted for regular FBS, and adipogenic differentiation media was supplemented with 10 nM estrogen, 1 µM daidzein, or 1 µM daidzein analog for the duration of the differentiation.

Staining Protocols

Alizarin Red Staining.

After 14 days, cells undergoing osteogenic differentiation in osteogenic differentiation media were fixed in 10% formalin for 1 hour, washed with distilled water, and stained with 1% alizarin red s (pH 4.1) to visualize calcium deposition in the extracellular matrix. Images were acquired at 4× magnification on Nikon Eclipse TE200 (Melville, N.Y.) with Nikon Digital Camera DXM1200F using Nikon ACT-1 software version 2.7. Scale bar represents 100 µm.

Oil Red O Staining.

After 14 days, cells undergoing adipogenic differentiation in adipogenic differentiation media were fixed in 10% formalin for 1 hour, and stained with Oil Red 0, composed of 2 parts PBS and 3 parts 0.5% Oil Red 0 stock solution to visualize neutral lipids. Images were acquired at 10× magnification on Nikon Eclipse TE200 with Nikon Digital Camera DXM1200F using the Nikon ACT-1 software version 2.7. Scale bar represents 100 µm.

Alkaline Phosphatase Staining.

After 3 days, cells undergoing osteogenic differentiation in osteogenic differentiation media were fixed in 10% formalin for 1 hour, washed with distilled water, and incubated in BCIP/NBT to visualize alkaline phosphatase activity. Images were acquired at 4× magnification on Nikon Eclipse TE200 with Nikon Digital Camera DXM1200F using Nikon ACT-1 software version 2.7. Scale bar represents 100 µm.

Silver Nitrate Staining.

After 14 days, cells undergoing osteogenic differentiation in osteogenic differentiation media were fixed in 10% formalin for 1 hour, washed with distilled water, and incubated in 3% silver nitrate to visualize phosphate mineralization in the extracellular matrix. Images were acquired at 4× magnification on Nikon Eclipse TE200 with Nikon Digital Camera DXM1200F using Nikon ACT-1 software version 2.7. Scale bar represents 100 µm.

RNA Isolation, cDNA Synthesis, Quantitative RT-PCR (qPCR).

Cells treated with vehicle, 10 nM estrogen, 1 µM daidzein, or 1 µM daidzein analog in osteogenic differentiation media were collected on days 3, 7 and 14. Where indicated, BMSCs and ASCs treated with vehicle, estrogen, daidzein, and daidzein analog were simultaneously treated with 100 nM fulvestrant and collected on days 3, 7, and 14. Total cellular RNA was extracted from BMSCs and ASCs using the RNeasy Mini Kit (Qiagen, Valencia, Calif.), purified with DNase I digestion (Invitrogen™) according to manufacturer's instructions, and reverse transcribed using the SuperScript® VILO cDNA synthesis kit (Invitrogen™). Quantitative real-time PCR was performed using the EXPRESS SYBR® GreenER™ qPCR SuperMix Kit (Invitrogen™) according to the manufacturer's instructions. The following forward and reverse primer sequences were used to detect changes in gene expression: runt-related transcription factor 2 (RUNX2), 5'-CTCACTACCACACC-TACCTG-3' (SEQ ID NO: 11) and 5'-TCAATATGGTCGC-CAAACAGATTC-3' (SEQ ID NO: 12); FBJ murine osteosarcoma viral oncogene homolog (c-Fos), 5'-CCTGT-CAAGAGCATCAGCAG-3' (SEQ ID NO: 13) and 5'-GTCAGAGGAAGGCTCATTGC-5' (SEQ ID NO: 14); osteonectin (SPARC), 5'-TGTGGGAGCTAATCCTGTCC-3' (SEQ ID NO: 15) and 5'-TCAGGACGTTCTT-GAGCCAGT-3' (SEQ ID NO: 16); distal-less homeobox 5 (DLX5), 5'-TGGCCCGAGTCTTCAGCTAC' (SEQ ID NO: 17) and 5'-TGGTTGGTCGGTCTCTTTCT-3' (SEQ ID NO: 18); secreted phosphoprotein 1 (SPP1), 5'-GCTCTAGAAT-GAGAATTGCACTG-3' (SEQ ID NO: 19) and 5'-TGTCGGTCCTGAGGTAACTG-3' (SEQ ID NO: 20); collagen type 1 alpha (COL1A1), 5'-CATGTTCAGCTTTGTGGACCTC-3' (SEQ ID NO: 21) and 5'-AGGTGATTGGTGGGATGTCTT-3' (SEQ ID NO: 22); insulin-like growth factor 1 (IGF1), 5'-CTGT-GATCTAAGGAGGCTG-3' (SEQ ID NO: 23) and 5'-TTCGTGTTCTTGTTGGTAGA-3' (SEQ ID NO: 24); and beta-actin (β-actin), 5'-CACCTTCTACAAT-GAGCTGC-3' (SEQ ID NO: 9) and 3'-TCTTCTC-GATGCTCGACGGA-3' (SEQ ID NO: 10). All RT-PCR primers designed using Primer3 (Boston, Mass.) and purchased from Integrated DNA Technologies (Coralville, Iowa). The expression of human β-actin was used to normalize mRNA content. Samples were tested in triplicates. No-template controls and no-reverse transcription controls were included in each PCR run.

Example 9

BMSCs and ASCs Demonstrate Similar Stem Cell Characteristics

BMSCs and ASCs were stained for cell surface antigens, plated for colony forming units (CFU), and induced to differentiate down osteogenic and adipogenic lineages. BMSCs and ASCs displayed overlapping cell surface marker profiles (CD44$^+$, CD90$^+$, CD106$^+$, CD166$^+$, CD11b$^-$, CD34$^-$, and CD45$^-$), were able to form CFUs, and underwent osteogenic and adipogenic differentiation.

Example 10

Figure 6A:
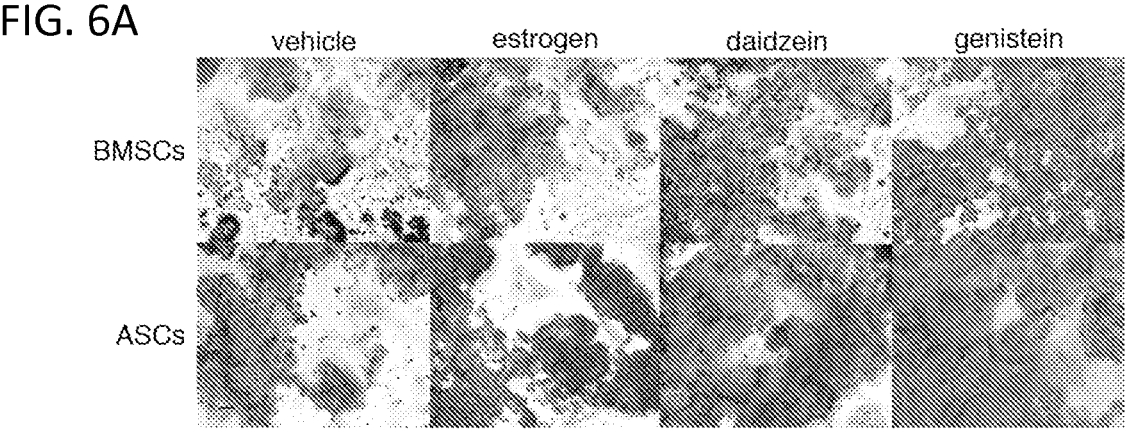
FIGS. 6A-6D is a set of digital images and bar graphs showing that estrogen and phytoestrogens enhance osteogenic and adipogenic differentiation of bone marrow stem cells (BMSCs) and adipose derived stromal/stem cells (ASCs). BMSCs (n=6) and ASCs (n=6) were cultured in osteogenic or adipogenic differentiation media and simultaneously delivered vehicle (DMSO), estrogen (10 nM), daidzein (1 µM), or genistein (1 µM).
Figure 6B:
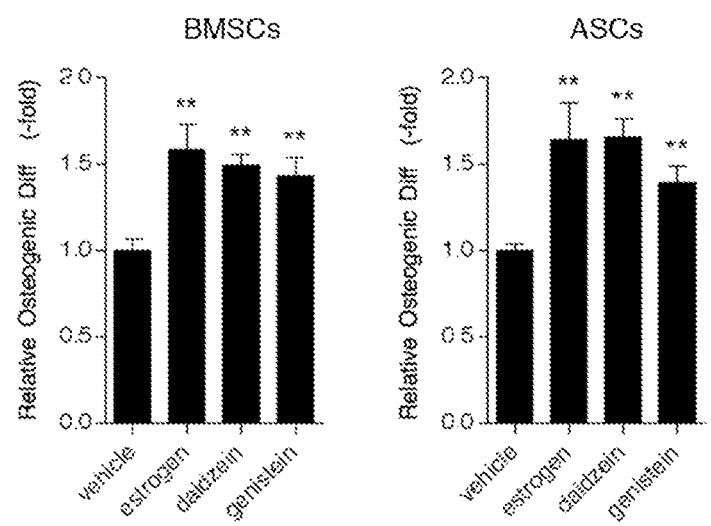

Estrogen and Phytoestrogens Enhance Osteogenic Differentiation while Only Estrogen Enhances Adipogenic Differentiation of BMSCs and ASCs BMSCs and ASCs were cultured in osteogenic differentiation media, consisting of charcoal dextran stripped-fetal bovine serum (CDS-FBS) to remove endogenous estrogens in the FBS, and supplemented with estrogen or phytoestrogens, daidzein or genistein. After 14 days, cells were stained with alizarin red and imaged with bright field microscopy (FIG. 6A). Alizarin red staining was quantified by eluting the alizarin red staining and acquiring optical density measurements. Estrogen-, daidzein-, and genistein-treated BMSCs and ASCs cultured in osteogenic differentiation media demonstrated greater osteogenic differentiation compared to vehicle-treated BMSCs and ASCs. Estrogen-, daidzein-, and genistein-treated BMSCs demonstrated 1.6-, 1.5-, and 1.4-fold greater osteogenic differentiation compared to vehicle-treated BMSCs, respectively ($P<0.01$; FIG. 6B). ASCs treated with estrogen, daidzein, and genistein demonstrated a 1.6-, 1.7-, and 1.4-fold increase in osteogenic differentiation relative to vehicle-treated ASCs (normalized to 1.0) respectively ($P<0.01$; FIG. 6B). While estrogen, daidzein, and genistein all enhanced osteogenic differentiation, 2 of the 6 BMSC donors and 3 of the 6 ASC donors did not respond to genistein treatment, displaying comparable osteogenic differentiation to vehicle-treated BMSCs or ASCs. Furthermore, visualization with bright field microscopy did not demonstrate enhanced cytotoxicity of BMSCs or ASCs treated with estrogen, daidzein, or genistein, compared to vehicle-treated cells.

Figure 6C:
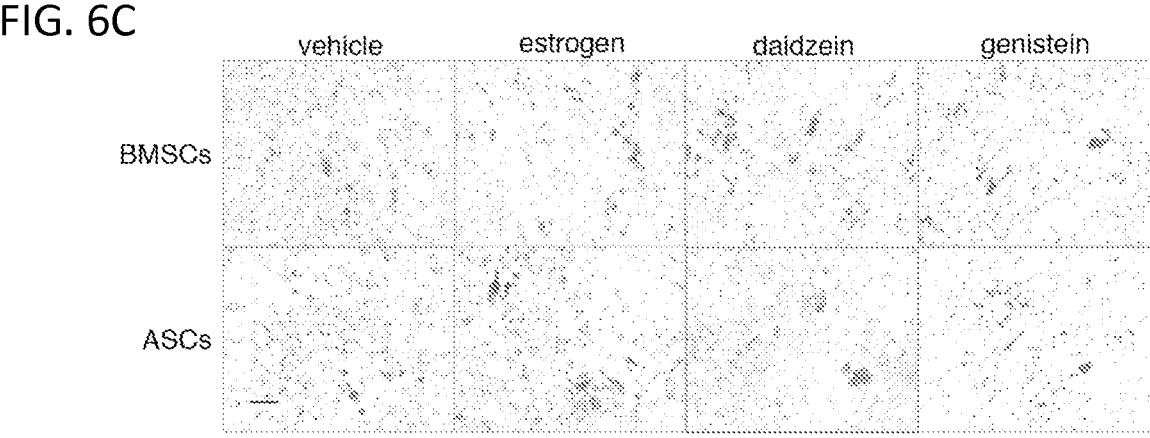
Figure 6D:
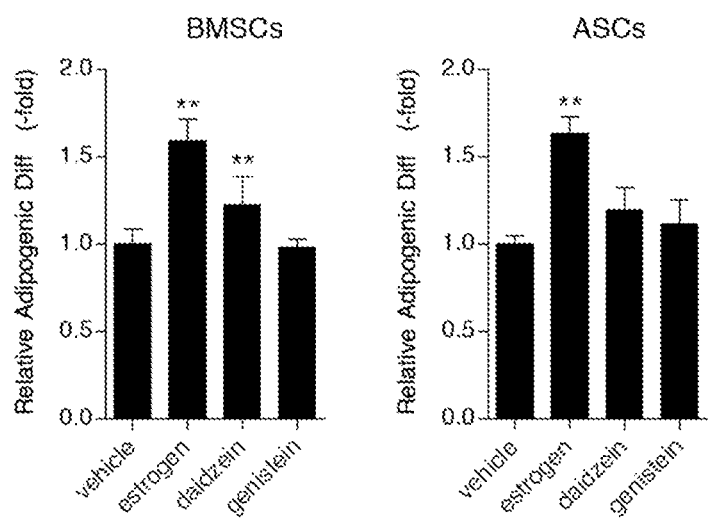

To determine the effect of estrogen or phytoestrogens on adipogenic differentiation of BMSCs and ASCs, cells were conditioned in adipogenic differentiation media, consisting of CDS-FBS, and supplemented with estrogen, daidzein, and genistein. After 14 days, cells were stained with oil red o and imaged with bright field microscopy (FIG. 6C). Oil red staining was quantified by eluting with oil red o staining with isopropanol and measuring the optical density. Estrogen-treated BMSCs and ASCs demonstrated enhanced adipogenic differentiation by 1.6-fold compared to vehicle-treated BMSCs and ASCs, respectively ($P<0.01$; FIG. 6D). Daidzein-treated BMSCs demonstrated enhanced adipogenic differentiation by 1.2 compared to vehicle-treated BMSCs ($P<0.01$; FIG. 6D), while daidzein treatment did not enhance adipogenic differentiation of ASCs.

Figure 7A:
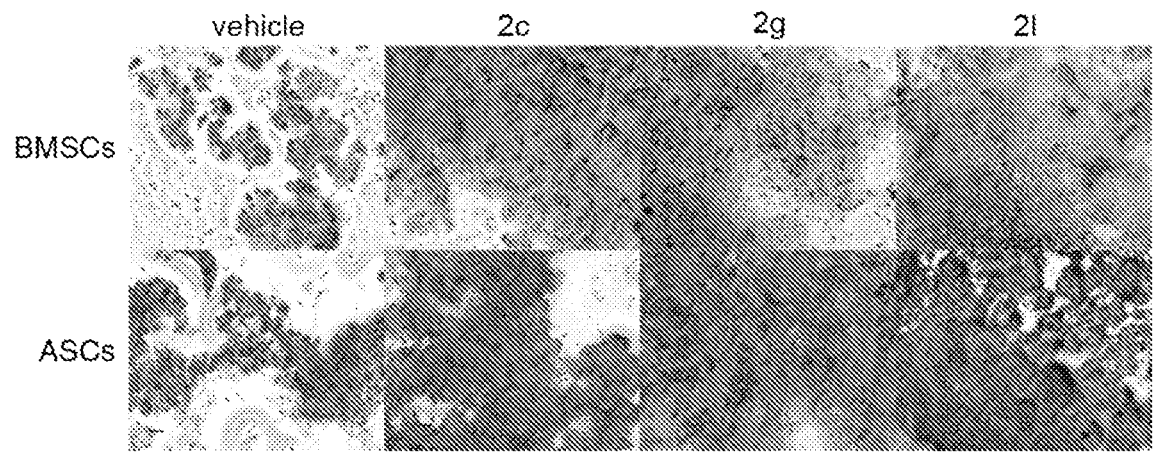
FIGS. 7A and 7B are a set of digital images and bar graphs showing that daidzein analogs induce greater calcium deposition by differentiating BMSCs and ASCs compared to estrogen and daidzein. BMSCs (n=6) and ASCs (n=6) were cultured in osteogenic differentiation media and simultaneously delivered vehicle (DMSO), estrogen (10 nM), daidzein (1 µM), daidzein analog 2c (1 µM), daidzein analog 2g (1 µM), or daidzein analog 2l (1 µM).
Figure 7B:
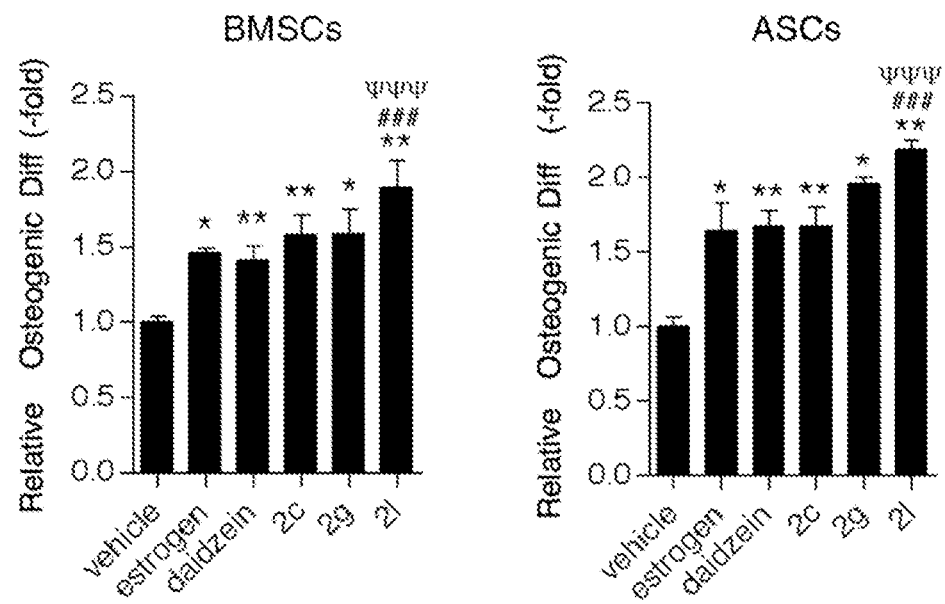

Daidzein Analogs Enhance Osteogenic Differentiation while Reducing Adipogenic Differentiation of BMSCs and ASCs To determine the osteogenic potential of daidzein analogs on BMSCs and ASCs, daidzein analogs were synthesized and were supplemented into osteogenic differentiation media, made with CDS-FBS. BMSCs and ASCs were treated with 2c, 2g, and 2l, at each media change. Cells were then stained with alizarin red and imaged with bright field microscopy (FIG. 7A), and the amount of staining was quantified by eluting with CPC. BMSCs and ASCs treated with 2c, 2g, and 2l demonstrated enhance osteogenesis compared to vehicle-treated BMSCs and ASCs. BMSCs treated with 2c, 2g, and 2l demonstrated a 1.6-, 1.6-, and 1.9-fold increase in osteogenesis, respectively, relative to vehicle-treated BMSCs ($P<0.05$; FIG. 7B). ASCs treated with 2c, 2g, and 2l demonstrated a similar trend and osteogenesis was enhanced by 1.7-, 2.0-, and 2.2-fold increase, respectively, relative to vehicle-treated ASCs ($P<0.05$; FIG. 7B). Furthermore, 2l-treated BMSCs and ASCs demonstrated enhanced osteogenesis compared to estrogen- and daidzein-treated BMSCs and ASCs ($P<0.001$; FIG. 7B), suggesting that 2l is a more potent osteogenic compound than estrogen or daidzein.

While 2c, 2g, and 2l-treated BMSCs and ASCs demonstrated enhanced osteogenic differentiation, these compounds failed to simulate adipogenic differentiation. BMSCs and ASCs treated with 2c demonstrated comparable adipogenic differentiation as vehicle-treated BMSCs and ASCs, while 2g- and 2l-treated BMSCs and ASCs demonstrated a significant reduction in adipogenic differentiation compared to vehicle-, estrogen-, or daidzein-treated BMSCs or ASCs ($P<0.001$).

Figure 8A:
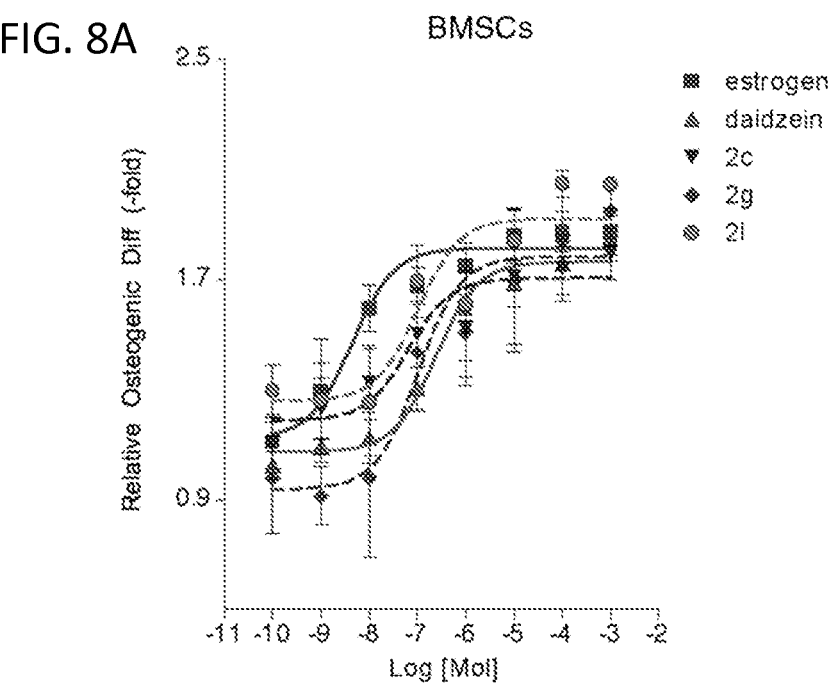
FIGS. 8A and 8B are a set graphs showing the effect of daidzein analogs on osteogenic differentiation of BMSCs and ASCs is dose dependent.
Figure 8B:
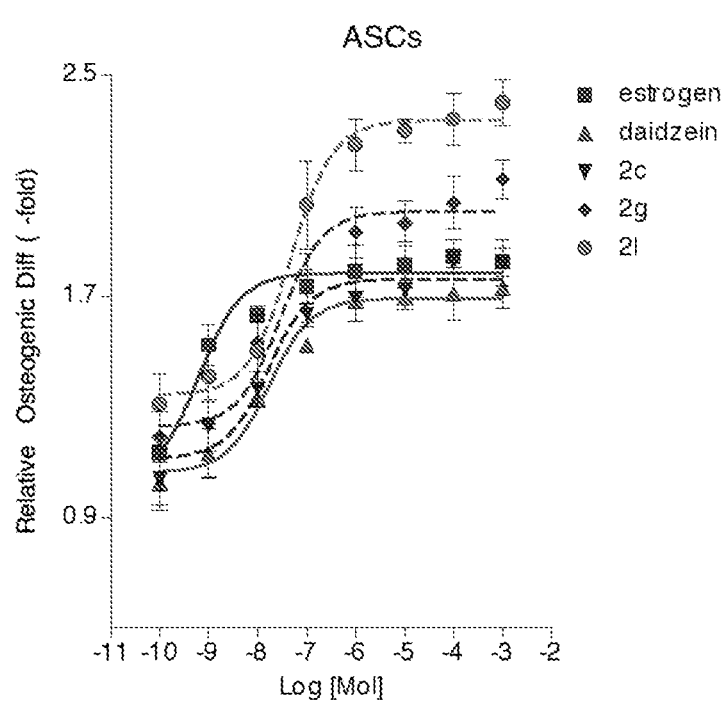

Daidzein Analog 2c, 2g, and 2l have Similar $EC_{50}$-Values but Differ in Effectiveness Additional studies were conducted to determine the concentration of daidzein analogs required to induce 50% of the maximal effect ($EC_{50}$ value) on osteogenesis of BMSCs and ASCs in the most potent compounds: 2g and 2l. Thus, 2g and 2l were administered to BMSCs and ASCs at concentrations ranging from 100 pM to 1 mM, at log fold increases. The results were compared to estrogen and daidzein, also delivered at 100 pM to 1 mM concentrations. The $EC_{50}$ value for estrogen in BMSCs and ASCs was $10^{-8.35}$ and $10^{-9.20}$, respective. The $EC_{50}$ values for daidzein, 2g, and 2l in BMSCs was $10^{-6.62}$, $10^{-6.99}$, and $10^{-6.99}$, respectively. The $EC_{50}$ values for daidzein, 2g, and 2l in ASCs was comparable to BMSCs: $10^{-7.76}$, $10^{-7.53}$, and $10^{-7.32}$, respectively. While estrogen displays the most potent stimulation of osteogenesis in BMSCs and ASCs, leading to enhanced osteogenesis at 1 nM to 10 nM concentrations, 2l had the greatest impact on osteogenic differentiation of BMSCs and ASCs resulting in 2.0 to 2.4-fold increase in osteogenesis (FIG. 8). Higher doses of estrogen were unable to induce further osteogenesis equal to or exceeding that of 2l.

Figure 9A:
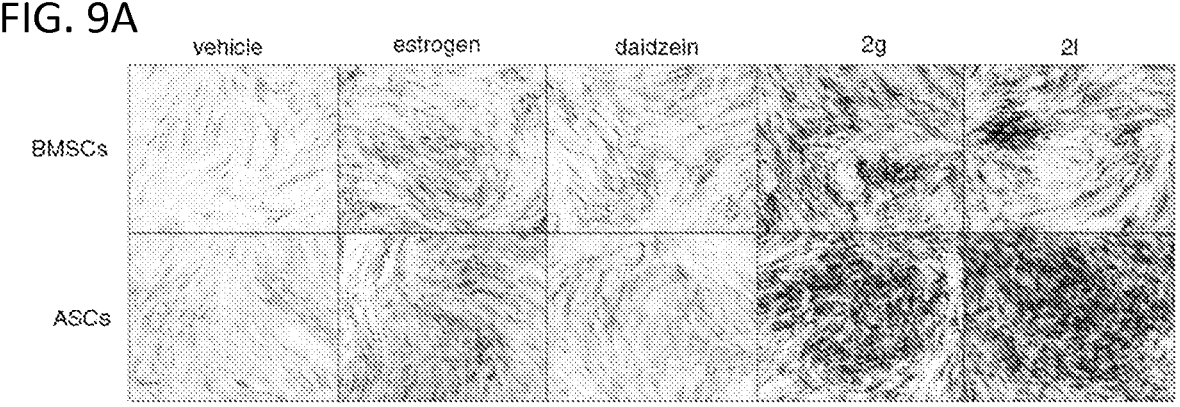
FIGS. 9A-9D are a set of digital images and bar graphs showing that daidzein analogs increase alkaline phosphatase expression and phosphate deposition in BMSCs and ASCs. BMSCs (n=6) and ASCs (n=6) were cultured in osteogenic differentiation media and simultaneously delivered vehicle, estrogen (10 nM), daidzein (1 µM), or daidzein analog (1 µM).
Figure 9B:
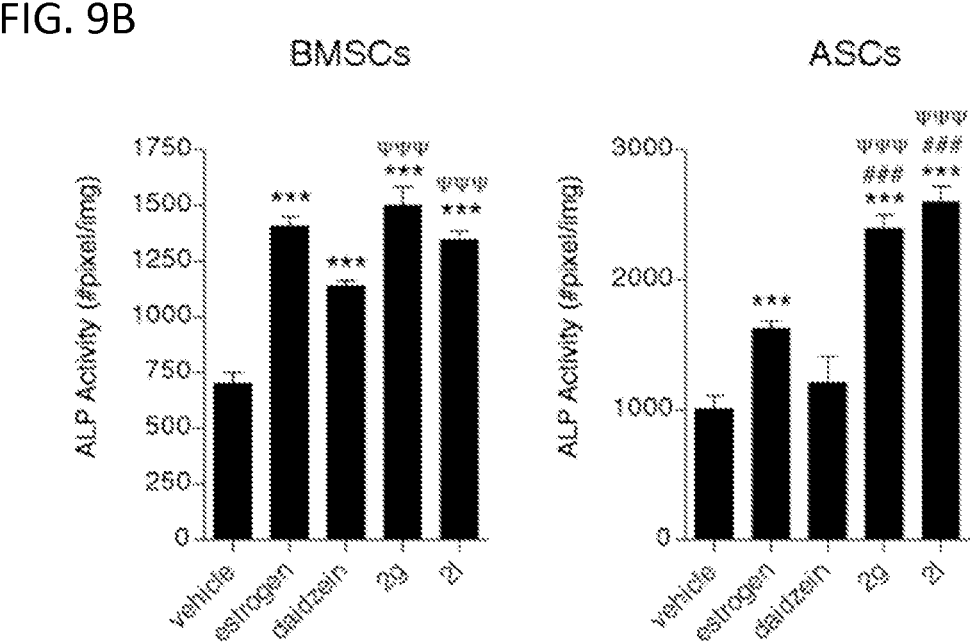

Enhanced Alkaline Phosphatase Activity and Increased Phosphate Deposition was Observed in 2g, and 2l-Treated BMSCs and ASCs Due to the enhanced efficacy of 2g and 2l, additional techniques were utilized to determine whether cells treated with 2g or 2l enhanced early osteogenesis. BMSCs and ASCs were treated with vehicle, estrogen, daidzein, 2g, or 2l for 3 days in osteogenic differentiation media and incubated in BCIP/NBT, the substrate for alkaline phosphatase (ALP) activity detection. After 3 days, BMSCs and ASCs treated with estrogen, 2g, and 2l demonstrated enhanced AP activity (FIGS. 9A-B). More specifically, estrogen enhanced BMSC and ASC differentiation by 2.0 and 1.6-fold, respectively; 2g enhanced differentiation by 2.1 and 2.4-fold; and 2l enhanced differentiation by 1.9 and 2.6-fold ($P<0.05$; FIGS. 9A-B). While daidzein-treated BMSCs demonstrated enhanced ALP activity (1.6-fold increase; $P<0.05$) relative to vehicle, daidzein-treated ASCs displayed similar ALP activity as vehicle-treated ASCs.

Figure 9C:
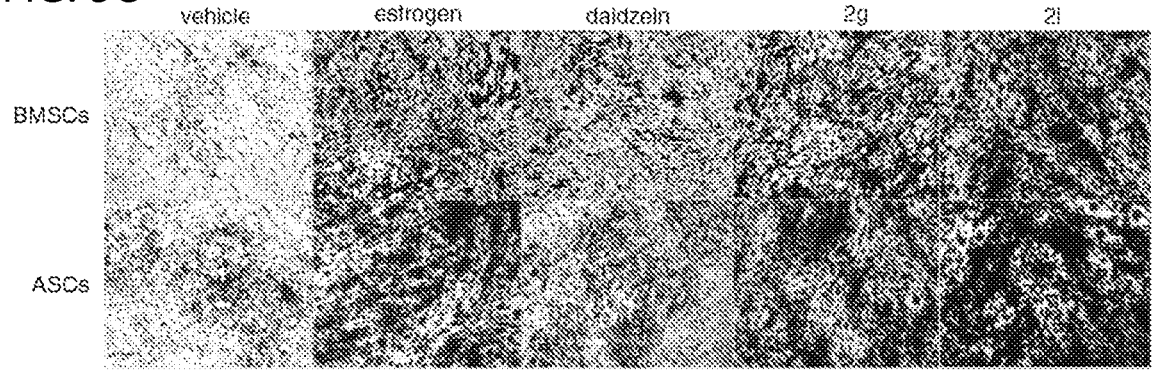
Figure 9D:
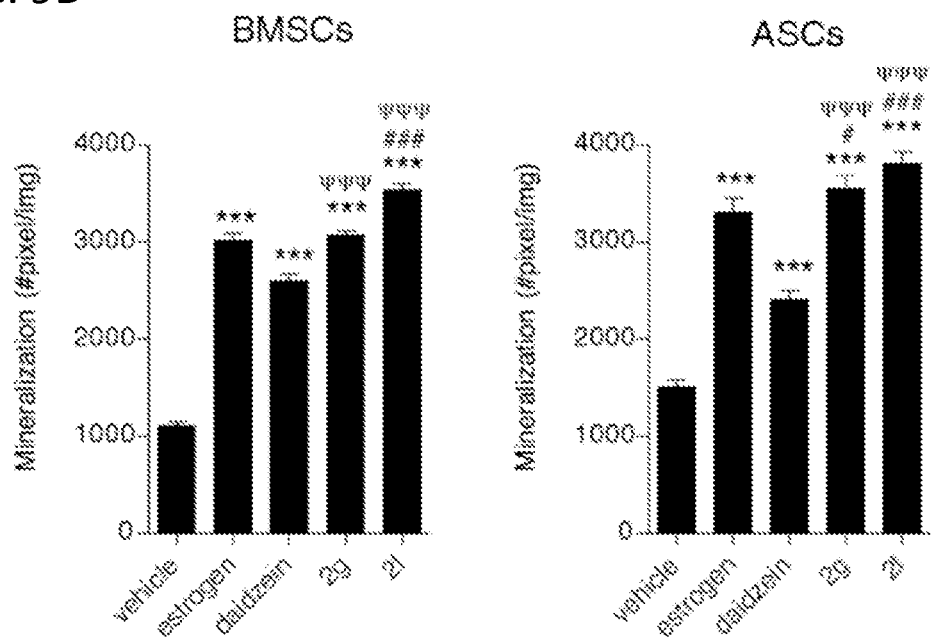

In order to assess phosphate deposition, which is secreted during late osteogenesis and is an essential component of the mature extracellular matrix of bone, cells were treated with vehicle, estrogen, daidzein, 2g or 2l for 14 days in osteogenic differentiation media and incubated in silver nitrate. While estrogen- and daidzein-treated BMSCs and ASCs demonstrated enhanced phosphate deposition, estrogen treatment resulted in greater phosphate deposition than daidzein treatment ($P<0.001$; FIGS. 9C-D). Structural modifications of daidzein into 2g and 2l resulted in increased phosphate deposition, equal to or greater deposition compared to estrogen treatment ($P<0.001$; FIGS. 9C-D). Treatment of BMSCs and ASCs with 2l resulted in the most significant increase in phosphate deposition compared to all other treatment groups ($P<0.001$; FIGS. 9C-D).

Together, these results suggest that BMSCs and ASCs treated with estrogen demonstrate enhanced osteogenesis through increased ALP activity and phosphate deposition. Treatment with daidzein was less effective than estrogen or daidzein analogs. Daidzein analog 2g and 2l also resulted in enhanced ALP activity and phosphate deposition.

Estrogen, Daidzein, 2g, and 2l Treatment Resulted in Distinct Gene Induction Profiles To determine the genes induced by estrogen, daidzein, 2g, or 2l that led to in enhanced osteogenic differentiation. BMSCs and ASCs were treated for 3 days, 7 days, or 14 days in osteogenic differentiation media with or without the addition of the compounds. Cells were collected and the expression of key osteogenic genes was assessed with qPCR. Differences in the onset, the level of expression, and the length of gene expression varied between estrogen, daidzein, 2g, and 2l-treatment and differed between BMSCs and ASCs (FIG. 10; FIG. 11). While similarities exist between the gene expression profiles of BMSCs and ASCs induced by these compounds, significant differences were also observed.

Figure 10:
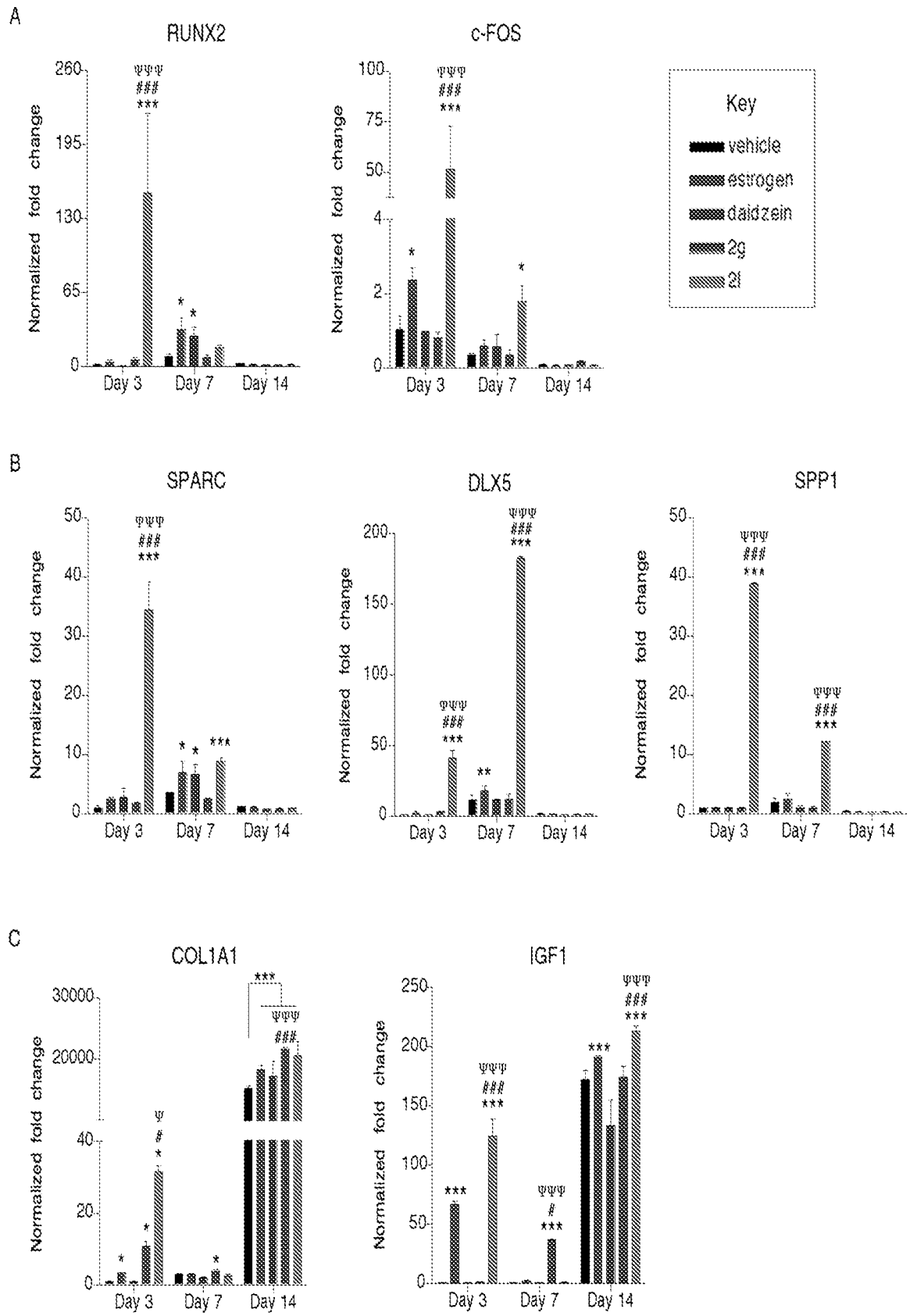
FIGS. 10A-10C are a set of graphs showing the expression of early, middle, and late stage lineage specific osteogenic genes in BMSCs were significantly induced by daidzein analogs. BMSCs were cultured in osteogenic differentiation media and concurrently treated with vehicle, estrogen (10 nM), daidzein (1 µM), or daidzein analog (1 µM). Cells were collected after 3, 7, or 14 days of treatment. RNA was isolated from the cells and reverse transcribed into cDNA. Analysis of (FIG. 10A) early, (FIG. 10B) middle, or (FIG. 10C) late osteogenic transcription factors were assessed by qPCR. Expression values are normalized to undifferentiated vehicle-treated cells normalized to 1.0. *, P<0.05 compared to vehicle-treated BMSCs; ***, P<0.001 compared to vehicle-treated BMSCs; $^{\#}$, P<0.05 compared to estrogen-treated BMSCs; $^{\#\#\#}$, P<0.001 compared to estrogen-treated BMSCs; $^{Y}$, P<0.05 compared to daidzein-treated BMSCs; $^{YYY}$, P<0.001 compared to daidzein-treated BMSCs.
Figure 11:
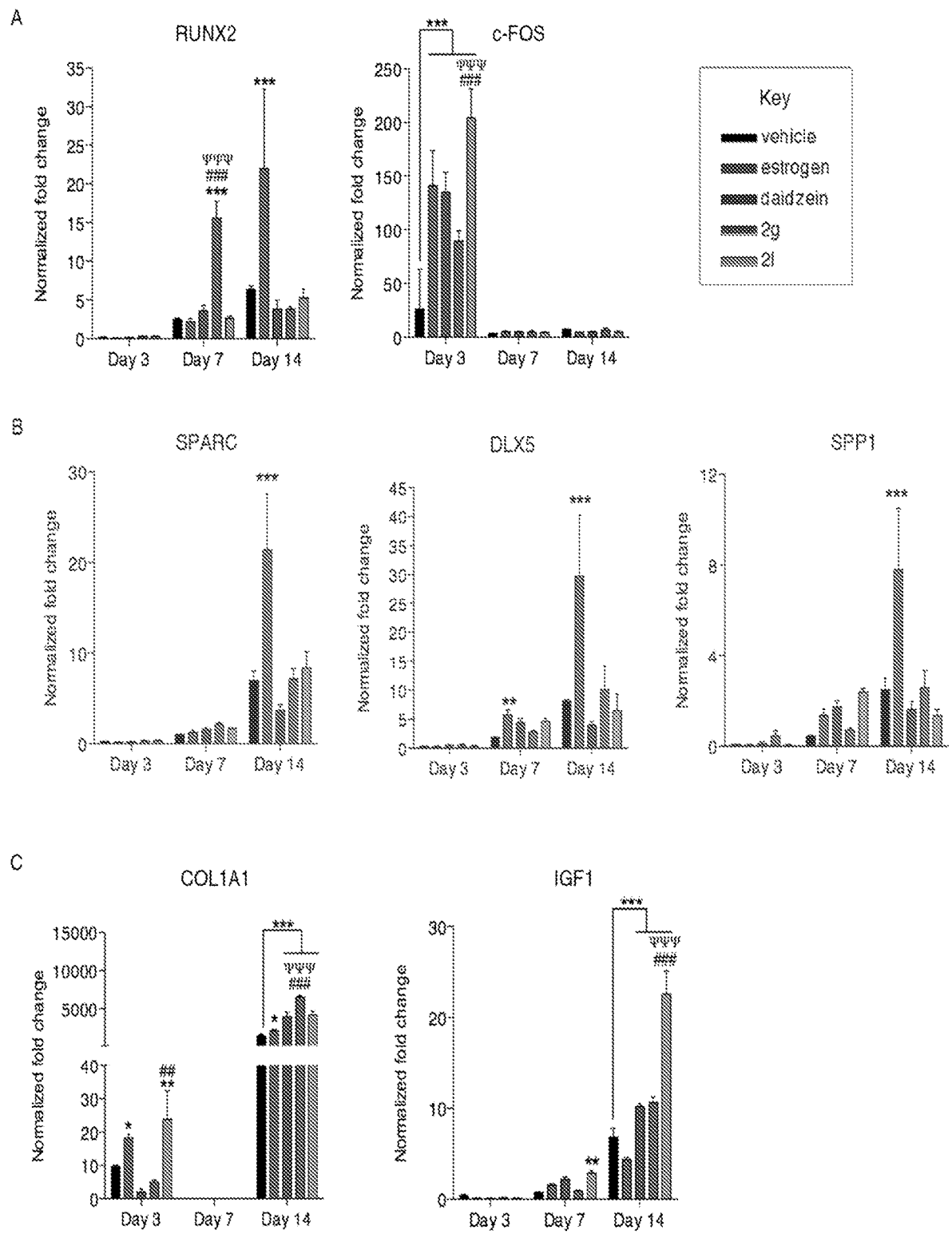
FIGS. 11A-11C are a set of bar graphs showing that expression of early, middle, and late stage lineage specific osteogenic genes in ASCs were significantly induced by daidzein analogs. ASCs were cultured in osteogenic differentiation media and concurrently treated with vehicle, estrogen (10 nM), daidzein (1 µM), or daidzein analog (1 µM). Cells were collected after 3, 7, or 14 days of treatment. RNA was isolated from the cells and reverse transcribed into cDNA. Analysis of (FIG. 11A) early, (FIG. 11B) middle, or (FIG. 11C) late osteogenic transcription factors were assessed by qPCR. Expression values are normalized to undifferentiated vehicle-treated cells normalized to 1.0. *, P<0.05 compared to vehicle-treated ASCs; , P<0.01 compared to vehicle-treated ASCs; *, P<0.001 compared to vehicle-treated ASCs; $^{\#\#\#}$, P<0.001 compared to estrogen-treated ASCs; $^{YYY}$, P<0.001 compared to daidzein-treated ASCs.

BMSCs and ASCs Treated with Estrogen Demonstrate Induction of Early, Middle, and Late Genes Involved in Osteogenesis While BMSCs and ASCs treated with estrogen displayed similar temporal induction of early and late osteogenic genes, significant differences were observed in the induction of mid osteogenic genes (FIG. 10; FIG. 11). More specifically, estrogen induced the expression of early transcription factor c-FOS and COL1A1 within 3 days of estrogen treatment in both BMSCs and ASCs ($P<0.05$; FIG. 10; FIG. 11). While these genes were similarly induced following 3 days and 14 days of estrogen treatment, the levels of gene induction varied between BMSCs and ASCs. Following 3 days of treatment, estrogen increased c-FOS expression by 2.4-fold in BMSCs, while ASCs enhanced c-FOS expression by 141.1-fold, relative to undifferentiated cells. The induction of COL1A1 expression was different between BMSCs and ASCs: 3.4-fold in BMSCs and 18.3-fold in ASCs, relative to undifferentiated cells (FIG. 10; FIG. 11). These results highlight the differences in response to estrogen stimulation.

Furthermore, differences were observed in the effects of estrogen on middle osteogenic genes both temporally and in relation to induction level. SPARC and DLX5 was upregulated following 7 days of estrogen treatment in BMSCs, while SPARC, DLX5, and SPP1 was upregulated following 14 days of treatment in ASCs (FIG. 10; FIG. 11). The level of induction in the middle genes between BMSCs and ASCs significantly varied following treatment with estrogen. Estrogen-treated BMSCs displayed higher levels of induction in the middle genes on day 7 (SPARC: 6.9-fold in BMSCs vs 1.3-fold in ASCs; DLX5: 17.8-fold in BMSCs vs 5.8-fold in ASCs; FIG. 10; FIG. 11).

Additional differences between BMSCs and ASCs associated with estrogen stimulation were in RUNX2 and IGF1 expression. RUNX2 expression in BMSCs was increased (9.1-fold) following 7 days of estrogen treatment, while enhanced RUNX2 expression in ASCs (22.0-fold) did not occur until 14 days (FIG. 10; FIG. 11). IGF1 induction was significantly enhanced in BMSCs following estrogen treatment on day 3 in BMSCs, while this effect was not observed in ASCs (FIG. 10; FIG. 11). Together, these results suggest that estrogen stimulates the expression of osteogenic genes in both BMSCs and ASCs.

Daidzein-Treated BMSCs and ASCs Display Different Gene Expression Profiles

BMSCs and ASCs were treated with daidzein and stimulated to undergo osteogenic differentiation. Cells were collected after 3, 7, and 14 days, and the expression of key osteogenic factors were investigated by qPCR. Daidzein-treated BMSCs increased RUNX2 and SPARC expression after 7 days of osteogenic differentiation by 9.1-fold and 3.6-fold, respectively, relative to undifferentiated BMSCs ($P<0.05$; FIG. 10). Daidzein-treated ASCs increased c-FOS expression by 134.9-fold after 3 days and COL1A1 and IGF1 expression by 3899.6-fold and 10.2-fold, respectively, after 14 days ($P<0.001$; FIG. 11. These results suggest that daidzein induce different signaling cascades in BMSCs and ASCs that result in increased osteogenic differentiation.

Figure 12:
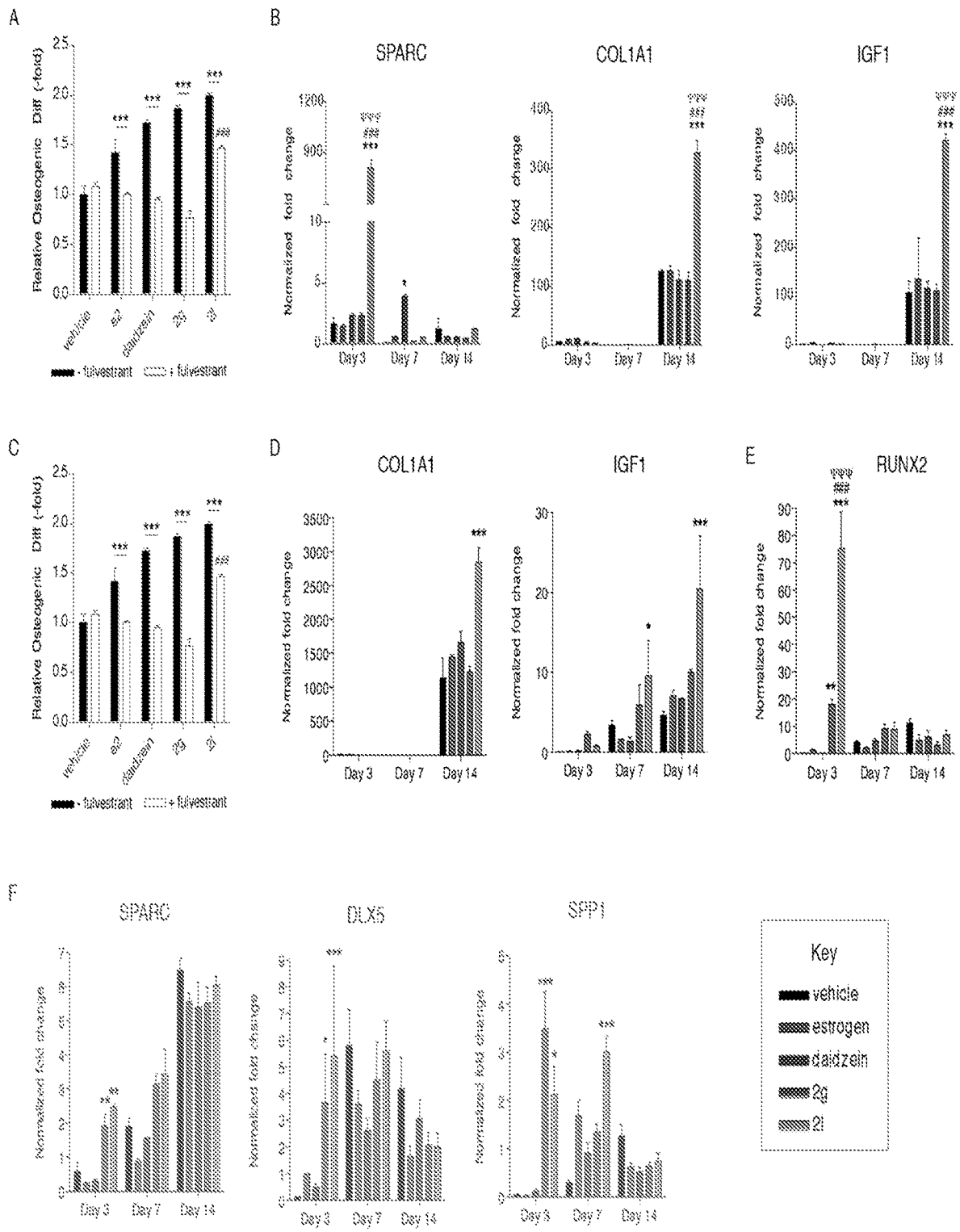
FIGS. 12A-12F are a set of bar graphs showing that fulvestrant treatment reduces osteogenic induction by daidzein analogs through inhibition of early, middle, and/or late osteogenic transcription. BMSCs or ASCs were cultured in osteogenic differentiation media and concurrently treated with vehicle, estrogen (10 nM), daidzein (1 µM), or daidzein analog (1 µM) and estrogen antagonist fulvestrant.

Furthermore, to determine the estrogenic activity of daidzein, estrogen inhibitor studies were performed on BMSCs and ASCs by treating cells with daidzein and anti-estrogen fulvestrant. Fulvestrant reduced the osteogenic potential of daidzein-treated BMSCs and ASCs from 1.7-fold to 1.0-fold and from 1.5 to 1.0, respectively (FIG. 12). Furthermore, molecular analysis of the genes altered by simultaneous fulvestrant treatment with daidzein was conducted. Fulvestrant reduced RUNX2 expression in BMSCs and c-FOS, COL1A1, and IGF1 expression in ASCs (FIG. 12). While daidzein increased the expression of RUNX2 on day 7, simultaneous treatment with fulvestrant reduced RUNX2 expression by 2.7-fold ($P<0.05$; FIG. 10; FIG. 12). With respect to ASCs, fulvestrant reduced c-FOS by 5.2-fold on day 3 (from 5.4-fold to 1.2-fold; $P<0.001$), IGF1 by 2.4-fold on day 7 (from 2.8-fold to 0.4-fold; $P<0.01$), and COL1A1 1.1-fold on day 14 (from 2.6-fold to 1.5-fold; $P<0.05$; FIG. 11; FIG. 12). These inhibitor studies suggest that daidzein works through an estrogen dependent mechanism as fulvestrant treatment reduced expression of genes activated by daidzein.

Daidzein Analog 2g Enhanced Osteogenic Differentiation in an Estrogen Dependent Mechanism Similar to estrogen, 2g enhanced a small set of genes induced by estrogen: RUNX2, COL1A1, and IGF1. BMSCs treated with 2g increased RUNX2 expression by 7.9-fold on day 7 ($P<0.001$; FIG. 10). Furthermore, BMSCs treated with 2g increased the expression of COL1A1 on day 3, 7, and 14 by 10.8-fold, 4.1-fold, and 21,600.4-fold, respectively ($P<0.05$; FIG. 10). The expression of COL1A1 was significantly more robust compared to estrogen-treated or daidzein-treated BMSCs on day 14 ($P<0.001$; FIG. 10C). ASCs treated with 2g demonstrated similar increased expression of COL1A1 compared to vehicle-, estrogen-, or daidzein-treated ASCs on day 14 ($P<0.001$; FIG. 11C).

To confirm the estrogenic activity of 2g, inhibitor studies were conducted with BMSCs and ASCs by simultaneously treating cells with 2g and fulvestrant in osteogenic differentiation media for 3, 7, or 14 days. Fulvestrant treatment reduced the osteogenic activity of 2g in BMSCs and ASCs to levels comparable to vehicle-treated cells from 1.9-fold to 0.8-fold and 2.0-fold to 0.9-fold, respectively ($P<0.001$; FIG. 12). Furthermore, fulvestrant reduced the expression of RUNX2, COL1A1, and IGF1 in BMSCs and ASCs. Specifically, BMSCs treated with 2g and fulvestrant displayed reduced RUNX2 expression by 3.4-fold on day 3, reduced COL1A1 expression by 9.9-fold on day 3, and IGF1 expression by 40.0-fold on day 14 ($P<0.05$). With respect to ASCs, fulvestrant inhibited the activity of 2g by reducing RUNX2 expression on day 7 by 4.1-fold and COL1A1 expression on day 14 by 3.3-fold ($P<0.01$). Together these results indicate that 2g acts through an estrogen-mediated mechanism, with reduced activity in the presence of fulvestrant both phenotypically and molecularly.

The Effects of Daidzein Analog 2l on Osteogenesis is Through Both Estrogen Dependent and Independent Mechanisms Unlike estrogen, daidzein, and 2g, BMSCs treated with 2l showed increased expression of all early, middle, and late osteogenic genes investigated in this study. Relative to undifferentiated BMSCs, BMSCs treated with 2l demonstrated an enhanced expression of RUNX2, c-FOS, SPARC, DLX5, SPP1, COL1A1, IGF1 by 152.8-fold, 51.6-fold, 34.4-fold, 41.2-fold, 38.8-fold, 31.8-fold, and 124.4-fold, respectively, on day 3 ($P<0.05$; FIG. 10). Daidzein analog 2l continued to induce the expression of c-FOS, SPARC, DLX5, and SPP1 by 1.8-fold, 8.9-fold, 182.8-fold, and 12.3-fold, respectively, on day 7 ($P<0.05$; FIG. 10). Additionally, 2l-treated BMSCs displayed increased late osteogenic genes COL1A1 and IGF1 even on day 14($P<0.05$; FIG. 10). These results suggest that 2l significantly induces osteogenesis through induction of key osteogenic regulatory genes to initiate and maintain osteogenesis.

While the effects on BMSCs were pronounced, the effects on ASCs were attenuated. ASCs treated with 2l displayed similar increases in gene induction but were limited to c-FOS, COL1A1, and IGF1. ASCs treated with 2l displayed enhanced c-FOS expression by 204.5-fold after 3 days ($P<0.05$; FIG. 11). After 14 days of differentiation, 2l-treated ASCs displayed higher expression of COL1A1 (4139.8-fold) compared to vehicle-treated (1471.7-fold) or estrogen-treated (2061.2-fold) ASCs ($P<0.05$; FIG. 11). Likewise, IGF-1 expression in 14-day differentiated ASCs treated with 2l demonstrated increased IGF expression (22.6-fold) compared to vehicle-treated ASCs (6.8-fold) or estrogen-treated ASCs (4.4-fold; $P<0.05$; FIG. 11).

To further determine the estrogenic activity of 2l, concomitant treatment of 2l with fulvestrant resulted in reduced osteogenesis in BMSCs and ASCs. However, osteogenic differentiation was not completely inhibited by fulvestrant, suggesting that 2l-induced osteogenesis is through both estrogenic and non-estrogenic activity. More specifically, BMSCs and ASCs treated with 2l demonstrated a 2.0-fold and 2.4-fold increase in osteogenesis, respectively (FIG. 12). Simultaneous delivery of fulvestrant with 2l reduced the osteogenesis of BMSCs and ASCs to 1.5-fold and 1.7-fold, respectively ($P<0.001$; FIG. 12). Furthermore, fulvestrant reduced the expression of early and middle transcription factors in both BMSCs and ASCs, suggesting that the estrogenic mechanism of fulvestrant on osteogenesis is through the induction of early to mid osteogenic genes. COL1A1 and IGF1 expression remained induced in BMSCs in the presence of fulvestrant even in the presence of fulvestrant (FIG. 12), suggesting that 2l utilizes an alternative non-estrogen driven pathway to induce osteogenesis that results in the downstream upregulation of COL1A1 and IGF1.

Discussion

Osteoporosis is a disease characterized by decreasing BMD and a loss of the bone architecture, resulting in increased fragility and fracture incidence. To reduce the progression of the disease and increase bone strength, development of new compounds to increase osteogenesis is necessary. In the studies presented herein, synthetic daidzein analogs have been tested for their in vitro osteogenic potential in both BMSCs and ASCs. Daidzein analogs 2g and 2l were found to increase osteogenic differentiation characterized by alizarin red staining, alkaline phosphate staining, and silver nitrate staining. In addition, these daidzein analogs enhanced osteogenic differentiation of BMSCs and ASCs relative to estrogen or daidzein-treated cells. Furthermore, simultaneous treatment with fulvestrant eliminated the osteogenic activity of 2g and attenuated the osteogenic activity of 2l, suggesting that 2g acts predominantly through the estrogen receptor pathway while 2l may use both an estrogen receptor dependent and independent pathway. Analysis of transcript levels of key osteogenic genes showed that 2g and 2l differentially induced osteogenic genes in BMSCs and ASCs, suggesting that these two compounds induce osteogenesis differently.

Consistent with previously published studies, genistein increased the osteogenic potential of BMSCs and ASCs. Previous work by Bitto et al. demonstrated that genistein enhanced the BMD but also restored structure to ovariectomy-induced osteoporotic bone in rats (see e.g. Bitto et al., *Br J Pharmacol* 2008, 155:896-905; and Bitto et al., *Curr Med Chem* 2010, 17:3007-3018. Furthermore, it was observed that the effects of genistein treatment in rats improved the overall architecture and strength of the bone better than raloxifene, a commonly used selective estrogen receptor modulator used to treat osteoporosis. Additional studies have shown that genistein inhibits bone resorption activity of osteoclasts and stimulate osteogenic differentiation and maturation of BMSCs and osteoblasts. Ming and colleagues determined that genistein enhanced ER, p38MAPK-Runx2, NO/cGMP pathways and inhibited bone resorption through induction of osteoclastogenic inhibitor osteoprotegerin (OPG). These studies provide support for the finding that genistein reduced bone loss and increased BMD in osteopenic postmenopausal or early postmenopausal women, comparable to women treated with hormone replacement therapy.

Comparative studies have shown that daidzein is more effective than genistein in preventing ovariectomy-induced bone loss in rats Picherit et al., *J Nutr* 2000, 130:1675-1681, which is specifically incorporated herein to the extent that it teaches a model of ovariectomy-Induced Bone Loss in Rats. Daidzein was shown to enhance BMD in lumbar vertebrae, femur, and in the metaphyseal and diaphyseal zones, which have been shown to be rich in cancellous and cortical bone, respectively. While the effects observed with daidzein treatment was comparable to estrogen treatment, genistein treatment only resulted in increased bone density in the diaphyseal zone. Daidzein treatment has also been shown to increase biomechanical strength by increasing collagen formation, while reducing osteoclast activity to limit the amount of degradation to the extracellular matrix. Together, daidzein treatment leads to reduced resorptive activity and increased anabolic activity in bone. The results of this study provide additional support for the anabolic activity of daidzein in BMSCs and ASCs. Additional studies have shown that daidzein with high calcium preserve bone mass and biomechanical strength in multiple sites in an ovariectomized mouse model, providing for the supplementation of daidzein with current osteoporosis treatment regimes.

While these phytoestrogens have proven to be effective in increasing bone density in rodent models, novel daidzein derivatives developed disclosed herein were tested to determine their potential enhanced osteogenic activity on human BMSCs and ASCs for bone differentiation and regeneration. In certain examples disclosed herein which modified the 7-OH by substituting the hydrogen with an isopropyl (2c), a cyclopentyl (2g), or an allyl (2l) while retaining the 4-hydroxy moiety resulted in a lower estrogenic activity than daidzein and yielded significantly increased osteogenic activity. Higher dosages of compounds 2g and 2l in in the studies disclosed herein did not negatively impact the osteogenic activity of the cells, nor lead to cytotoxicity.

Although the analog 2g possessed much weaker estrogenic activity than estrogen, 2g treatment enhanced RUNX2, SPARC, and IGF1 in BMSCs and RUNX2 and COL1A1 in ASCs. RUNX2 is believed essential for osteoblast development and proper bone formation by regulating transcription of numerous genes that control osteoblast development from mesenchymal stem cells and maturation. SPARC, IGF1, and COL1A1 have all been implicated in increasing BMD, increasing biomechanical strength, and maintaining of the extracellular matrix. The inhibitory effect of fulvestrant on the osteogenic activity of 2g-treated BMSCs and ASCs demonstrates the estrogenic activity of 2g, indicating that the weaker analog 2g appears to enhance osteogenic activity through signaling pathways associated with estrogen receptor.

Likewise, structural modification of daidzein into 2l also enhanced osteogenic differentiation of BMSCs and ASCs, possibly due to an estrogen-like mechanism. Interestingly, unlike 2g, fulvestrant treatment did not abolish the osteogenic activity of 2l, suggesting that 2l is likely to be acting through an estrogen independent mechanism. BMSCs and ASCs treated with 2l demonstrated alterations in the transcriptional level of early, middle, and late osteogenic genes involved in differentiation of the cells and mineralization of the extracellular matrix. In BMSCs treated with 2l, all osteogenic genes were upregulated, indicating a powerful effect of 2l on BMSCs. In contrast, ASCs treated with 2l demonstrated a less pronounced effect, altering c-FOS, COL1A1, and IGF1.

These studies further demonstrated that these compounds have similar effects on ASCs as BMSCs. The study of daidzein analogs further show that minor structural modifications of daidzein further increase osteogenic differentiation of BMSCs and ASCs, although the effect was more pronounced in ASCs. Both BMSCs and ASCs are derived from the same germ layer and as such possess similar biologic characteristics. However, in depth analysis of these two cell types has recently revealed differences in immunophenotypical and gene expression profiles. For example, Monaco and colleagues determined that during early osteogenic differentiation, ASCs have larger lipid metabolism, migration, and immunomodulatory capacity compared to BMSCs, while BMSCs have larger induction of inflammation, cell growth and proliferation (Monaco et al., *PLoS One* 2012, 7:1-19. This previously published data is consistent with the results presented herein, which demonstrated differences in the transcript levels in analysis between BMSCs and ASCs, and suggest that these two cell types undergo osteogenic differentiation via differing mechanism of action.

In view of the many possible embodiments to which the principles of the disclosed invention may be applied, it should be recognized that the illustrated embodiments are only preferred examples of the invention and should not be taken as limiting the scope of the invention. Rather, the scope of the invention is defined by the following claims. We therefore claim as our invention all that comes within the scope and spirit of these claims.

We claim:

1. A compound, having the formula:

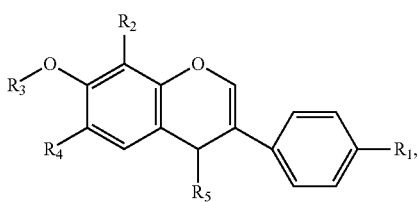

wherein
$R_1$ is $OR_9$, and wherein the $R_9$ is hydrogen;
$R_2$ is hydrogen;
$R_3$ is n-propyl, isobutyl, cyclopentyl, n-hexyl, propyne, or 2-(Piperdin-1-yl)ethyl;
$R_4$ is hydrogen;
$R_5$ is one or more of hydrogen, oxygen, or $OR_{10}$, wherein $R_{10}$ is hydrogen or alkyl having one to four carbons, and when $R_5$ is oxygen, $R_3$ is 2-(Piperdin-1-yl)ethyl.

2. The compound of claim 1, wherein $R_5$ is oxygen or two hydrogens.

3. The compound of claim 1, wherein the compound is 3-(4-Hydroxyphenyl)-7-(2-(piperidin-1-yl)ethoxy)-4H-chromen-4-one.

4. A composition, comprising the compound of claim 1, and a pharmaceutically acceptable carrier.

5. The composition of claim 4, wherein the composition is formulated for oral, intravenous, intradermal, intramuscular, and subcutaneous administration.

6. The composition of claim 5, wherein the composition comprises a product for oral delivery comprising a concentrate, a dried powder, a liquid, a capsule, a pellet, and a pill.

7. The composition of claim 4, further comprising mesenchymal stem cells, wherein in the mesenchymal stem cells have optionally been pretreated with the compound of claim 1, daidzein, glycinol, glyceollin I, glyceollin II, or any combination thereof.

8. A method of preventing or treating a bone defect in a subject, comprising:
administering to the subject an effective amount of the compound of claim 1 to a subject, thereby preventing or treating bone disease or bone injury.

9. The method of claim 8, wherein the subject has or is believed to have osteoporosis, has been diagnosed as having osteoporosis, and/or has a bone fracture.

10. A method of stimulating bone growth in a subject, comprising:
   administering to the subject an effective amount of the compound of claim 1 to a subject, thereby stimulating bone growth.

* * * * *

SEQUENCE LISTING

```
<160> NUMBER OF SEQ ID NOS: 24

<210> SEQ ID NO 1
<211> LENGTH: 18
<212> TYPE: DNA
<213> ORGANISM: Homo sapiens

<400> SEQUENCE: 1
ccagtgtcta cacctctc                                                  18

<210> SEQ ID NO 2
<211> LENGTH: 18
<212> TYPE: DNA
<213> ORGANISM: Homo sapiens

<400> SEQUENCE: 2
atggagtagg agtgttgc                                                  18

<210> SEQ ID NO 3
<211> LENGTH: 19
<212> TYPE: DNA
<213> ORGANISM: Homo sapiens

<400> SEQUENCE: 3
ctgtgatcta aggaggctg                                                 19
```

```
<210> SEQ ID NO 4
<211> LENGTH: 20
<212> TYPE: DNA
<213> ORGANISM: Homo sapiens

<400> SEQUENCE: 4
ttcgtgttct tgttggtaga                                              20

<210> SEQ ID NO 5
<211> LENGTH: 20
<212> TYPE: DNA
<213> ORGANISM: Homo sapiens

<400> SEQUENCE: 5
ctaactcctt agtgccagag                                              20

<210> SEQ ID NO 6
<211> LENGTH: 21
<212> TYPE: DNA
<213> ORGANISM: Homo sapiens

<400> SEQUENCE: 6
catgatgaca ttcttagcca c                                            21

<210> SEQ ID NO 7
<211> LENGTH: 23
<212> TYPE: DNA
<213> ORGANISM: Homo sapiens

<400> SEQUENCE: 7
gctctagaat gagaattgca ctg                                          23

<210> SEQ ID NO 8
<211> LENGTH: 20
<212> TYPE: DNA
<213> ORGANISM: Homo sapiens

<400> SEQUENCE: 8
gtcaatggag tcctggctgt                                              20

<210> SEQ ID NO 9
<211> LENGTH: 20
<212> TYPE: DNA
<213> ORGANISM: Homo sapiens

<400> SEQUENCE: 9
caccttctac aatgagctgc                                              20

<210> SEQ ID NO 10
<211> LENGTH: 20
<212> TYPE: DNA
<213> ORGANISM: Homo sapiens

<400> SEQUENCE: 10
tcttctcgat gctcgacgga                                              20

<210> SEQ ID NO 11
<211> LENGTH: 20
<212> TYPE: DNA
<213> ORGANISM: Homo sapiens

<400> SEQUENCE: 11
ctcactacca cacctacctg                                              20
```

```
<210> SEQ ID NO 12
<211> LENGTH: 24
<212> TYPE: DNA
<213> ORGANISM: Homo sapiens

<400> SEQUENCE: 12
tcaatatggt cgccaaacag attc                                          24

<210> SEQ ID NO 13
<211> LENGTH: 20
<212> TYPE: DNA
<213> ORGANISM: Homo sapiens

<400> SEQUENCE: 13
cctgtcaaga gcatcagcag                                               20

<210> SEQ ID NO 14
<211> LENGTH: 20
<212> TYPE: DNA
<213> ORGANISM: Homo sapiens

<400> SEQUENCE: 14
gtcagaggaa ggctcattgc                                               20

<210> SEQ ID NO 15
<211> LENGTH: 20
<212> TYPE: DNA
<213> ORGANISM: Homo sapiens

<400> SEQUENCE: 15
tgtgggagct aatcctgtcc                                               20

<210> SEQ ID NO 16
<211> LENGTH: 21
<212> TYPE: DNA
<213> ORGANISM: Homo sapiens

<400> SEQUENCE: 16
tcaggacgtt cttgagccag t                                             21

<210> SEQ ID NO 17
<211> LENGTH: 20
<212> TYPE: DNA
<213> ORGANISM: Homo sapiens

<400> SEQUENCE: 17
tggcccgagt cttcagctac                                               20

<210> SEQ ID NO 18
<211> LENGTH: 20
<212> TYPE: DNA
<213> ORGANISM: Homo sapiens

<400> SEQUENCE: 18
tggttggtcg gtctctttct                                               20

<210> SEQ ID NO 19
<211> LENGTH: 23
<212> TYPE: DNA
<213> ORGANISM: Homo sapiens

<400> SEQUENCE: 19
gctctagaat gagaattgca ctg                                           23
```

```
<210> SEQ ID NO 20
<211> LENGTH: 20
<212> TYPE: DNA
<213> ORGANISM: Homo sapiens

<400> SEQUENCE: 20
tgtcggtcct gaggtaactg                                               20

<210> SEQ ID NO 21
<211> LENGTH: 22
<212> TYPE: DNA
<213> ORGANISM: Homo sapiens

<400> SEQUENCE: 21
catgttcagc tttgtggacc tc                                            22

<210> SEQ ID NO 22
<211> LENGTH: 21
<212> TYPE: DNA
<213> ORGANISM: Homo sapiens

<400> SEQUENCE: 22
aggtgattgg tgggatgtct t                                             21

<210> SEQ ID NO 23
<211> LENGTH: 19
<212> TYPE: DNA
<213> ORGANISM: Homo sapiens

<400> SEQUENCE: 23
ctgtgatcta aggaggctg                                                19

<210> SEQ ID NO 24
<211> LENGTH: 20
<212> TYPE: DNA
<213> ORGANISM: Homo sapiens

<400> SEQUENCE: 24
ttcgtgttct tgttggtaga                                               20
```